United States Patent [19]
Tung et al.

[11] Patent Number: 5,945,413
[45] Date of Patent: Aug. 31, 1999

[54] ASPARTYL PROTEASE INHIBITORS

[75] Inventors: Roger Dennis Tung, Arlington; Francesco Gerald Salituro, Marlborough; David D. Deininger, Arlington; Govinda Rao Bhisetti, Lexington; Christopher Todd Baker, Waltham, all of Mass.; Andrew Spaltenstein, Raleigh, N.C.

[73] Assignee: Vertex Pharmaceuticals Incorporated, Cambridge, Mass.

[21] Appl. No.: 08/724,563

[22] Filed: Sep. 30, 1996

Related U.S. Application Data

[63] Continuation-in-part of application No. 08/592,777, Jan. 26, 1996.

[51] Int. Cl.$^6$ ............... A61K 41/315; A61K 31/43; A61K 31/47; A61K 31/44; A61K 31/41; A61K 31/425; A61K 31/415; A61K 31/40

[52] U.S. Cl. ............... 514/193; 514/252; 514/235.8; 514/307; 514/341; 514/362; 514/369; 514/397; 514/398; 514/400; 514/409; 514/418; 544/6; 544/133; 544/165; 544/357; 544/360; 544/363; 544/370; 546/210; 546/278.4; 548/134; 548/214; 548/315.4; 548/323.5; 548/324.01; 548/340.5; 548/550; 548/517

[58] Field of Search ............... 548/323.5, 324.1, 548/324.5, 315.4, 134, 214, 517, 550; 514/398, 397, 400, 193, 222, 235.8, 307, 341, 362, 369, 409, 418; 546/210, 278.4; 544/6, 133, 165, 357, 363, 370, 360

[56] References Cited

U.S. PATENT DOCUMENTS

| | | | |
|---|---|---|---|
| 3,882,120 | 5/1975 | Piesch et al. | 548/323.5 X |
| 4,413,130 | 11/1983 | White | 548/323.5 X |
| 5,288,873 | 2/1994 | Su et al. | 548/323.5 |
| 5,436,351 | 7/1995 | Coffey et al. | 548/324.1 |

OTHER PUBLICATIONS

Marquez et al, J. Org. Chem., vol. 37, No. 16, pp 2558 to 2561 (1972).

*Primary Examiner*—Floyd D. Higel
*Attorney, Agent, or Firm*—Fish & Neave; James F. Haley, Jr.; N. Govindaswamy

[57] ABSTRACT

This invention relates to a novel class of compounds that are aspartyl protease inhibitors. In one embodiment, this invention relates to a novel class of aspartyl protease inhibitors characterized by specific structural and physicochemical features. This invention also relates to pharmaceutical compositions comprising these compounds. The compounds and pharmaceutical compositions of this invention are particularly well suited for inhibiting HIV-1 and HIV-2 protease activity and consequently, may be advantageously used as anti-viral agents against the HIV-1 and HIV-2 viruses. This invention also relates to methods for inhibiting aspartyl protease activity and methods for treating viral infections using the compounds and compositions of this invention.

44 Claims, No Drawings

ASPARTYL PROTEASE INHIBITORS

CROSS-REFERENCE TO RELATED APPLICATIONS

This application is a continuation-in-part of U.S. application Ser. No. 08/592,777, filed Jan. 26, 1996, now pending.

TECHNICAL FIELD OF THE INVENTION

The present invention relates to a novel class of compounds which are aspartyl protease inhibitors. In one embodiment, this invention relates to a novel class of HIV aspartyl protease inhibitors characterized by specific structural and physicochemical features. This invention also relates to pharmaceutical compositions comprising these compounds. The compounds and pharmaceutical compositions of this invention are particularly well suited for inhibiting HIV-1 and HIV-2 protease activity and consequently, may be advantageously used as anti-viral agents against the HIV-1 and HIV-2 viruses. This invention also relates to methods for inhibiting aspartyl protease activity and methods for treating viral infections using the compounds and compositions of this invention.

BACKGROUND OF THE INVENTION

The human immunodeficiency virus ("HIV") is the causative agent for acquired immunodeficiency syndrome ("AIDS")—a disease characterized by the destruction of the immune system, particularly of $CD4^+$ T-cells, with attendant susceptibility to opportunistic infections—and its precursor AIDS-related complex ("ARC")—a syndrome characterized by symptoms such as persistent generalized lymphadenopathy, fever and weight loss.

As in the case of several other retroviruses, HIV encodes the production of a protease which carries out post-translational cleavage of precursor polypeptides in a process necessary for the formation of infectious virions (S. Crawford et al., "A Deletion Mutation in the 5' Part of the pol Gene of Moloney Murine Leukemia Virus Blocks Proteolytic Processing of the gag and pol Polyproteins", *J. Virol.*, 53, p. 899 (1985)). These gene products include pol, which encodes the virion RNA-dependent DNA polymerase (reverse transcriptase), an endonuclease, HIV protease, and gag, which encodes the core-proteins of the virion (H. Toh et al., "Close Structural Resemblance Between Putative Polymerase of a Drosophila Transposable Genetic Element 17.6 and pol gene product of Moloney Murine Leukemia Virus", *EMBO J.*, 4, p. 1267 (1985); L. H. Pearl et al., "A Structural Model for the Retroviral Proteases", *Nature*, pp. 329–351 (1987); M. D. Power et al., "Nucleotide Sequence of SRV-1, a Type D Simian Acquired Immune Deficiency Syndrome Retrovirus", *Science*, 231, p. 1567 (1986)).

A number of synthetic anti-viral agents have been designed to target various stages in the replication cycle of HIV. These agents include compounds which block viral binding to $CD4^+$ T-lymphocytes (for example, soluble CD4), and compounds which interfere with viral replication by inhibiting viral reverse transcriptase (for example, didanosine and zidovudine (AZT)) and inhibit integration of viral DNA into cellular DNA (M. S. Hirsh and R. T. D'Aqulia, "Therapy for Human Immunodeficiency Virus Infection", *N.Eng.J.Med.*, 328, p. 1686 (1993)). However, such agents, which are directed primarily to early stages of viral replication, do not prevent the production of infectious virions in chronically infected cells. Furthermore, administration of some of these agents in effective amounts has led to cell-toxicity and unwanted side effects, such as anemia and bone marrow suppression.

More recently, drug design efforts have been directed toward creating compounds which inhibit the formation of infectious virions by interfering with the processing of viral polyprotein precursors. Processing of these precursor proteins requires the action of virus-encoded proteases which are essential for replication (Kohl, N. E. et al. "Active HIV Protease is Required for Viral Infectivity" *Proc. Natl. Acad. Sci. USA*, 85, p. 4686 (1988)). The anti-viral potential of HIV protease inhibition has been demonstrated using peptidal inhibitors. Such peptidal compounds, however, are typically large and complex molecules that tend to exhibit poor bioavailability and are not generally consistent with oral administration. Accordingly, the need still exists for compounds that can effectively inhibit the action of viral proteases, for use as agents for preventing and treating chronic and acute viral infections. Such agents would be expected to act as effective therapeutic agents in their own right. In addition, since they act at a separate stage in the virus life cycle from previously described antiretroviral agents, the administration of a combination of agents would be expected to result in increased therapeutic efficacy.

SUMMARY OF THE INVENTION

The present invention provides a novel class of compounds, and pharmaceutically acceptable derivatives thereof, that are useful as inhibitors of aspartyl proteases, and in particular, HIV aspartyl protease. The compounds of this invention can be used alone or in combination with other therapeutic or prophylactic agents, such as anti-virals, antibiotics, immunomodulators or vaccines, for the treatment or prophylaxis of viral infection.

According to a preferred embodiment, the compounds of this invention are capable of inhibiting HIV viral replication in human $CD_4^+$ cells including T-cells, monocytic lines including macrophages and dendrocytes and other permissive cells. These compounds are useful as therapeutic and prophylactic agents to treat or prevent infection by HIV-1 and related viruses which may result in asymptomatic infection, AIDS-related complex ("ARC"), acquired immunodeficiency syndrome ("AIDS"), or similar disease of the immune system.

It is a principal object of this invention to provide a novel class of compounds that are aspartyl protease inhibitors, and particularly, HIV aspartyl protease inhibitors. This novel class of compounds is represented by formula I:

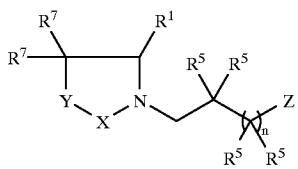

(I)

wherein
each Z is

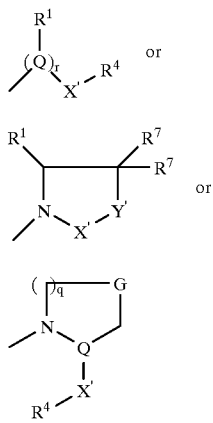

wherein any Z may be optionally fused with $R^6$;
  each X and X' is independently selected from the group consisting of —C(O)—, —C(O)C(O)—, —S(O)— and —S(O)$_2$;
  each Y and Y' is independently selected from the group consisting of —(C($R^2$)$_2$)$_p$—, —$NR^2$—, —(C($R^2$)$_2$)$_p$—M—, >C=C($R^2$)$_2$, and —N($R^2$)—CH$_2$—;
  each $R^1$ is independently selected from the group consisting of hydrogen; $R^6$; $C_1$–$C_6$ alkyl; $C_2$–$C_6$ alkenyl; $C_2$–$C_6$ alkynyl; $C_3$–$C_6$ cycloalkyl optionally fused with $R^6$; $C_5$–$C_6$ cycloalkenyl optionally fused with $R^6$; and where $R^1$'s are attached to adjacent atoms, the $R^1$'s together with their attached adjacent atoms form a carbocyclic or heterocyclic ring system which may be optionally fused with $R^6$; where any member of $R^1$ may be optionally substituted by one or more $R^2$;
  each $R^2$ is independently selected from hydrogen; $R^3$; $C_1$–$C_6$ alkyl; $C_2$–$C_6$ alkenyl; $C_2$–$C_6$ alkynyl; $C_3$–$C_6$ cycloalkyl optionally fused with $R^6$; $C_5$–$C_6$ cycloalkenyl optionally fused with $R_6$; and where two $R^2$'s are attached to the same geminal atom, the $R^2$'s together with their attached geminal atom may form a spirocarbocyclic or spiroheterocyclic ring system; where any member of $R^2$ may be optionally substituted by one or more $R^3$;
  each $R^3$ is independently selected from oxo, $OR^9$, $N(R^9)_2$, $N(R^9)$—X—$R^9$, $N(R^9)$—X—$OR^9$, $N(R^9)$—X—$N(R^9)_2$, $SR^9$, X—$R^9$, O—X—$N(R^9)_2$, C(O)$N(R^9)_2$, halogen, $NO_2$, CN, $COOR^9$ and $R^6$;
  each $R^4$ is independently selected from from the group consisting of $OR^9$; $N(R^9)_2$; X—$R^9$; C(O)$N(R^9)_2$; $R^6$; $C_1$–$C_6$ alkyl; $C_2$–$C_4$ alkenyl; $C_3$–$C_6$ cycloalkyl optionally fused with $R^6$; $C_5$–$C_6$ cycloalkenyl optionally fused with $R^6$; where any member of $R^4$ may be optionally substituted by one or more groups independently selected from the group consisting of $R^9$ and $R^3$;

each $R^5$ is independently selected from the group consisting of H, OH, O and $R^1$;
  each $R^6$ is independently selected from the group consisting of aryl, carbocyclyl and heterocyclyl, wherein said aryl, carbocyclyl or heterocyclyl may be optionally substituted with one or more groups selected from the group consisting of oxo, —$OR^9$, —$R^9$, —$N(R^9)(R^9)$, —$N(R^9)$—X—$R^9$, $SR^9$, —X—$R^9$, —O—X—$N(R^9)_2$, —$R^9$—$OR^9$, —CN, —$CO_2R^9$, —X—$N(R^9)(R^9)$, halogen, —$NO_2$, and —$CF_3$;
  each $R^7$ is independently selected from the group consisting of hydrogen, OH and O;
  each $R^8$ is independently selected from the group consisting of hydrogen, alkyl, alkenyl, alkynyl, aryl, carbocyclyl, and heterocyclyl;
  each $R^9$ is independently selected from the group consisting of hydrogen, alkyl, alkenyl, alkynyl, aryl, carbocyclyl, heterocyclyl, aralkyl, carbocyclylalkyl and heterocyclylalkyl wherein any aryl, carbocyclyl or heterocyclyl may be optionally fused with $R^8$ and wherein any member of $R^8$ may be optionally substituted by one or more groups independently selected from the group consisting of —$OR^8$, —$N(R^8)_2$, —CN, —$NO_2$, —X—$R^8$, —X—$N(R^8)_2$, —C(O)$OR^8$, —$N(R^8)$—$XNR^8$, and halogen;
  each Q is independently selected from CH and N;
  each M is independently selected from the group consisting of NH, —$NR^2$—, —O—, —S—, —S(O)— and —S(O)$_2$—;
  each n is 1 or 2;
  each r is 0,1 or 2;
  each p is independently 1 or 2;
  each q is independently 1, 2 or 3; and
  each G is independently selected from the group consisting of —NH—, —$NR^2$—, —O—, —S—, —S(O)—, S(O)$_2$, —C(O)—, and —C($R^2$)$_2$—.}

It is also an object of this invention to provide pharmaceutical compositions comprising the compounds of formula I and methods for their use as inhibitors of aspartyl protease, and particularly, HIV aspartyl protease.

It is a further object of this invention to provide methods for treating viral diseases, and in particular HIV-related diseases, using the compounds and compositions of this invention.

DETAILED DESCRIPTION OF THE INVENTION

In order that the invention herein described may be more fully understood, the following detailed description is set forth. In the description, the following abbreviations are used:

| Designation | Reagent or Fragment |
| --- | --- |
| Ac | acetyl |
| Me | methyl |
| Et | ethyl |
| Bn | benzyl |
| Trityl | triphenylmethyl |
| Asn | D- or L-asparagine |
| Ile | D- or L-isoleucine |
| Phe | D- or L-phenylalanine |
| Val | D- or L-valine |

-continued

| Designation | Reagent or Fragment |
| --- | --- |
| Boc | tert-butoxycarbonyl |
| Cbz | benzyloxycarbonyl (carbobenzyloxy) |
| Fmoc | 9-fluorenylmethoxycarbonyl |
| DCC | dicyclohexylcarbodiimide |
| DIC | diisopropylcarbodiimide |
| EDC | 1-(3-dimethylaminopropyl)-3-ethylcarbodiimide hydrochloride |
| HOBt | 1-hydroxybenzotriazole |
| HOSU | 1-hydroxysuccinimide |
| TFA | trifluoroacetic acid |
| DIEA | diisopropylethylamine |
| DBU | 1,8-diazabicyclo (5.4.0) undec-7-ene |
| EtOAc | ethyl acetate |
| t-Bu | tert-butyl |
| iBu | iso-butyl |
| DME | dimethylformamide |
| THP | tertrahydropyran |
| THF | tetrahydrofuran |
| DMSO | dimethylsulfoxide |

The following terms are employed herein:

Unless expressly stated to the contrary, the terms "—$SO_2$—" and "—$S(O)_2$—" as used herein refer to a sulfone or sulfone derivative (i.e., both appended groups linked to the S), and not a sulfinate ester.

The term "alkoxy" refers to an alkyl ether radical, wherein the term "alkyl" is as defined above. Examples of suitable alkyl ether radicals include, but are not limited to, methoxy, ethoxy, n-propoxy, isopropoxy, n-butoxy, isobutoxy, sec-butoxy, tert-butoxy and the like.

The term "alkyl", alone or in combination with any other term, refers to a straight-chain or branch-chain saturated aliphatic hydrocarbon radical containing the specified number of carbon atoms, or where no number is specified, preferably from 1–10 and more preferably from 1–5 carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "alkenyl", alone or in combination with any other term, refers to a straight-chain or branched-chain mono- or poly-unsaturated aliphatic hydrocarbon radical containing the specified number of carbon atoms, or where no number is specified, preferably from 2–10 carbon atoms and more preferably, from 2–6 carbon atoms. Examples of alkenyl radicals include, but are not limited to, ethenyl, E- and Z-propenyl, isopropenyl, E- and Z-butenyl, E- and Z-isobutenyl, E- and Z-pentenyl, E- and Z-hexenyl, E,E-, E,Z-, Z,E- and Z,Z-hexadienyl and the like.

The term "anti-viral agent" or "anti-retroviral agent" refers to a compound or drug which possesses viral inhibitory activity. Such agents include reverse transcriptase inhibitors (including nucleoside and non-nucleoside analogs) and protease inhibitors. Preferably the protease inhibitor is an HIV protease inhibitor. Examples of nucleoside analog reverse transcriptase inhibitors include, but are not limited to, zidovudine (AZT), dideoxycytidine (ddC), didanosine (ddI), stavudine (d4T), 3TC, 935U83, 1592U89 and 524W91. Examples of non-nucleoside analog reverse transcriptase inhibitor include, but are not limited to TIBO, delavirdine (U90) and nevirapine. Examples of HIV protease inhibitors include, but are not limited to VX-478 (Vertex, also known as 141W94 (Glaxo-Wellcome) and KVX-478 (Kissei)), saquinavir (Ro 31-8959, Roche), indinavir (L-735,524, Merck)), ritonavir (ABT 538, Abbott), nelfinavir (AG 1343, Agouron), palinavir (Bila 2011 BS), U-103017 (Upjohn), XM 412 (DuPont Merck), XM 450 (DuPont Merck), BMS 186318 (Bristol-Meyers Squibb), CPG 53,437 (Ciba Geigy), CPG 61,755 (Ciba Geigy), CPG 70,726 (Ciba Geigy), ABT 378 (Abbott), GS 3333 (Gilead Sciences), GS 3403 (Gilead Sciences), GS 4023 (Gilead Sciences), GS 4035 (Gilead Sciences), GS 4145 (Gilead Sciences), GS 4234 (Gilead Sciences), and GS 4263 (Gilead Sciences).

The term "aryl", alone or in combination with any other term, refers to a carbocyclic aromatic radical (such as phenyl or naphthyl) containing the specified number of carbon atoms, preferably from 6–14 carbon atoms, and more atoms. Examples 6–10 carbon atoms. Examples of aryl radicals include, but are not limited to phenyl, naphthyl, indenyl, indanyl, azulenyl, fluorenyl, anthracenyl and the like.

The term "carbocycle" and "carbocyclyl" radical, refers to a non-aromatic stable 3- to 8-membered carbon ring which may be saturated, mono-unsaturated or poly-unsaturated. The carbocycle may be attached at any endocyclic carbon atom which results in a stable structure. Preferred carbocycles have 5–6 carbons.

The term "heterocycle" and "heterocyclyl" radical, unless otherwise defined herein, refers to a stable 3–7 membered monocyclic heterocyclic ring or 8–11 membered bicyclic heterocyclic ring which is either saturated or unsaturated, and which may be optionally benzofused if monocyclic. Each heterocycle consists of one or more carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. In addition, any ring nitrogen may be optionally substituted with a substituent $R^2$, as defined herein for compounds of formula I. A heterocyclyl radical may be attached at any endocyclic carbon or heteroatom which results in the creation of a stable structure. Preferred heterocycles include 5–7 membered monocyclic heterocycles and 8–10 memebered bicyclic heterocycles. Preferred heterocycles defined above include, for example, benzimidazolyl, imidazolyl, imidazolinoyl, imidazolidinyl, quinolyl, isoquinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, β-carbolinyl, tetrazolyl, thiazolidinyl, benzofuranoyl, thiamorpholinyl sulfone, oxazolyl, benzoxazolyl, oxopiperidinyl, oxopyrroldinyl, oxoazepinyl, azepinyl, isoxazolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl and sulfolanyl, dioxanyl, dioxolanyl, tetrahydrofurodihydrofuranyl, tetrahydropyranodihydrofuranyl, dihydropyranyl, tetrahydrofurofuranyl and tetrahydropyranofuranyl.

The term "halogen" refers to a radical of fluorine, chlorine, bromine or iodine.

The terms "HIV protease" and "HIV aspartyl protease" are used interchangeably and refer to the aspartyl protease encoded by the human immunodeficiency virus type 1 or 2. In a preferred embodiment of this invention, these terms refer to the human immunodeficiency virus type 1 aspartyl protease.

The term "substituted", whether preceded by the term "optionally" or not, and substitutions contained in formulas of this invention, refer to the replacement of one or more hydrogen radicals in a given structure with the radical of a specified substituent. When more than one position in a given structure may be substituted with more than one substituent selected from a specified group, the substituents may be either the same or different at every position (for example, the moiety —N($R^2$)($R^2$)). Typically, when a structure may be optionally substituted, 0–3 substitutions are preferred, and 0–1 substitutions is more preferred. Most preferred substituents are those which enhance protease inhibitory activity or intracellular antiviral activity in permissive mammalian cells or immortalized mammalian cell lines, or which enhance deliverability by enhancing solubility characteristics or enhancing pharmacokinetic or pharmacodynamic profiles as compared to the unsubstituted compound. Other more preferred substituents include those used in the compounds shown in Tables 1–5.

The term "pharmaceutically effective amount" refers to an amount effective in treating HIV infection in a patient either as monotherapy or in combination with other agents. The term "treating" as used herein refers to the alleviation of symptoms of a particular disorder in a patient or the improvement of an ascertainable measurement associated with a particular disorder. Specifically, with respect to HIV, effective treatment using the compounds and compositions of this invention would result in an improvement in an HIV associated ascertainable measurement. The term "prophylactically effective amount" refers to an amount effective in preventing HIV infection in a patient. As used herein, the term "patient" refers to a mammal, including a human.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the antiretroviral agent.

As used herein, the compounds of this invention, including the compounds of formula I are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention or an inhibitorily active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicylic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium), alkaline earth metal (e.g., magnesium), ammonium and N—($C_{1-4}$ alkyl)$_4^+$ salts.

The term "thiocarbamates" refers to compounds containing the functional group N—$SO_2$—O.

The compounds of this invention contain one or more asymmetric carbon atoms and thus occur as racemates and racemic mixtures, single enantiomers, diastereomeric mixtures and individual diastereomers. All such isomeric forms of these compounds are expressly included in the present invention. Each stereogenic carbon may be of the R or S configuration. Although the specific compounds exemplified in this application may be depicted in a particular stereochemical configuration, compounds having either the opposite stereochemistry at any given chiral center or mixtures thereof are also envisioned.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a mammal or for use in affinity chromatography applications). Typically, such compounds are stable at a temperature of 40° C. or less, in the absence of moisture or other chemically reactive conditions, for at least a week.

The compounds of the present invention may be used in the form of salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

This invention also envisions the quaternization of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

The compounds of this invention are those of formula I:

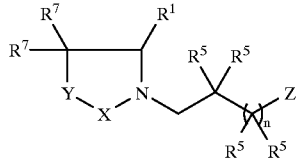
(I)

wherein
each Z is

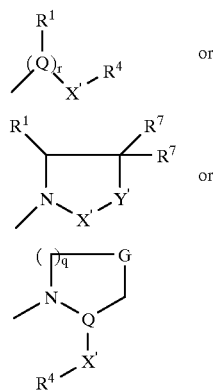
or wherein any Z may be optionally fused with $R^6$;

each X and X' is independently selected from the group consisting of —C(O)—, —C(O)C(O)—, —S(O)— and —S(O)$_2$;

each Y and Y' is independently selected from the group consisting of —(C(R$^2$)$_2$)$_p$—, —NR$^2$—, —(C(R$^2$)$_2$)$_p$—M—, >C=C(R$^2$)$_2$, and —N(R$^2$)—CH$_2$—;

each $R^1$ is independently selected from the group consisting of hydrogen; $R^6$; C$_1$–C$_6$ alkyl; C$_2$–C$_6$ alkenyl; C$_2$–C$_6$ alkynyl; C$_3$–C$_6$ cycloalkyl optionally fused with $R^6$; C$_5$–C$_6$ cycloalkenyl optionally fused with $R^6$; and where $R^1$'s are attached to adjacent atoms, the $R^1$'s together with their attached adjacent atoms form a carbocyclic or heterocyclic ring system which may be optionally fused with $R^6$; where any member of $R^1$ may be optionally substituted by one or more $R_2$;

each $R^2$ is independently selected from hydrogen; $R^3$; C$_1$–C$_6$ alkyl; C$_2$–C$_6$ alkenyl; C$_2$–C$_6$ alkynyl; C$_3$–C$_6$ cycloalkyl optionally fused with $R^6$; C$_5$–C$_6$ cycloalkenyl optionally fused with $R^6$; and where two $R^2$'s are attached to the same geminal atom, the $R^2$'s together with their attached geminal atom may form a spirocarbocyclic or spiroheterocyclic ring system; where any member of $R^2$ may be optionally substituted by one or more $R^3$;

each $R^3$ is independently selected from oxo, OR$^9$, N(R$^9$)$_2$, N(R$^9$)—X—R$^9$, N(R$^9$)—X—OR$^9$, N(R$^9$)—X—N(R$^9$)$_2$, SR$^9$, X—R$^9$, O—X—N(R$^9$)$_2$, C(O)N(R$^9$)$_2$, halogen, NO$_2$, CN, COOR$^9$ and R$^6$;

each $R^4$ is independently selected from from the group consisting of OR$^9$; N(R$^9$)$_2$; X—R$^9$; C(O)N(R$^9$)$_2$; R$^6$; C$_1$–C$_6$ alkyl; C$_2$–C$_4$ alkenyl; C$_3$–C$_6$ cycloalkyl optionally fused with $R^6$; C$_5$–C$_6$ cycloalkenyl optionally fused with $R^6$; where any member of $R^4$ may be optionally substituted by one or more groups independently selected from the group consisting of $R^9$ and $R^3$, each $R^5$ is independently selected from the group consisting of H, OH, O and $R^1$;

each $R^6$ is independently selected from the group consisting of aryl, carbocyclyl and heterocyclyl, wherein said aryl, carbocyclyl or heterocyclyl may be optionally substituted with one or more groups selected from the group consisting of oxo, —OR$^9$, —R$^9$, —N(R$^9$)(R$^9$), —N(R$^9$)—X—R$^9$, SR$^9$, —X—R$^9$, —O—X—N(R$^9$)$_2$, —R$^9$—OR$^9$, —CN, —CO$_2$R$^9$, —X—N(R$^9$)(R$^9$), halogen, —NO$_2$, and —CF$_3$;

each $R^7$ is independently selected from the group consisting of hydrogen, OH and O each $R^8$ is independently selected from the group consisting of hydrogen, alkyl, alkenyl, alkynyl, aryl, carbocyclyl, and heterocyclyl;

each $R^9$ is independently selected from the group consisting of hydrogen, alkyl, alkenyl, alkynyl, aryl, carbocyclyl, heterocyclyl, aralkyl, carbocyclylalkyl and heterocyclylalkyl wherein any aryl, carbocyclyl or heterocyclyl may be optionally fused with $R^8$ and wherein any member of $R^8$ may be optionally substituted by one or more groups independently selected from the group consisting of —OR$^8$, —N(R$^8$)$_2$, —CN, —NO$_2$, —X—R$^8$—X—N(R$^8$)$_2$, —C(O)OR$^8$, —N(R$^8$)—XNR$^8$, and halogen;

each Q is independently selected from CH and N;

each M is independently selected from the group consisting of NH, —NR$^2$—, —O—, —S—, —S(O)— and —S(O)$_2$—;

each n is 1 or 2;

each r is 0,1 or 2;

each p is independently 1 or 2;

each q is independently 1, 2 or 3; and each G is independently selected from the group consisting of —NH—, —NR$^2$—, —O—, —S—, —S(O)—, S(O)$_2$, —C(O)—, and —C(R$^2$)$_2$—.

Except where expressly noted to the contrary, the term "[variable] as defined for formula I" refers to the definitions shown directly above. In addition, where no reference is made to a particular definition for a given variable, the definition is to be taken as that defined for formula I shown directly above.

Preferred compounds of formula I are those wherein each Y and Y' is independently selected from the group consisting of —(C(R$^2$)$_2$)$_p$—, —NR$^2$—, —(C(R$^2$)$_2$)$_p$—M—, and —N(R$^2$)—CH$_2$—; and each $R^3$ is independently selected from oxo, OR$^9$, N(R$^9$)$_2$, N(R$^9$)—X—R$^9$, N(R$^9$)—X—OR$^9$, SR$^9$, X—R$^9$, O—X—N(R$^9$)$_2$, C(O)N(R$^9$)$_2$, halogen, NO$_2$, CN, COOR$^9$ and R$^6$.

Alternate preferred compounds of formula I are those having the structure of formula IA:

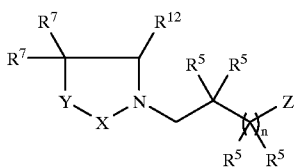

(IA)

wherein each $R^{12}$ is independently selected from the group consisting of $R^6$; $C_1$–$C_6$ alkyl optionally substituted with $R^6$; $C_2$–$C_6$ alkenyl; $C_2$–$C_6$ alkynyl; $C_3$–$C_6$ cycloalkyl optionally fused with $R^6$; $C_5$–$C_6$ cycloalkenyl optionally fused with $R^6$; where any member of $R^{12}$ may be optionally substituted by one or more $R^2$.

Preferred compounds of formula I are those wherein n is equal to 1; those having the structure of formula II:

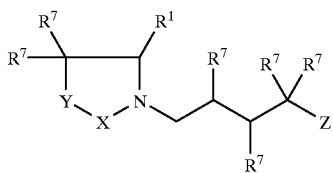

(II)

and those having the structure of formula III:

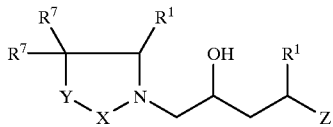

(III)

Also preferred are compounds according to formula I wherein X is —C(O)— or —S(O)$_2$— and Y is —(C(R$^2$)$_2$)$_p$—M—; those wherein X is —C(O)— or —S(O)$_2$— and Y is (—C(R$^2$)$_2$—)$_p$; those wherein X is —C(O)—, —C(O)C(O)— or —S(O)$_2$—; and Y is —N(R$^2$)— or —N(R$^2$)—CH$_2$—; those having the structure of formula IV:

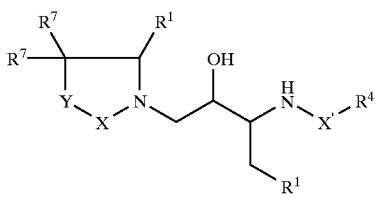

(IV)

wherein

X and X' are independently —C(O)— or —S(O)$_2$—; and Y is —(C(R$^2$)$_2$)—M—, —(C(R$^2$)$_2$)$_p$—, —N(R$^2$)— or —N(R$^2$)—CH$_2$—.

Also preferred are those compounds of formula I having the structure of formula V:

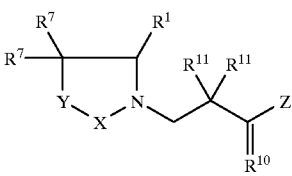

(V)

wherein

X is —C(O)— or —S(O)$_2$—;
Y is —(C(R$^2$)$_2$)—M—, —(C(R$^2$)$_2$)$_p$—, —N(R$^2$)— or —N(R$^2$)—CH$_2$—;
$R^{10}$ is O or H$_2$;
each $R^{11}$ is independently H, OH or O, where both $R^{11}$ may not simultaneously be hydrogen; and
Z is a structure of formula VI:

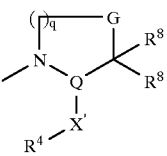

(VI)

wherein any structure of formula VI may be optionally fused with an aryl, carbocyclic or heterocyclic ring and may be optionally substituted with 1–3 substituents independently selected from $R^2$;

compounds having the structure of formula V, wherein
  $R^{10}$ and $R^{11}$ are O;
compounds having the structure of formula V, wherein
  $R^{10}$ and $R^{11}$ are O;
  q is 1;
  G is S; and
  X' is —C(O)—;
compounds having the structure of formula V, wherein
  $R^{10}$ and $R^{11}$ are O;
  q is 1;
  G is S;
  X' is —C(O)—; and
  $R^4$ is t-butylamino;
compounds having the structure of formula V, wherein
  $R^{10}$ and $R^{11}$ are O;
  X is —C(O)—;
  Y is —(C(R$^2$)$_2$)$_p$—; and
  $R^7$ is H;
compounds having the structure of formula V wherein
  X and X' is —C(O)—;
  Y is —(C(R$^2$)$_2$)—;
  $R^7$ is H;
  $R^{10}$ is H$_2$; and
  one $R^{11}$ is H and one $R^{11}$ is OH;
those compounds of formula V wherein
  X and X' is —C(O)—;
  Y is —N(R$^2$)—;
  $R^7$ is H;
  $R^{10}$ is H$_2$; and
  one $R^{11}$ is H and one $R^{11}$ is OH; and those compounds of formula V wherein
X and X' is —C(O)—;
Y is —(C(R²)₂)—M—;
M is O;
R⁷ is H;
R¹⁰ is H₂; and
one R¹¹ is H and one R¹¹ is OH.

Also preferred is the compound of formula I having the structure of formula IX:

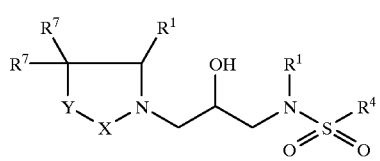

(IX)

wherein
X is —C(O)— or —S(O)₂—; and the compounds of formula IX wherein
X is —C(O)—;
Y is —(C(R²)₂)—M—; and
R⁷ is H; and those compounds of formula IX wherein
X is —C(O)—;
Y is —N(R²)—; and
R⁷ is H; and those compounds of formula IX wherein
X is —C(O)—; Y is —(C(R²)₂)—; and R⁷ is H.

Also preferred are those compounds of formula I having the structure of formula XII:

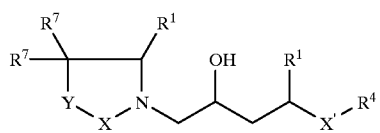

(XII)

wherein
X and X' are independently —C(O)— or —S(O)₂—; those compounds of formula I having the structure of formula XII, wherein
X and X' are independently —C(O)— or —S(O)₂—; and R⁴ is 1-amino-2-hydroxyindanyl; and compounds of formula I having the structure of formula XII, wherein R⁴ is 1(S)-amino-2(R)-hydroxyindanyl.

Also preferred are the compounds according to formula I, having the structure of formula XIII:

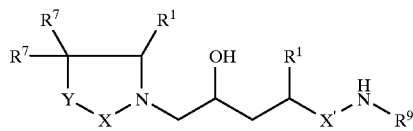

(XIII)

wherein
X and X' are independently —C(O)— or —S(O)₂—; compounds according formula I having the structure of formula XIII, wherein
X is —C(O)— or —S(O)₂—;
X' is —C(O)—;.

Y is —(C(R²)₂)— or —N(R²)—; and
R⁷ is H;
compounds of formula I having the structure of formula XIII, wherein
X is —C(O)—;
X' is —C(O)—;
Y is —(C(R²)₂)—; and
R⁷ is H;
compounds of formula I having the structure of formula XIII, wherein
X is —C(O)—;
X' is —C(O)—;
Y is —N(R²)—; and
R⁷ is H;
compounds of formula I having the structure of formula XIII, wherein
X is —SO₂—;
X' is —C(O)—;
Y is —(C(R²)₂)—; and
R⁷ is H; and
compounds of formula I having the structure of formula XIII, wherein
X is —SO₂—;
X' is —C(O)—;
Y is —N(R²)—; and
R⁷ is H.

In an alternate embodiment, preferred compounds are those of formula V wherein
R¹⁰ is H₂; and
one R¹¹ is H and one R¹¹ is OH; and
Z is selected from the group consisting of:

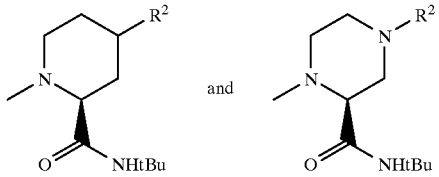

and R² is as defined in formula I; and those of formula V wherein Z is selected from the group consisting of

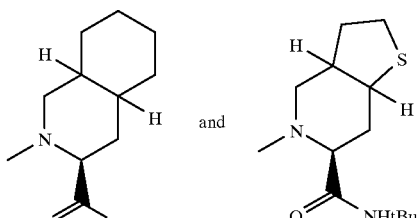

R¹⁰ is H₂; and
one R¹¹ is H and one R¹¹ is OH.

Also preferred are those compounds of formula V wherein
X and X' is —C(O)—;
Y is —(C(R²)₂)—;
R⁷ is H;
R¹⁰ is H₂; and
one R¹¹ is H and one R¹¹ is OH; and those compounds of formula V wherein X and X' is —C(O)—;
Y is —N(R²)—;
R⁷ is H;
R¹⁰ is H₂; and
one R¹¹ is H and one R¹¹ is OH, and those compounds of formula V, wherein X and X' is —C(O)—;
Y is —(C(R²)₂)—M—;
M is O;
R⁷ is H;
R¹⁰ is H₂; and
one R¹¹ is H and one R¹¹ is OH, and the aforementioned compounds of formula V wherein Z is selected from the group consisting of:

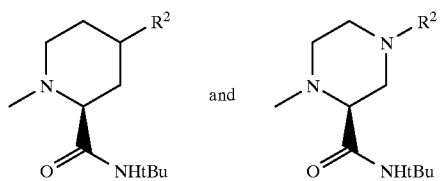

and R² is as defined in claim 1.

Also preferred are those compounds of formula V wherein X and X' is —C(O)—;

Y is —(C(R²)₂)—;
R⁷ is H;
R¹⁰ is H₂; and
one R¹¹ is H and one R¹¹ is OH; and those compounds of formula V wherein
X and X' is —C(O)—;
Y is —N(R²)—;
R⁷ is H;
R¹⁰ is H₂; and
one R¹¹ is H and one R¹¹ is OH, and those compounds of formula V, wherein X and X' is —C(O)—;
Y is —(C(R²)₂)—M—;
M is O;
R⁷ is H;
R¹⁰ is H₂; and
One R¹¹ is H and one R¹¹ is OH, and the aforementioned compounds of formula V wherein Z is selected from the group consisting of:

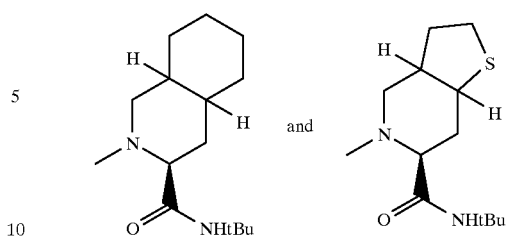

Also preferred are compounds of formula I wherein
Z is selected from the group consisting of —XR⁴, —N(R¹)—X—R⁴, —N(R¹)—N(R¹)—X—R⁴, and formula VI; wherein any structure of formula VI may be optionally fused with an aryl, carbocyclic or heterocyclic ring and may be optionally substituted with 1–3 members independently selected from R².

In another embodiment, compounds of formula I with structures VII, VIII, IX, and X are preferred:

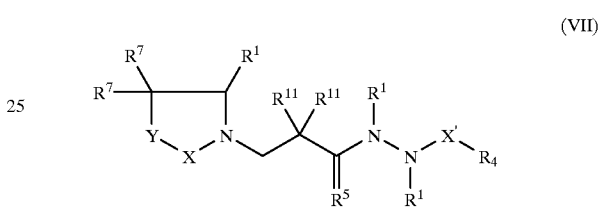

(VII)

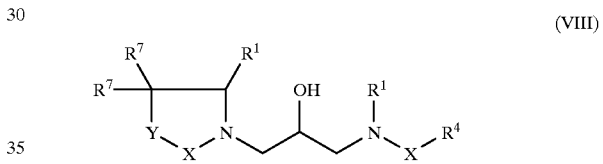

(VIII)

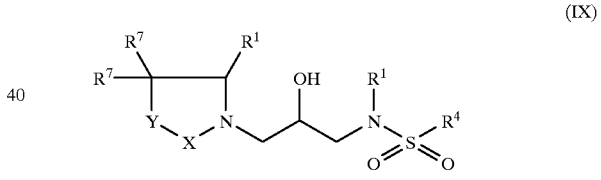

(IX)

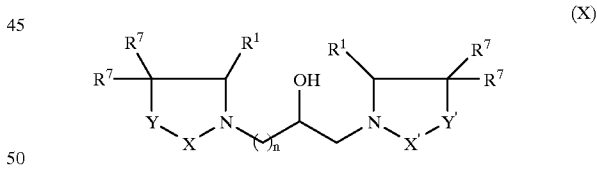

(X)

where all definitions of variables for formula I apply.

Preferred R² groups for formula I include: C₁–C₆ alkyl and alkenyl optionally substituted with R⁶; where two R² taken together form a spriocyclic ring and C₃–C₆ cycloalkyl or cycloalkenyl optionally fused with R⁶.

Preferred compounds of this invention of formula I include the specific compounds contained in Tables 1–5.

TABLE 1
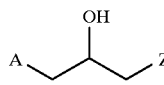
| Cmpd. No. | A | Z |
|---|---|---|
| 1 | 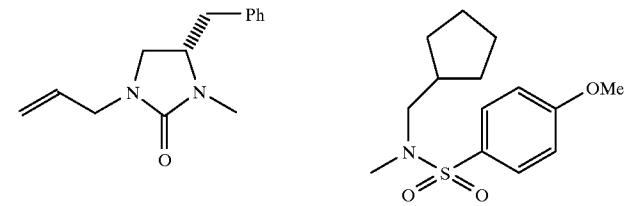 | 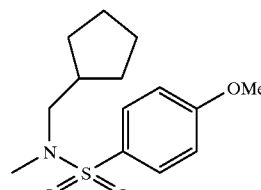 |
| 2 | 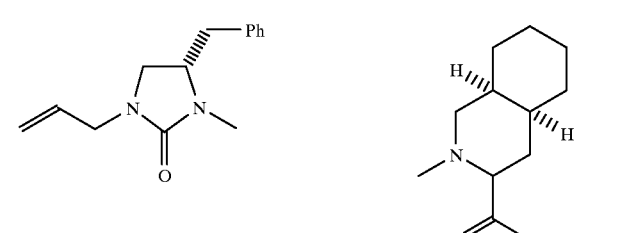 | 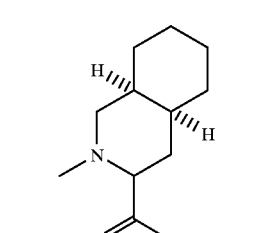 |
| 3 | 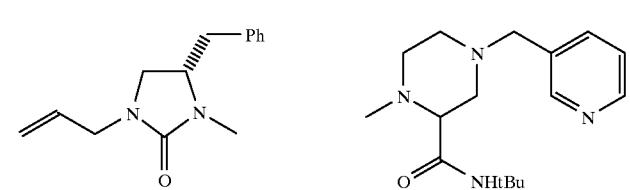 | 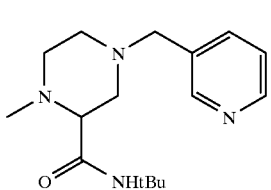 |
| 4 | 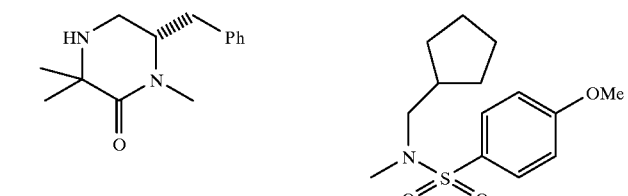 | 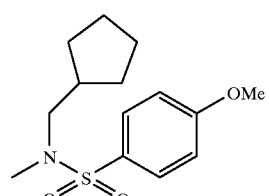 |
| 5 | 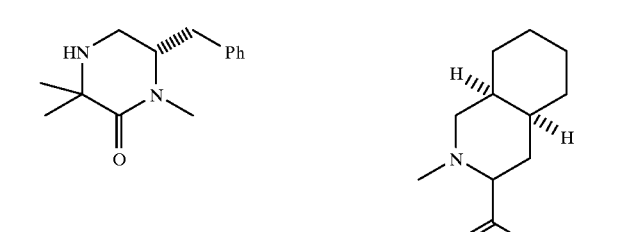 | 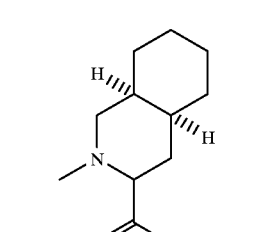 |
| 6 | 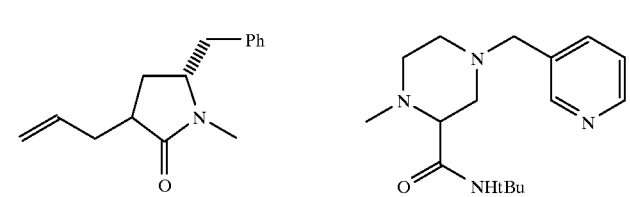 | 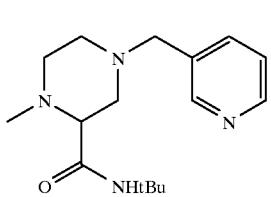 |

TABLE 1-continued
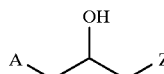
| Cmpd. No. | A | Z |
|---|---|---|
| 7 | 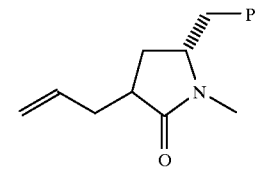 | 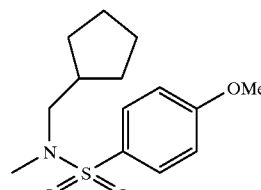 |
| 8 | 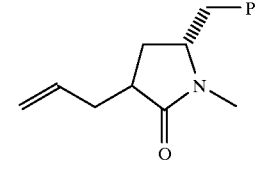 | 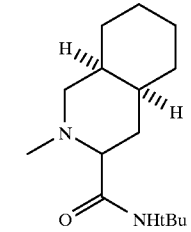 |
| 9 | 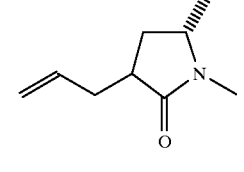 | 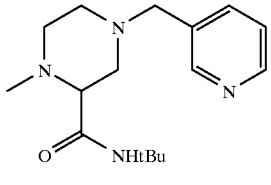 |
| 10 | 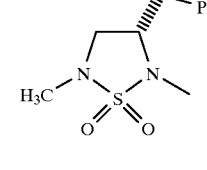 | 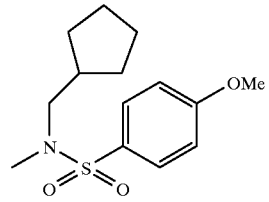 |
| 11 | 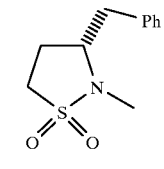 | 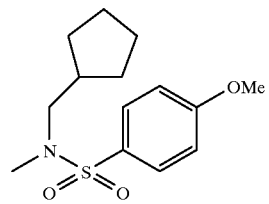 |
| 12 | 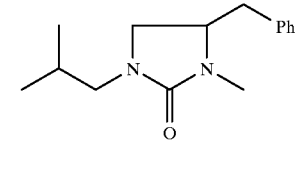 | 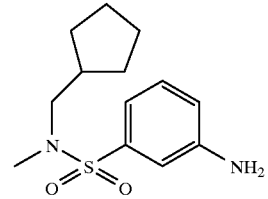 |

TABLE 1-continued
| Cmpd. No. | A | Z |
|---|---|---|
| 13 | 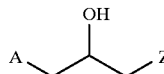 | 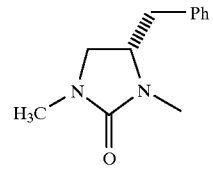 |
| 14 | 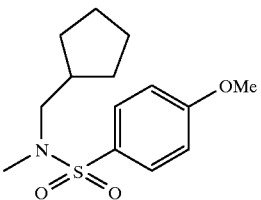 | 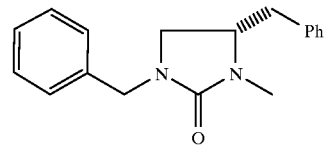 |
| 15 |  | 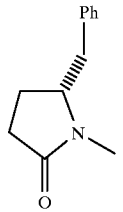 |
| 16 | 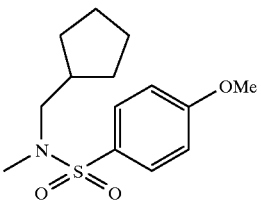 | 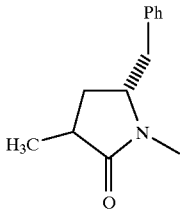 |
| 17 | 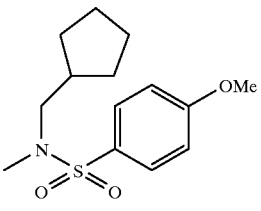 | 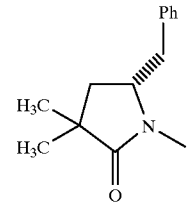 |
| 18 | 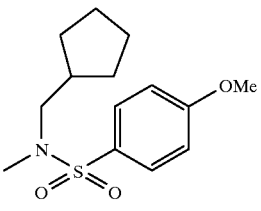 | 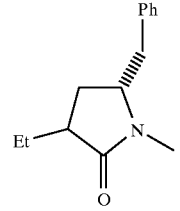 |

TABLE 1-continued
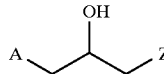
| Cmpd. No. | A | Z |
|---|---|---|
| 19 | 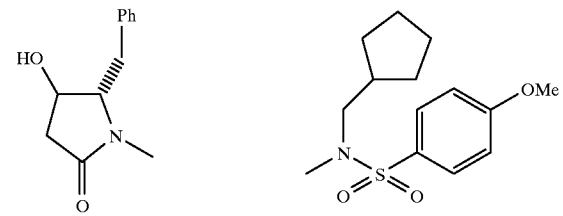 | 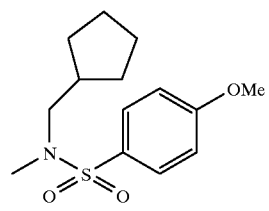 |
| 20 | 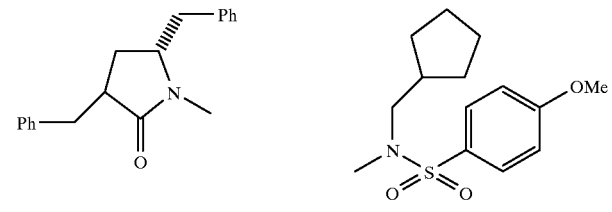 | 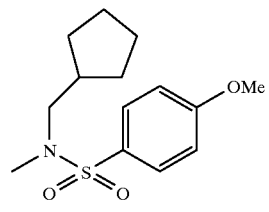 |
| 21 | 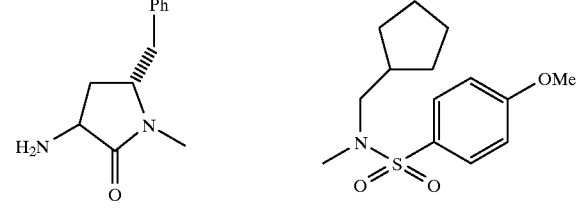 | 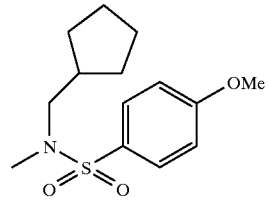 |
| 22 | 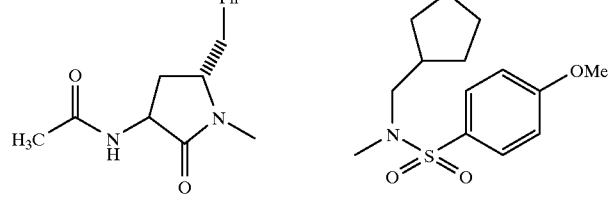 | 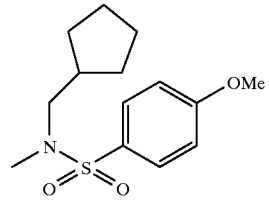 |
| 23 | 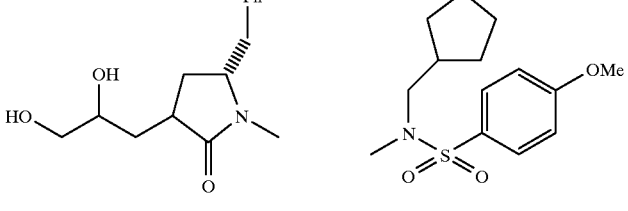 | 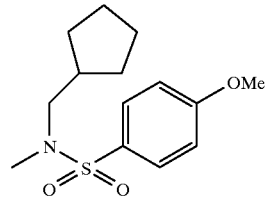 |
| 24 | 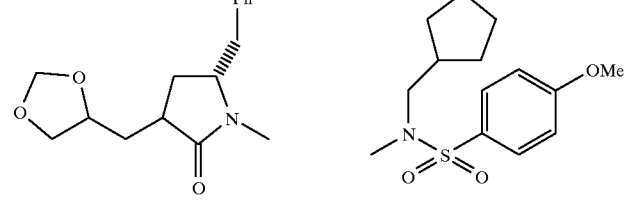 | 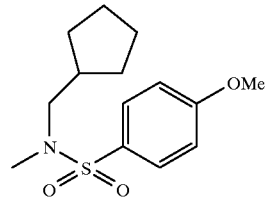 |

TABLE 1-continued
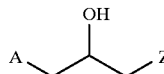
| Cmpd. No. | A | Z |
|---|---|---|
| 25 | 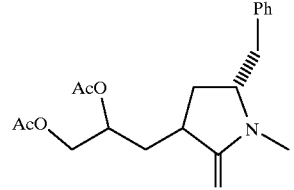 | 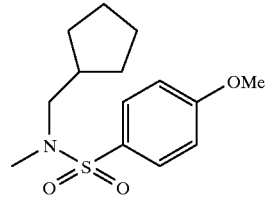 |
| 26 | 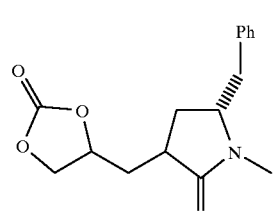 | 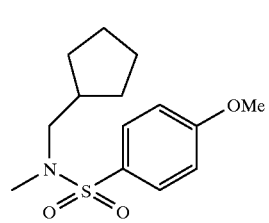 |
| 27 | 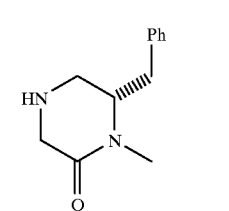 | 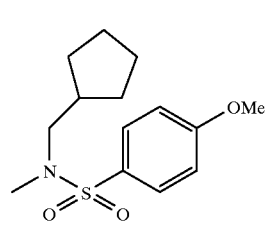 |
| 28 | 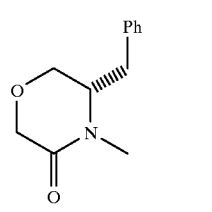 | 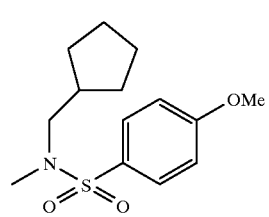 |
| 29 | 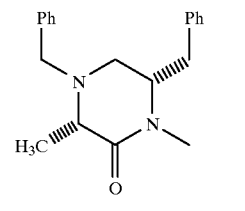 | 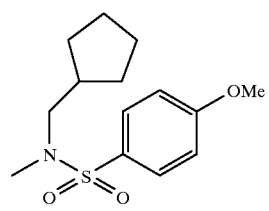 |
| 30 | 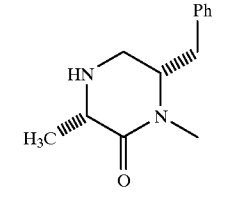 | 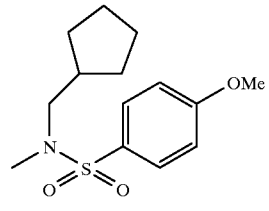 |

TABLE 1-continued
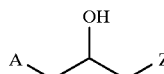
| Cmpd. No. | A | Z |
|---|---|---|
| 31 | 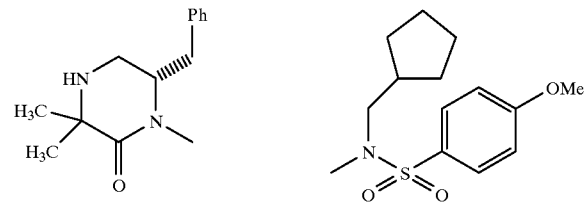 | 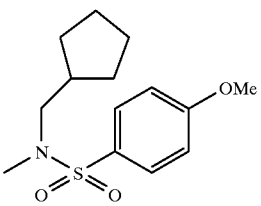 |
| 32 | 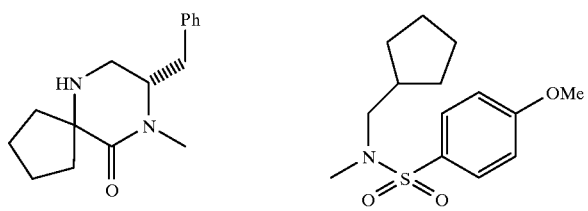 | 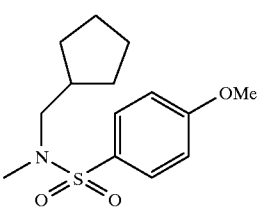 |
| 33 | 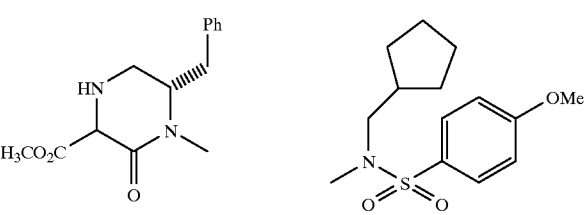 | 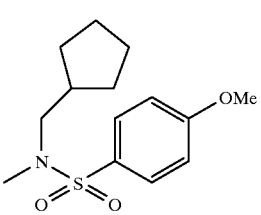 |
| 34 | 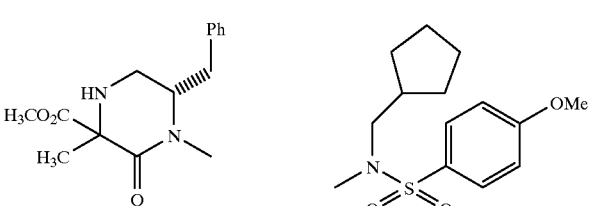 | 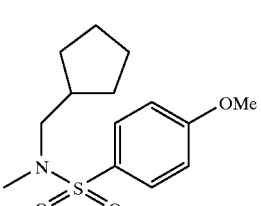 |
| 35 | 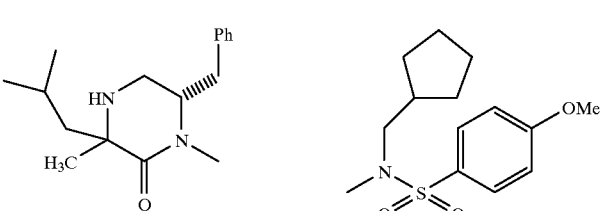 |  |
| 36 | 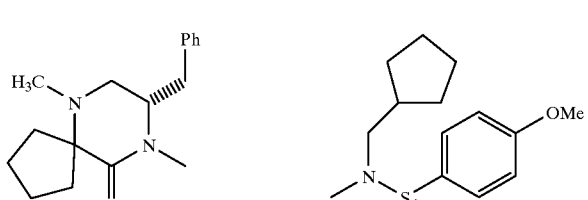 |  |

TABLE 1-continued
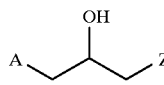
| Cmpd. No. | A | Z |
|---|---|---|
| 37 | 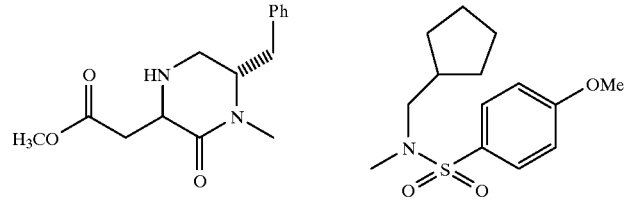 | 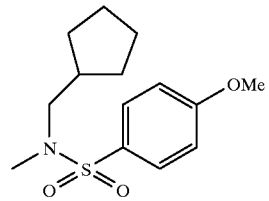 |
| 38 | 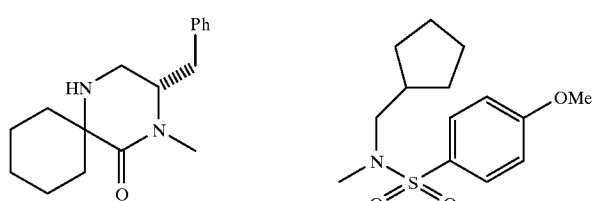 | 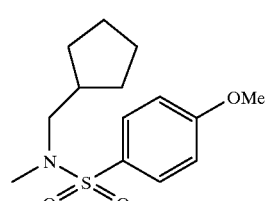 |
| 39 | 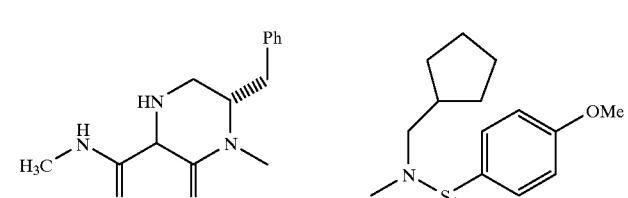 | 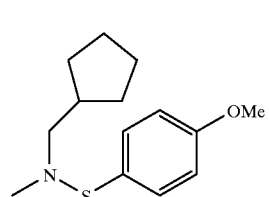 |
| 40 | 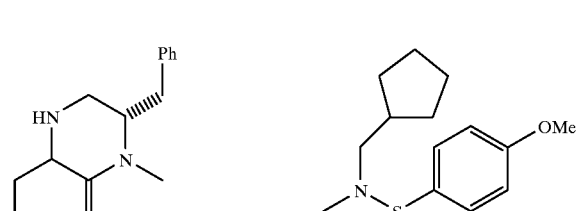 | 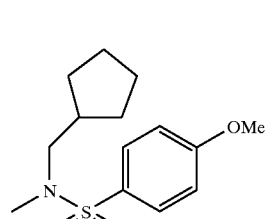 |
| 41 | 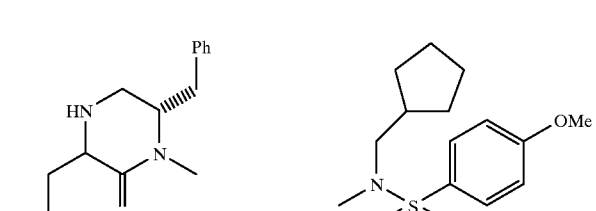 | 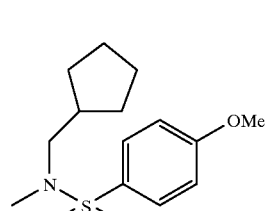 |
| 42 | 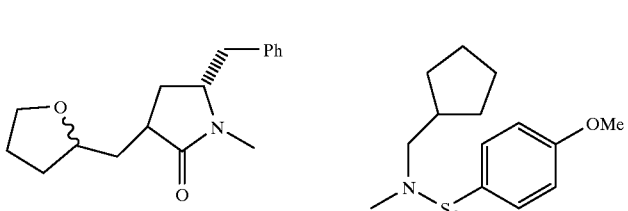 | 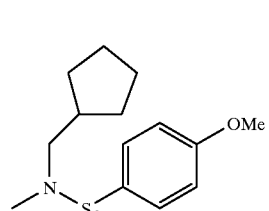 |

TABLE 1-continued
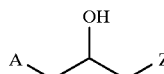
| Cmpd. No. | A | Z |
|---|---|---|
| 43 | 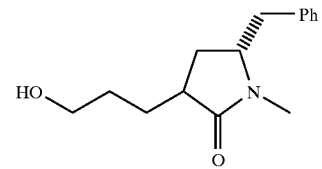 | 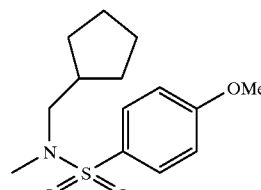 |
| 44 | 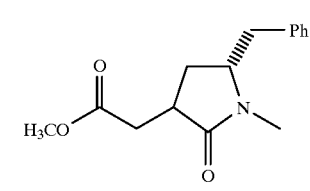 | 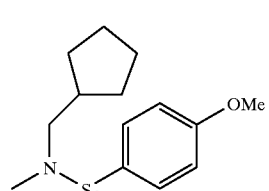 |
| 45 | 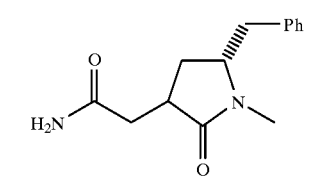 | 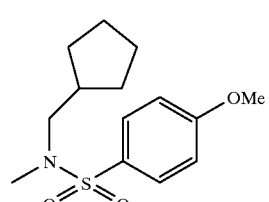 |
| 46 | 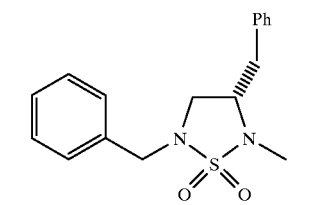 | 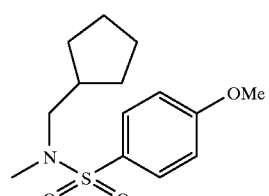 |
| 47 | 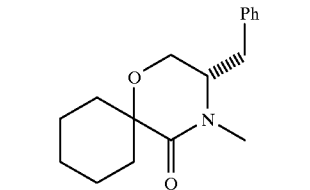 | 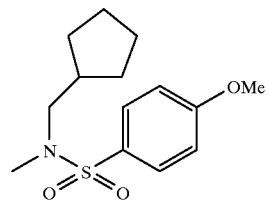 |
| 48 | 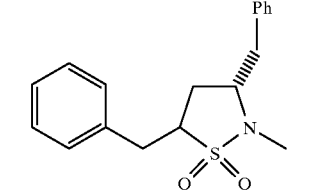 | 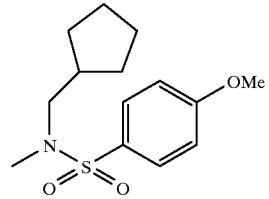 |

TABLE 1-continued
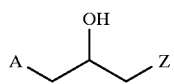

TABLE 1-continued
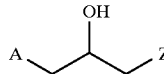
| Cmpd. No. | A | Z |
|---|---|---|
| 55 | 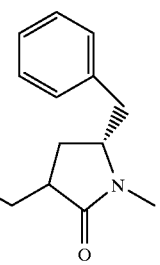 | 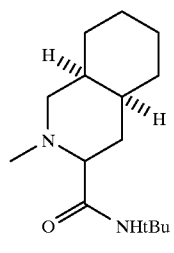 |
| 56 | 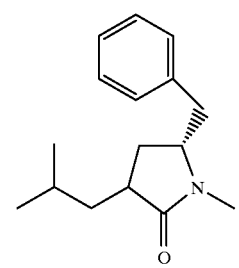 | 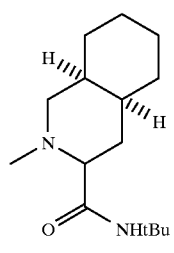 |
| 57 | 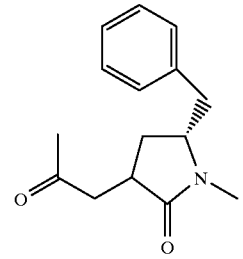 | 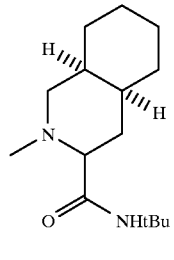 |
| 58 | 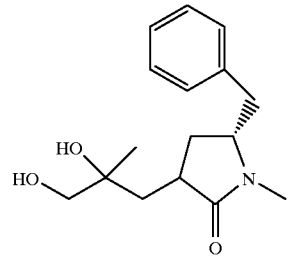 | 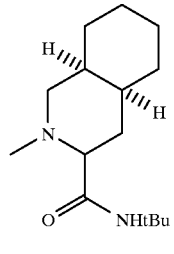 |
| 59 | 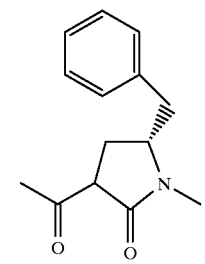 | 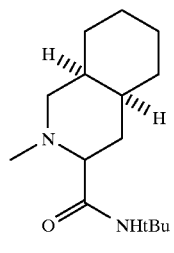 |

TABLE 1-continued
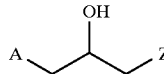
| Cmpd. No. | A | Z |
|---|---|---|
| 60 | 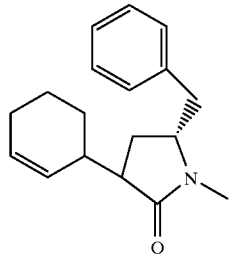 | 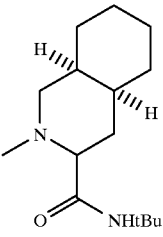 |
| 61 | 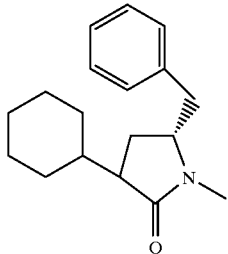 | 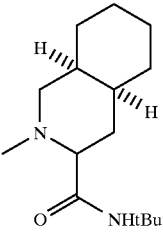 |
| 62 | 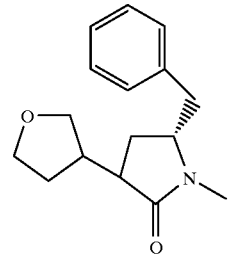 | 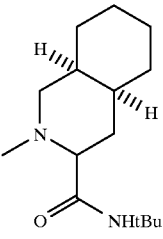 |
| 63 | 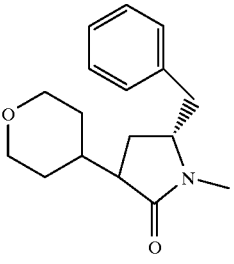 | 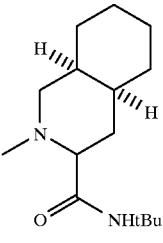 |
| 64 | 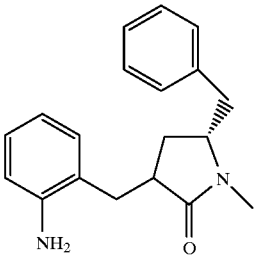 | 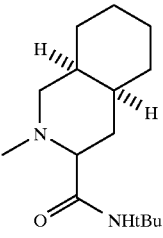 |

TABLE 1-continued $$A\diagdown\underset{OH}{\diagup}\diagdown Z$$

| Cmpd. No. | A | Z |
|---|---|---|
| 65 | (3-benzyl-1-methyl-2-oxo-4-(furan-3-ylmethylene)pyrrolidinyl) | (N-methyl-decahydroisoquinoline-3-carboxamide, NHtBu) |
| 66 | (5-benzyl-1-methyl-2-oxo-3-(2-(N-benzyl-N-Boc-amino)ethyl)pyrrolidinyl) | (N-methyl-decahydroisoquinoline-3-carboxamide, NHtBu) |
| 67 | (5-benzyl-1-methyl-2-oxo-3-(2-(BocNH)ethyl)pyrrolidinyl) | (N-methyl-decahydroisoquinoline-3-carboxamide, NHtBu) |
| 68 | (5-benzyl-1-methyl-2-oxo-3-(2-(benzylamino)ethyl)pyrrolidinyl) | (N-methyl-decahydroisoquinoline-3-carboxamide, NHtBu) |
| 69 | (5-benzyl-1-methyl-2-oxo-3-(tetrahydrofuran-3-ylmethyl)pyrrolidinyl) | (N-methyl-decahydroisoquinoline-3-carboxamide, NHtBu) |

TABLE 1-continued
| Cmpd. No. | A | Z |
|---|---|---|
| 70 | 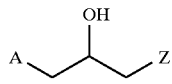 | 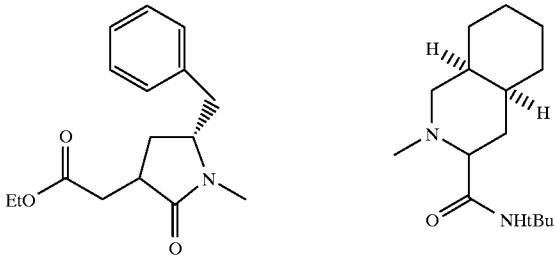 |
| 71 | 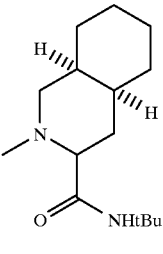 | 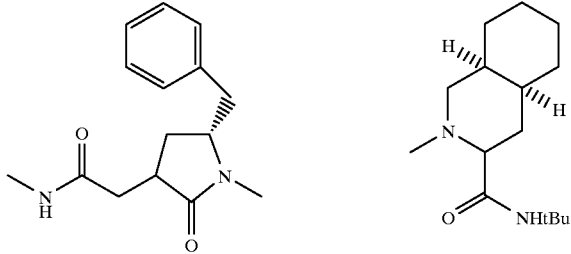 |
| 72 | 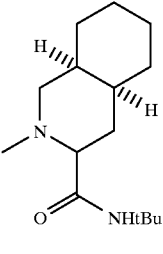 | 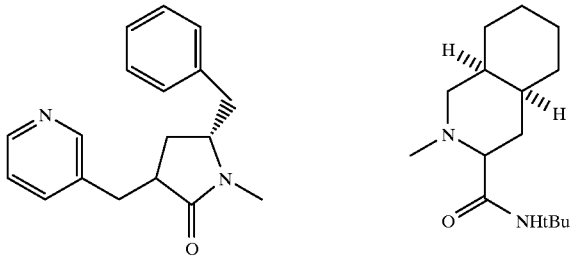 |
| 73 | 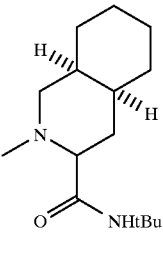 | 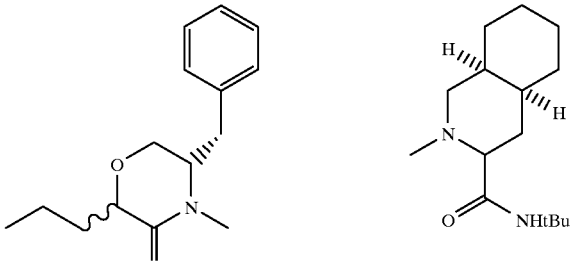 |
| 74 | 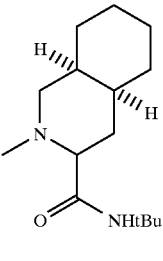 | 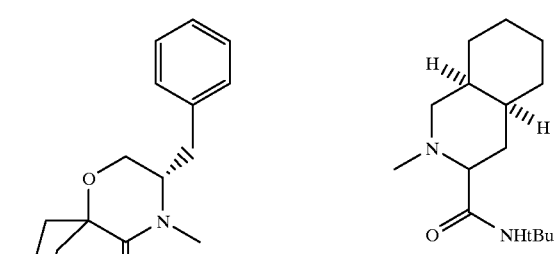 |

TABLE 1-continued
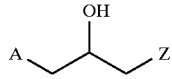
| Cmpd. No. | A | Z |
|---|---|---|
| 75 | | |
| 76 | | |
| 77 | | |
TABLE 2
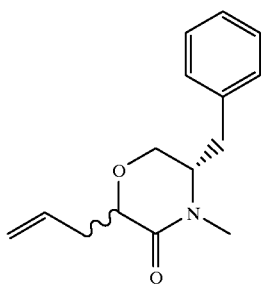
| Compd. No. | A | R¹ | Z |
|---|---|---|---|
| 78 | | Bn | |

TABLE 2-continued
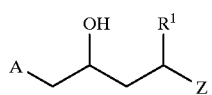
| Compd. No. | A | R¹ | Z |
|---|---|---|---|
| 79 | 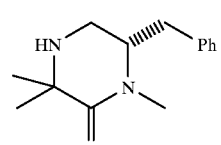 | Bn | 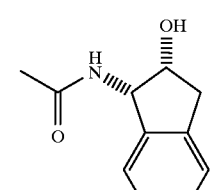 |
| 80 | 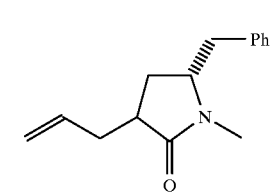 | Bn | 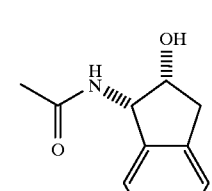 |
| 81 | 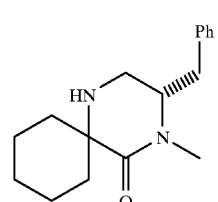 | Bn | 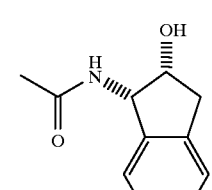 |
| 82 | 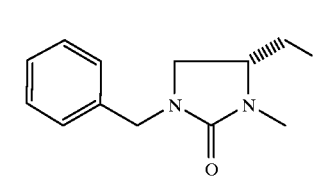 | Bn | 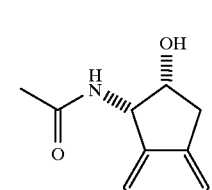 |
| 83 | 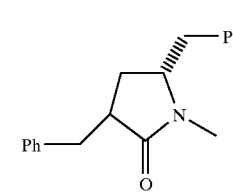 | Bn | 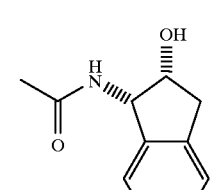 |
| 84 | 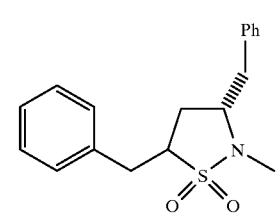 | Bn | 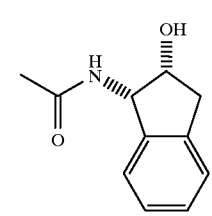 |

TABLE 2-continued $$\underset{A}{\overset{OH}{\diagup}}\underset{Z}{\overset{R^1}{\diagup}}$$

| Compd. No. | A | R¹ | Z |
| --- | --- | --- | --- |
| 85 | (5-benzyl-1-methyl-pyrrolidin-2-one) | Bn | N-acetyl-2-hydroxy-indanyl |
| 86 | (5-benzyl-1-methyl-3-propyl-pyrrolidin-2-one) | Bn | N-acetyl-2-hydroxy-indanyl |
| 87 | (5-benzyl-3-(cyclopentylmethyl)-1-methyl-pyrrolidin-2-one) | Bn | N-acetyl-2-hydroxy-indanyl |
| 88 | (5-benzyl-1-methyl-3-(tetrahydrofuran-3-ylmethyl)-pyrrolidin-2-one) | Bn | N-acetyl-2-hydroxy-indanyl |
| 89 | (5-benzyl-3-(furan-3-ylmethylene)-1-methyl-pyrrolidin-2-one) | Bn | N-acetyl-2-hydroxy-indanyl |

TABLE 2-continued
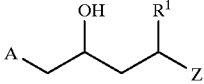
| Compd. No. | A | R[1] | Z |
|---|---|---|---|
| 90 |  | Bn | 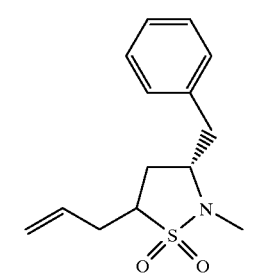 |
| 91 | 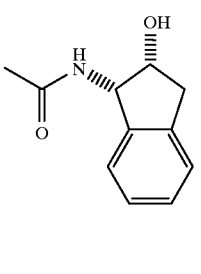 | Bn | 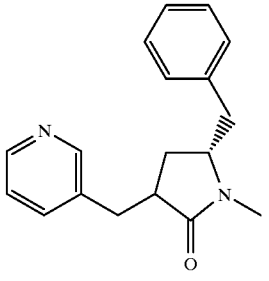 |
| 92 | 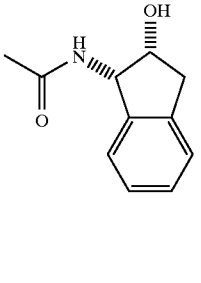 | Bn | 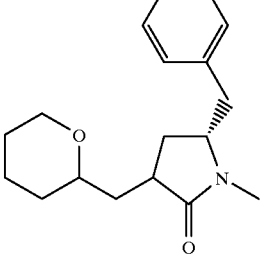 |
| 93 | 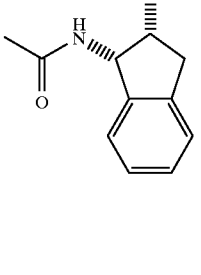 | Bn | 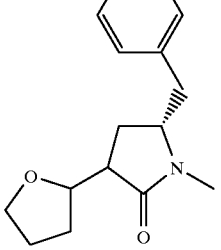 |
| 94 | 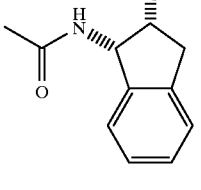 | Bn | |

TABLE 2-continued

| Compd. No. | A | R¹ | Z |
|---|---|---|---|
| 95 | (1-methyl-5-benzyl-3-(tetrahydropyran-4-yl)pyrrolidin-2-one) | Bn | N-acetyl-2-hydroxyindanyl |
| 96 | (1-methyl-5-benzyl-3-(cyanomethyl)pyrrolidin-2-one) | Bn | N-acetyl-2-hydroxyindanyl |

TABLE 3

| Cmpd No. | A | Z |
|---|---|---|
| 97 | (1-allyl-3-methyl-4-benzylimidazolidin-2-one) | (3-methylthiazolidine-4-carboxamide NHtBu) |
| 98 | (6,6-dimethyl-1-methyl-5-benzylpiperazin-2-one) | (3-methylthiazolidine-4-carboxamide NHtBu) |

TABLE 3-continued

| Cmpd No. | A | Z |
|---|---|---|
| 99 | (1-methyl-3-allyl-5-benzylpyrrolidin-2-one) | (3-methylthiazolidine-4-carboxamide NHtBu) |
| 100 | (spiro cyclohexyl piperazinone, N-methyl, benzyl) | (3-methylthiazolidine-4-carboxamide NHtBu) |

TABLE 3-continued
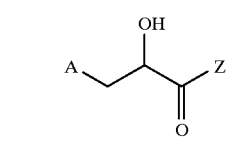
| Cmpd No. | A | Z |
|---|---|---|
| 101 | | |
| 102 | | |
| 103 | | |
TABLE 4
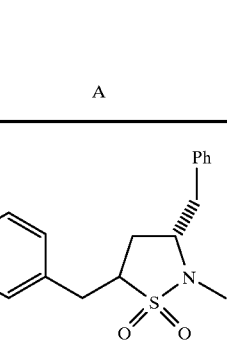
| Cmpd No. | A | Z |
|---|---|---|
| 104 | | |
| 105 | | |
| 106 | | |

TABLE 4-continued
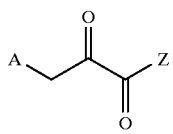
| Cmpd No. | A | Z |
| --- | --- | --- |
| 107 | 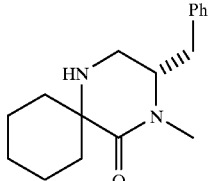 | 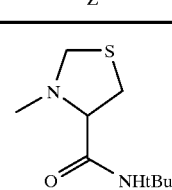 |
| 108 | 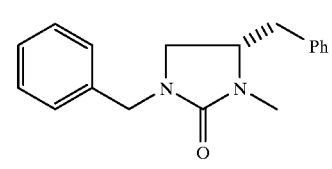 | 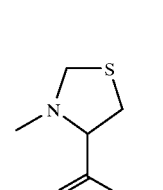 |
| 109 | 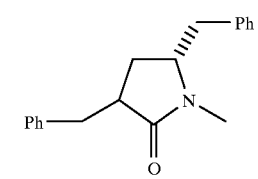 | 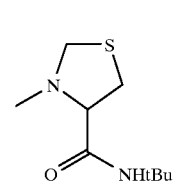 |
| 110 | 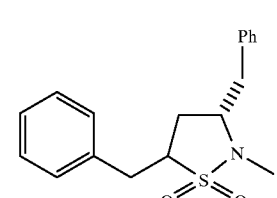 | 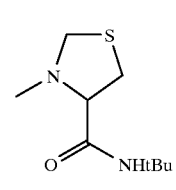 |
| 111 | 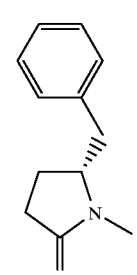 | 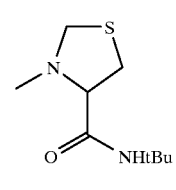 |
| 112 | 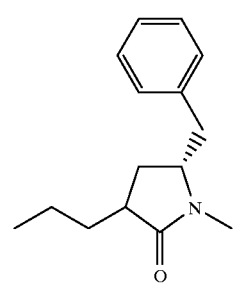 |  |

TABLE 4-continued

| Cmpd No. | A | Z |
|---|---|---|
| 113 | (4-benzyl-2-benzyl-5-methyl-1,2,5-thiadiazolidine 1,1-dioxide) | 3-methylthiazolidine-4-carboxamide N-tBu |
| 114 | (2-benzyl-3-methyl-5-propyl-oxazolidin-4-one) | 3-methylthiazolidine-4-carboxamide N-tBu |
| 115 | (5-benzyl-4-methyl-1-oxa-4-azaspiro[5.5]cyclohexane-3-one) | 3-methylthiazolidine-4-carboxamide N-tBu |

TABLE 5

| Cmpd No. | A | R¹ | Z |
|---|---|---|---|
| 116 | (1-allyl-3-methyl-4-benzyl-imidazolidin-2-one, CH₂Ph) | Bn | (tetrahydrofuran-2-yl methylcarbamate) |

TABLE 5-continued

| Cmpd No. | A | R¹ | Z |
|---|---|---|---|
| 117 | (structure: 2,2-dimethyl-piperazinone with benzyl substituent) | Bn | (carbamate-tetrahydrofuran structure) |
| 118 | (structure: 3-allyl-5-benzyl-1-methyl-pyrrolidinone) | Bn | (carbamate-tetrahydrofuran structure) |
| 119 | (structure: spirocyclohexane piperazinone with benzyl) | Bn | (carbamate-tetrahydrofuran structure) |
| 120 | (structure: 1-benzyl-3-methyl-4-benzyl-imidazolidin-2-one) | Bn | (carbamate-tetrahydrofuran structure) |
| 121 | (structure: 3-benzyl-5-benzyl-1-methyl-pyrrolidinone) | Bn | (carbamate-tetrahydrofuran structure) |
| 122 | (structure: 5-benzyl-3-benzyl-2-methyl-isothiazolidine-1,1-dioxide) | Bn | (carbamate-tetrahydrofuran structure) |

The preferred compounds of this invention are compound numbers (as in Tables 1–5): 1, 2, 3, 4, 7, 8, 9, 13, 14, 16, 17, 18, 20, 23, 24, 25, 26, 32, 35, 38, 44, 45, 46, 47, 48, 49, 50, 51, 52, 53, 54, 62, 63, 72, 75, 76, 78, 80, 82(59), 83(60), 91, 92, 94, 95, 96, 101(66), 102(67), 109, 121(81) and 122(82). More preferred are compound numbers: 2, 7, 8, 9, 14, 18, 20, 25, 26, 32, 38, 45, 47, 48, 49, 50, 51, 53, 54, 62, 63, 72, 82(59), 83(60), 91, 92, 94, 95 and 96. Even more preferred are compound numbers: 7, 8, 9, 20, 45, 50, 51, 53, 54, 82(59), 83(60), 92, 94 and 96.

The compounds of this invention may be synthesized using conventional techniques. Advantageously, these compounds are conveniently synthesized from readily available starting materials.

Although the syntheses of the compounds of this invention are known to those of skill in the art, the following general schemes are set forth to illustrate these methods. These schemes should not be viewed as limiting the scope of this invention in any way.

Using standard techniques, compounds of the present invention having the general formula I may be obtained as described in the following schemes:
SCHEME 1
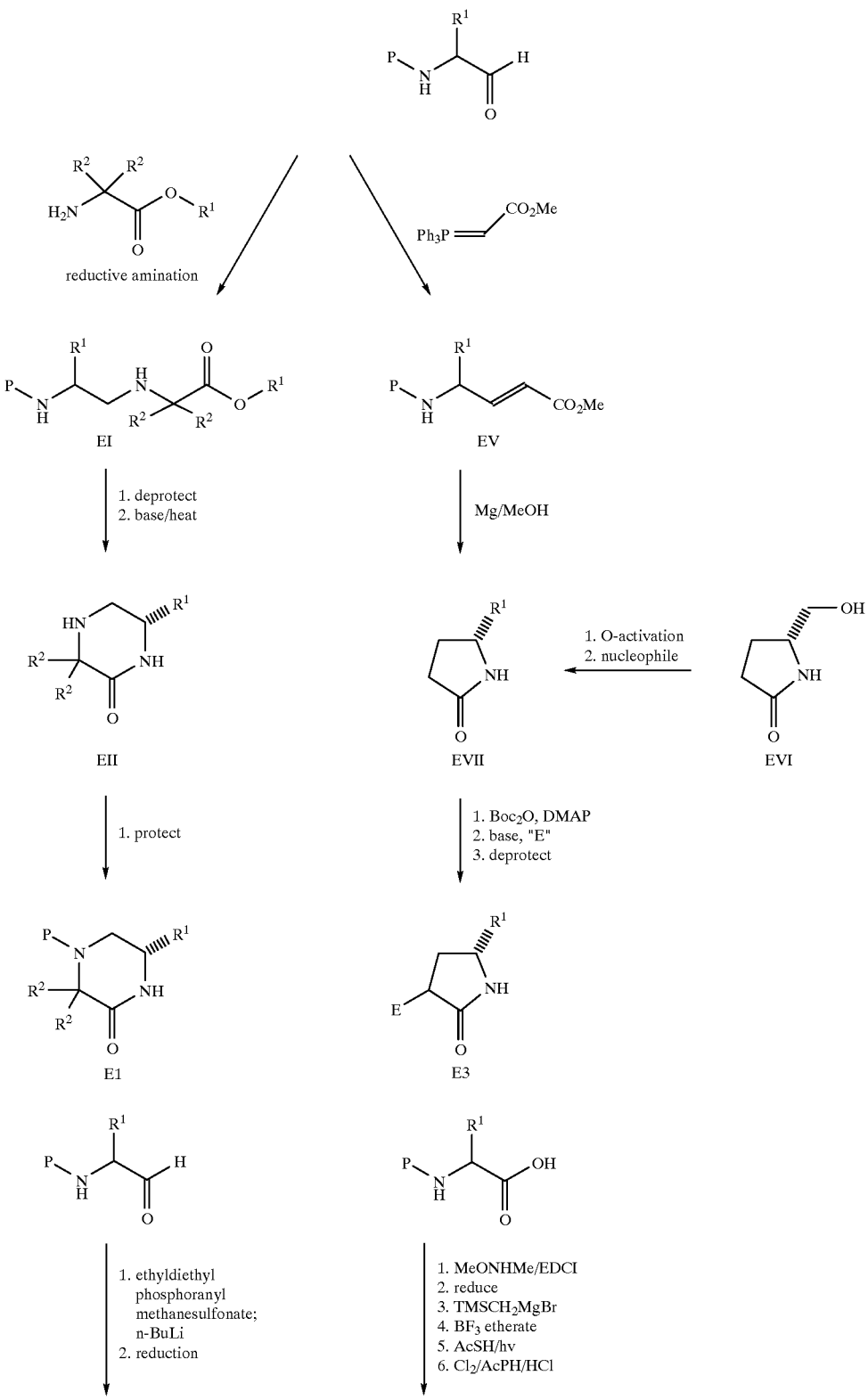

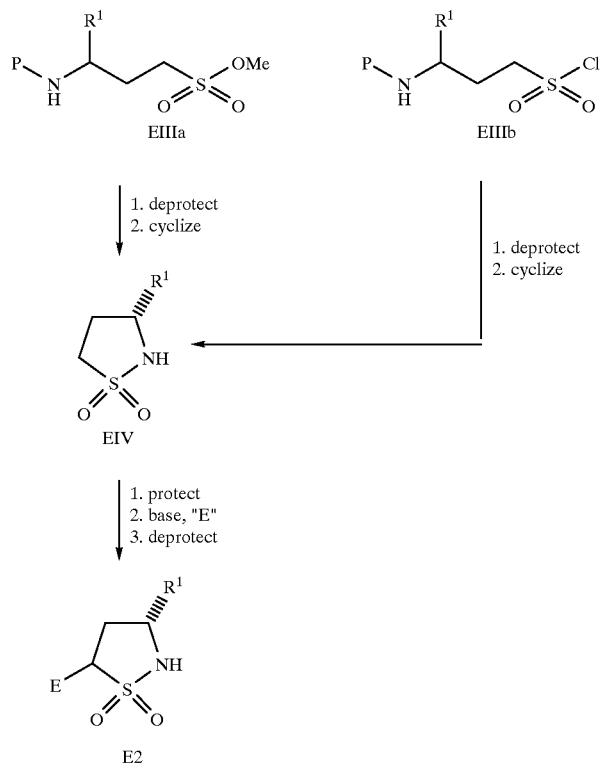
SCHEME 2
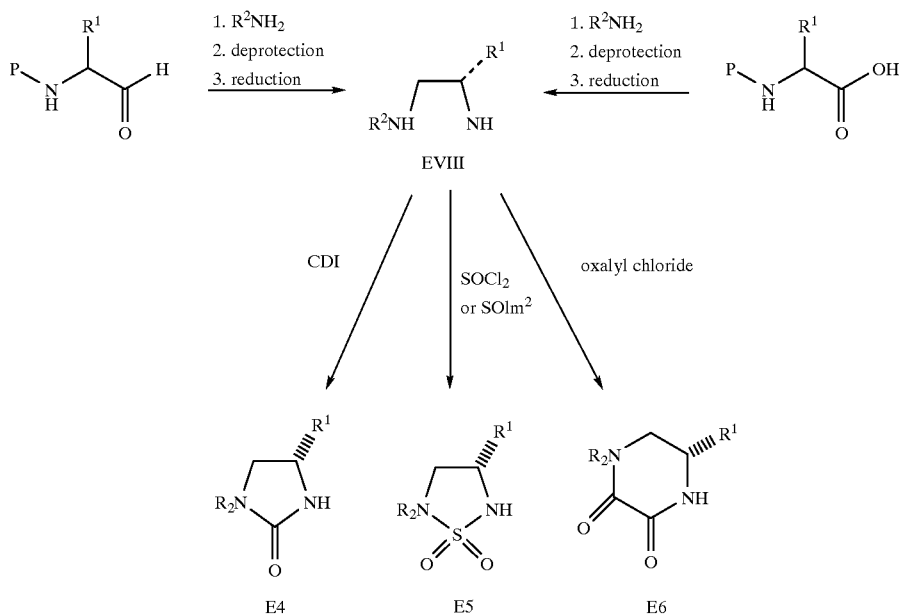

SCHEME 3
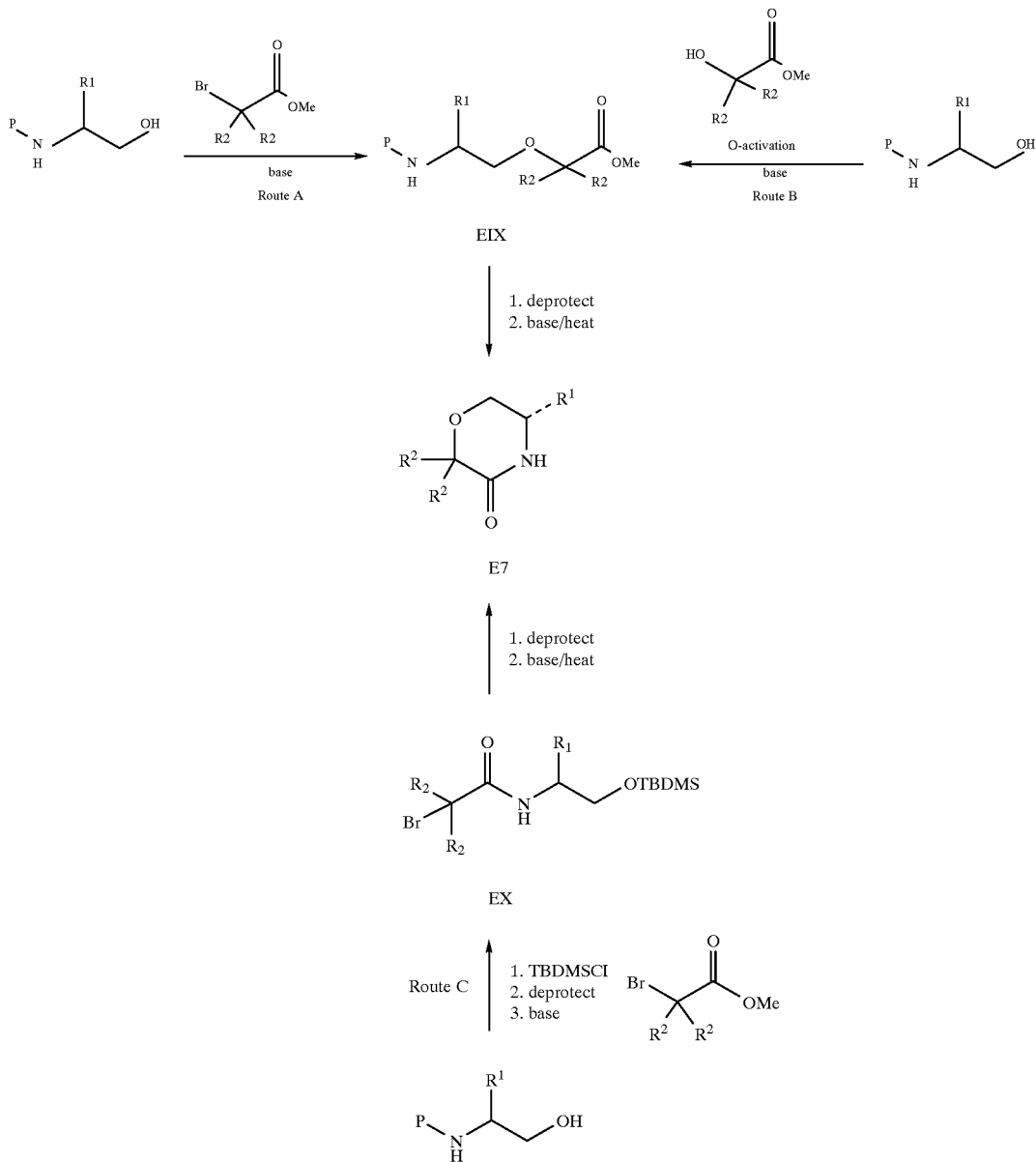
SCHEME IV
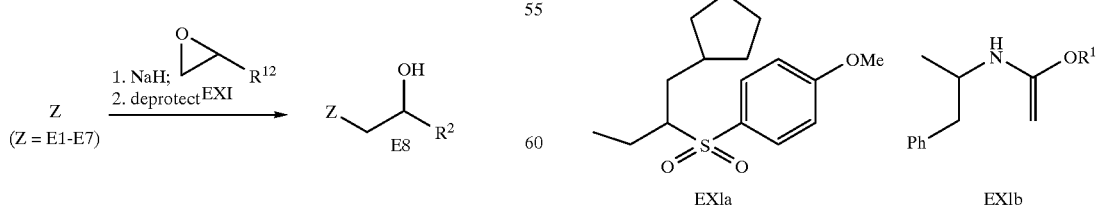

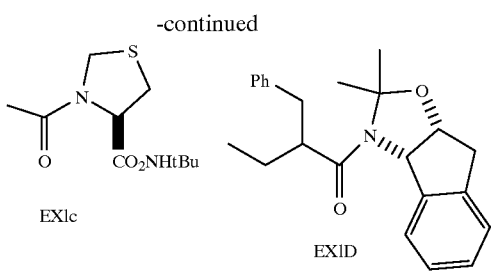

SCHEME 5

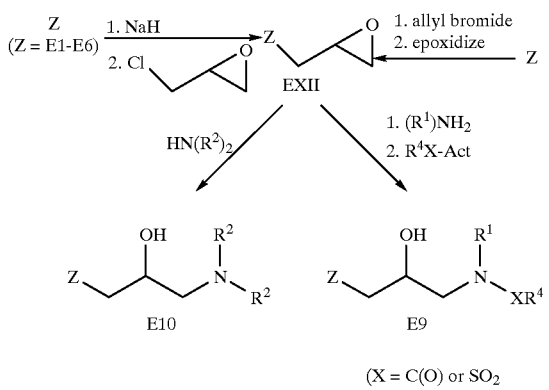

(X = C(O) or SO₂)

SCHEME 6

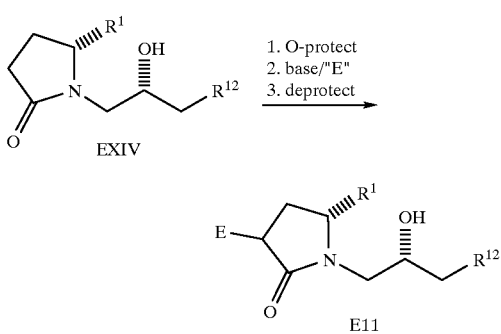

Methods for producing the compounds of this invention are well known in the art of organic synthesis. Several intermediates are commercially available, e.g. from Aldrich Chemical Company, Inc., Milwaukee, Wis. The synthesis of heterocycles E1–E6 (Schemes 1 and 2) begins with any protected amino aldehyde, the preparations for which are well known in the art from suitably protected amino acids, esters or alcohols. In the case of the this intermediate, transient protection of the amino group may be accomplished by means known in the art (see, e.g. T. W. Greene and P. G. M., Wuts "Protective Groups in Organic Synthesis", Second Edition, pp. 309–405 ©1991 John Wiley and Sons, Inc. New York, N.Y. and E. Gross and J. Meinhofer "The Peptides, Vol. 3: Protection of Functional Groups in Peptide Synthesis" pp. 3–88; ©1981 Academic Press, Inc. New York, N.Y). Carbamates such as Boc, Fmoc, Alloc and Cbz are particularly convenient protecting groups, the introduction and removal of are described in the above references.

The synthesis of E1 is iluustrated in Scheme 1. The protected amino aldehyde is treated with an alpha substituted or alpha, alpha disubstituted amino ester under typical reductive amination conditions well known in the art, such as sodium cyanoborohydride in a solvent mixture of DMF/Acetic acid. The resulting compound EI is then deprotected and free based with either a tertiary amine base or potassium carbonate in methanol to effect cyclization to form EII. The resulting secondary amine may the be protected with groups (detailed in the references above) such as benzyl or t-butyloxycarbonyl (Boc) utilizing conditions well known in the art to form analogs of E1.

Preparation of E2 is achieved by reaction of a starting aldehyde with ethyl diethylphosphoranylmethanesulfonate and subsequent reduction of the double bond (see: Gennari et al., *Angew. Chem. Int. Ed. Engl.*, 33, pp. 2067–69 (1994)) to yield compound EIIIa. Cyclization may then be achieved by deesterification and activation of the sulfonate moiety as described in Gennari, followed by deprotection of the nitrogen protection group to yield the cyclized product EIV. Alternatively, an amino acid may be converted to compound EIIIb using standard synthetic methods illustrated in Scheme 1. Compound EIIIb can be cyclized to afford compound EIV. Compound EIV may then be N-protected, for example, in the presence of Boc anhydride and DMAP (see: Flynn et al., *J. Org. Chem.* 48, pp. 2424–26 (1983)), and treated with a non-nucleophilic base such as LDA or hexamethyldisilazane to generate the anion at the center alpha to the $SO_2$ moiety. This anion may then be quenched with a variety of electrophiles and subsequently deprotected to form the desired analogs of E2. Analogously, preparation of E3 results from a Wittig reaction using methyl(triphenylposphoranylidene)acetate followed by simultaneous reduction of the double bond and cyclization using magnesium metal in methanol (Wei et al., *Tetrahedron Lett.*, 34(28), pp. 4439–42 (1993)). A similar N-protection, deprotonation, quench and N-deprotection scheme as described in the preparation of E2, results in desired analogs of E3. Alternatively, E3 may be prepared from commercially available EVI. The hydroxyl group may be activated using commonly available reagents such as methanesulfonyl chloride or para-toluenesulfonyl chloride in the presence of a tertiary amine base. The addition of a nucleophile to displace the mesylate or tosylate yields EVII (Ackermann et al., *Helv. Chim. Acta*, 73, pp. 122–32 (1990)) which may be treated as described above to obtain E3.

Methods for the preparation of compounds E4–E6 are also well known in the art and stem from readily available protected amino aldehydes. Treatment of these aldehydes with a variety of amines under reductive amination conditions well known in the art, such as sodium cyanoborohydride using DMF/Acetic acid as a solvent mixture, followed by deprotection of the primary amine yields diamine EVIII. Intramolecular cyclization with a variety of activated carbonyl, dicarbonyl or sulfuryl equivalents in the presence of a tertiary amine base yields compounds E4–E6. Examples of activating reagents include but are not limited to carbonyldiimidazole, phosgene, sulfuryldichloride, sulfuryldiimidazole, sulfonyl diimide, and oxalyl chloride.

Methods leading to the production of analogs of compound E7 are also known in the art (McManus et al., *J. Med. Chem.*, 8, pp. 766–76 (1965)). Scheme 3 exemplifies several potential routes to the synthesis of compound E7. Any protected amino alcohol may be deprotonated to form the alkoxide which may be reacted with a substituted alpha bromo ester to form ether EIX (route A). Alternatively (route B), EIX may be formed from activation of a protected amino alcohol with, for example, methanesulfonyl chloride or para-toluenesulfonyl chloride in the presence on a tertiary amine base and subsequent addition of a nucleophile such as an alkoxide from an alpha hydroxy acid to displace mesylate or tosylate to yield EIX. Compound EIX can then be deprotected, free based with a tertiary amine base or potassium carbonate in methanol, and heated to effect cyclization to form E7. Alternatively (route C), E7 may be prepared from a protected amino alcohol by protection of the hydroxyl group with, for example, t-butyldimethyl silyl chloride/imidazole to afford the silyl ether. Subsequent nitrogen deprotection and acylation with a alpha bromo acid in the presence of any number of available coupling agents (for example dicylcohexylcarbodiimide, other related carbodiimide reagents or isobutyl chloroformate) or acylation with an alpha bromo acid chloride provides compound EX. Desilylation using, for example, tetrabutylammonium formate in THF followed by formation of the alkoxide with base affords cyclization to E7.

Schemes 4–6 describe methods for converting the cyclic compounds E1–E7 into compounds of this invention. For example, compounds of the type Z, exemplified by compounds E1–E7, may be deprotonated and reacted with a functionalized epoxide to generate the desired compounds as described in Scheme 4. Several of the described epoxides are readily synthesized via methods well known in the art (Maligres et al, *Tetrahedron Lett.*, 36, pp. 2195–98 (1995)). Optionally, further modification of the compounds may be performed subsequent to epoxide opening using reactions and materials well known in the art. For example, subsequent to epoxide opening utilizing example EXIb deprotection of the carbamate allows further modification of the unmasked amine.

Alternatively, as shown in Scheme 5, compounds EZ may be converted to the desired products in a more stepwise fashion. Compounds EZ may be deprotonated using, for example, sodium hydride in DMF and treated with a three carbon based epoxide to generate epoxide EXII. Examples of such reagents include, but are not limited to, epibromohydrin, epichlorohydrin and glycidyl tosylate. Several other potential methods for preparing compounds of the type EXII are well known in the art, for example, the anion of Z may be reacted with allyl bromide or allyl iodide to form an allyl intermediate, which may subsequently be oxidized to form the desired epoxide. Several epoxidation conditions for the generation of either racemic or chiral epoxides are well known in the art. Epoxide EXII may then treated with an amine and susequently carbonylated or sulfonated using activated species well known in the art to generate final compounds of the type E9. Alternatively EXII may be reacted with a functionalized secondary amine followed by optional manipulation of $R^2$ to produce compounds of the type E10. One example of such manipulation is reaction of EXII with the known Boc piperazine EXIII (Dorsey et al., *J. Med. Chem.*,37, pp. 3443–51 (1994)). Subsequent to epoxide opening, the Boc group may be removed and the unmasked secondary amine may be further manipulated by reaction with various electrophiles to form the desired product.

Scheme 6 describes a method for introduction of electrophiles into comounds of the type EXIV. Said compounds may be protected with a variety of protecting groups, for example t-butyldimethylsilyl triflate, to mask the secondary hydroxyl group followed by treatment with a non-nucleophilic base such as lithium diisopropylamide or hexamethyldisilyzane to generate the anion alpha to the carbonyl. Various electrophiles may then be added to substitute the position alpha to the carbonyl. Deprotection of the secondary hydroxyl then yields the desired product.

As can be appreciated by the skilled artisan, the above synthetic schemes are not intended to comprise a comprehensive list of all means by which the compounds described and claimed in this application may be synthesized. Further methods will be evident to those of ordinary skill in the art.

It should be understood that the compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The compounds of this invention are characterized by a superior ability to inhibit protease activity and viral replication, particularly aspartyl protease activity. These compounds are especially well suited for inhibiting HIV aspartyl protease. We believe that this activity is due to specific steric and electronic interactions between the protease and compounds of this invention. This belief stems from our analysis of the structural basis for the activity of compounds of this invention, in view of the known crystal structures of HIV protease and bound inhibitors, such as the structure reported in Miller et al. "Structure of Complex of Synthetic HIV-1 Protease with a Substrate-Based Inhibitor at 2.3 Å Resolution", *Science*, vol. 246, pp. 1149–1152 (1989), which is incorporated herein by reference, as well as structures determined in our laboratories.

The novel compounds of the present invention are excellent ligands for aspartyl proteases, particularly HIV-1 and HIV-2 proteases. Accordingly, these compounds are capable of targeting and inhibiting late stage events in HIV replication, i.e., the processing of the viral polyproteins by HIV encoded proteases. Such compounds inhibit the proteolytic processing of viral polyprotein precursors by inhibiting aspartyl protease. Because aspartyl protease is essential for the production of mature virions, inhibition of that processing effectively blocks the spread of virus by inhibiting the production of infectious virions, particularly from chronically infected-cells. Compounds according to this invention advantageously inhibit the ability of the HIV-1 virus to infect immortalized human T cells over a period of days, as determined by an assay of extracellular p24 antigen—a specific marker of viral replication. Other antiviral assays have confirmed the potency of these compounds.

The compounds of this invention may be employed in a conventional manner for the treatment of viruses, such as HIV and HTLV, which depend on aspartyl proteases for obligatory events in their life cycle. Such methods of treatment, their dosage levels and requirements may be selected by those of ordinary skill in the art from available methods and techniques. For example, a compound of this invention may be combined with a pharmaceutically acceptable adjuvant for administration to a virally-infected patient in a pharmaceutically acceptable manner and in an amount effective to lessen the severity of the viral infection or to alleviate pathological effects associated with HIV infection or immunosuppression such as opportunistic infections or various cancers, tumors, CMV retinitis, candida infections, maternal fetal transmission, and AIDS related dementia,.

Alternatively, the compounds of this invention may be used in prophylactics and methods for protecting individuals against viral infection during a specific event, such as childbirth, or over an extended period of time. The compounds may be employed in such prophylactics either alone or together with other antiretroviral agents to enhance the efficacy of each agent. As such, the novel protease inhibitors of this invention can be administered as agents for treating or preventing HIV infection in a mammal.

The compounds of formula I, especially those having a molecular weight of less than about 700 g/mole, may be readily absorbed into the bloodstream of mammals upon oral administration. Compounds of formula I having a molecular weight of less than about 600 g/mole and aqueous solubility of greater than or equal to 0.1 mg/mL are most likely to demonstrate high and consistent oral availability. This surprisingly impressive oral availability makes such compounds excellent agents for orally-administered treatment and prevention regimens against HIV infection.

The compounds of this invention may be administered to a healthy or HIV-infected patient either as a single agent or in combination with other anti-viral agents which interfere with the replication cycle of HIV. By administering the compounds of this invention with other anti-viral agents which target different events in the viral life cycle and which target different viral substrains with varying susceptability to specific agents, the therapeutic effect of these compounds is potentiated. For instance, the co-administered anti-viral agent can be one which targets early events in the life cycle of the virus, such as cell entry, reverse transcription and viral DNA integration into cellular DNA. Anti-HIV agents targeting such early life cycle events include, didanosine (ddI), dideoxycytidine (ddC), d4T, zidovudine (AZT), 3TC, 935U83, 1592U89, 524W91, polysulfated polysaccharides, sT4 (soluble CD4), ganiclovir, trisodium phosphonoformate, eflornithine, ribavirin, acyclovir, alpha interferon and trimethotrexate. Additionally, non-nucleoside inhibitors of reverse transcriptase, delavirdine (U90) or nevirapine, may be used to potentiate the effect of the compounds of this invention, as may viral uncoating inhibitors, inhibitors of trans-activating proteins such as tat or rev, or inhibitors of the viral integrase.

Combination therapies according to this invention exert an additive or synergistic effect in inhibiting HIV replication because each component agent of the combination acts on a different site of HIV replication or on different strains of virus present in an infectious population. The use of such combination therapies may also advantageously reduce the dosage of a given conventional anti-retroviral agent which would be required for a desired therapeutic or prophylactic effect, as compared to when that agent is administered as a monotherapy. Such combinations may reduce or eliminate the side effects of conventional single anti-retroviral agent therapies, while not interfering with the anti-retroviral activity of those agents. These combinations reduce potential of resistance to single agent therapies, while minimizing any associated toxicity.

Advantages of combining HIV protease inhibitors may include viral population effects, whereby certain members of a virus population which show reduced sensitivity to one protease inhibitor may be fully sensitive to another inhibitor or may in fact have enhanced sensitivity to the second inhibitor. Alternatively or in addition, administration of two or more different inhibitors may be used to reduce specific toxicities associated with a single agent. This advantage of combination therapy also applies to co-administration of the protease inhibitor of this invention with other antiviral agents. Alternatively or in addition, co-administration of more than one protease inhibitor may lower the rate of metabolic inactivation of the compounds of this invention, for instance, by inhibiting enzymatic systems such as cytochrome $P_{450}$, or esterases or the like. In particular, co-administration of compounds of this invention with protease inhibitors such as ritonavir or other agents such as ketoconazole, grapefruit juice and antiulcer medications such as $H_2$-blockers, which inhibits cytochrome $P_{450}$ $3A_4$, may advantageously enhance their biological half-life.

These combinations may also increase the efficacy of the conventional agent without increasing the associated toxicity. Compounds of this invention in combination with other anti-HIV agents may act in an additive or synergistical manner in preventing the replication of HIV in human T cells. Preferred combination therapies include the administration of a compound of this invention with AZT, ddI, ddC, d4T, 3TC, 935U83, 1592U89, 524W91 or a combination thereof.

Alternatively, the compounds of this invention may also be co-administered with other HIV protease inhibitors such as VX-478 (Vertex, also known as 141W94 (Glaxo-Wellcome) and KVX-478 (Kissei)), saquinavir (Ro 31-8959, Roche), indinavir (L-735,524, Merck)), ritonavir (ABT 538, Abbott), nelfinavir (AG 1343, Agouron), palinavir (Bila 2011 BS), U-103017 (Upjohn), XM 412 (DuPont Merck), XM 450 (DuPont Merck), BMS 186318 (Bristol-Meyers Squibb), CPG 53,437 (Ciba Geigy), CPG 61,755 (Ciba Geigy), CPG 70,726 (Ciba Geigy), ABT 378 (Abbott), GS 3333 (Gilead Sciences), GS 3403 (Gilead Sciences), GS 4023 (Gilead Sciences), GS 4035 (Gilead Sciences), GS 4145 (Gilead Sciences), GS 4234 (Gilead Sciences), and GS 4263 (Gilead Sciences) or prodrugs of these or related compounds to increase the effect of therapy or prophylaxis against various viral mutants or members of HIV quasi species.

We prefer administering the compounds of this invention as single agents or in combination with retroviral reverse transcriptase inhibitors, such as nucleoside derivatives, or other HIV aspartyl protease inhibitors, including multiple combinations comprising from 3–5 agents. We believe that the co-administration of the compounds of this invention with retroviral reverse transcriptase inhibitors or HIV aspartyl protease inhibitors may exert a substantial additive or synergistic effect, thereby preventing, substantially reducing, or completely eliminating viral replication or infection or both, and symptoms associated therewith. Particularly preferred is administration of a combination of a compound of formula I, 3TC and zidovudine (AZT). Also preferred are administrations of combinations of a compound of formula I and 1592U89, or of compounds of formula I with VX-478, optionally with one or more reverse transcriptase inhibitors, particularly, AZT, 3TC and 1592U89.

The compounds of this invention can also be administered in combination with immunomodulators and immunostimulators (e.g., bropirimine, anti-human alpha interferon antibody, IL-2, GM-CSF, interferon alpha, diethyldithiocarbamate, tumor necrosis factor, naltrexone, tuscarasol, and rEPO); and antibiotics (e.g., pentamidine isethiorate) to prevent or combat infection and disease associated with HIV infections, such as AIDS, ARC and HIV-associated cancers.

When the compounds of this invention are administered in combination therapies with other agents, they may be administered sequentially or concurrently to the patient. Alternatively, pharmaceutical compositions according to this invention may comprise a combination of an aspartyl protease inhibitor of this invention and one or more therapeutic or prophylactic agents.

Although this invention focuses on the use of the compounds disclosed herein for preventing and treating HIV infection, the compounds of this invention can also be used as inhibitory agents for other viruses which depend on similar aspartyl proteases for obligatory events in their life cycle. These viruses include other AIDS-like diseases caused by retroviruses, such as simian immunodeficiency viruses, HTLV-I and HTLV-II. In addition, the compounds of this invention may also be used to inhibit other aspartyl proteases, such as renin, pepsin, cymosin, RSV protease, AMV protease, SIV protease and FIV protease, and in particular, other human aspartyl proteases, including renin, and aspartyl proteases that process endothelin precursors.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, serum proteins, such as human serum albumin, polyethyleneglycol polymers such as PEG-400, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solublized derivatives may also be advantageously used to enhance delivery of compounds of formula I.

The pharmaceutical compositions of this invention may be administered orally, parenterally, by inhalation spray, topically, rectally, nasally, buccally, vaginally or via an implanted reservoir. We prefer oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as *Ph. Helv* or a similar alcohol.

The pharmaceutical compositions of this invention may be orally administered in any orally acceptable dosage form including, but not limited to, hard or soft gelatin capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 0.5 and about 75 mg/kg body weight per day of the active ingredient compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

The compounds of this invention are also useful as commercial reagents which effectively bind to aspartyl proteases, particularly HIV aspartyl protease. As commercial reagents, the compounds of this invention, and their derivatives, may be used to block proteolysis of a target peptide or may be derivatized to bind to a stable resin as a tethered substrate for affinity chromatography applications. For example, a compound of formula I may be tethered to an affinity column to purify recombinantly produced HIV protease. Derivatization of the compounds of this invention to produce affinity chromatography resins and the methods used to purify proteases using such resins are well known and within the skill of the art. These and other uses which characterize commercial aspartyl protease inhibitors will be evident to those of ordinary skill in the art. (See: Rittenhouse, J. et al. *Biochem. Biophys. Res. Commun.* 171, p. 60 (1990) and Heimbach, J.C. et al. Ibid 164, p. 955 (1989)).

In order that this invention be more fully understood, the following examples are set forth. These examples are for the purpose of illustration only and are not to be construed as limiting the scope of the invention in any way.

General Materials and Methods

All temperatures are recorded in degrees Celsius. Thin layer chromatography (TLC) was carried out using 0.25 mm thick E. Merck silica gel 60 $F_{254}$ plates and elution with the indicated solvent system. Detection of the compounds was carried out by treating the plate with an appropriate visualizing agent, such as 10% solution of phosphomolybdic acid in ethanol or a 0.1% solution of ninhydrin in ethanol, followed by heating, and/or by exposure to UV light or iodine vapors when appropriate. Thick layer silica gel chromatography was also carried out using E. Merck 60 $F_{254}$ plates ("prep plates") of 0.5, 1.0, or 2.0 mm thickness. Following development of the plate, the band of silica containing the desired compound was isolated and eluted with an appropriate solvent. Analytical HPLC was carried out using a Water's Delta Pak, 5 μM silica, C18 reversed-phase column, 3.9 mm ID×15 cm L with a flow rate of 1.5 mL/min using the following table:

| Moblie phase: | A = 0.1% $CF_3CO_2H$ in $H_2O$ |
| | B = 0.1% $CF_3CO_2H$ in $CH_3CN$ |
| Gradient: | T = 0 min., A (95%), B (5%) |
| | T = 20 min., A (0%), B (100%) |
| | T = 22.5 min., A (0%), B (100%) |

Preparative HPLC was also carried out using $C_{18}$ reversed-phase media. HPLC retention times were recorded in minutes. NMR spectral data was recorded using a Bruker AMX500, equipped with either a reverse or QNP probe, at 500 MHz, and was taken in the indicated solvent.

We have measured the inhibition constants of each compound against HIV-1 protease using the method described essentially by M. W. Pennington et al., *Peptides* 1990, Gimet, E. and D. Andrew, Eds., Escom, Leiden, Netherlands (1990); and the method described essentially by Partaledis et al., *J. Virol.*, 69, pp. 5228–35 (1995).

Compounds of invention were tested for their antiviral potency in several virological assays. In the first assay, the compounds were added as a solution in dimethylsulfoxide (DMSO) to a test cell culture of CCRM-CEM cells, a strain of CD4+ human T-cell lymphoma cells, previously acutely infected with $HIV_{IIIb}$ using standard protocols (see Meek, T. D. et al., "Inhibition of HIV-1 protease in infected T-lymphocytes by synthetic peptide analogues", *Nature*, 343, p. 90 (1990).

The effect of the compounds on inhibiting the replication of the virus was measured by determining the HIV extracellular p24 antigen concentration using a commercial enzyme immunoassay (obtained from Coulter Corporation, Hialeah, Fla.).

Depending on the cell type. and the desired readout, syncytia formation, reverse-transcriptase (RT) activity, or cytopathic effect as assayed by a dye uptake method may also be used as readouts of antiviral activity. See H. Mitsuya and S. Broder, "Inhibition of the in vitro infectivity and cytopathic effect of human T-lymphotropic virus type III/lymphoadenopathy-associated virus (HTLV-III/LAV) by 2',3'-dideoxynucleosides", *Proc. Natl. Acad. Sci. USA*, vol. 83, pp. 1911–1915 (1986).

Insofar as the compounds of this invention are able to inhibit the replication of the HIV virus in $CD_4^+$ cells of human lineage, they are of evident clinical utility for the treatment of HIV infection. These tests are predictive of the compounds ability to inhibit HIV protease in vivo.

SYNTHETIC EXAMPLES

SCAFFOLDS

Example 1

A.

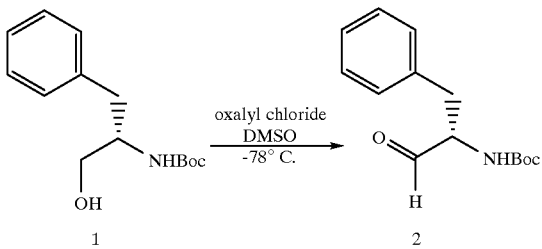

N-(t-butoxycarbonyl)-L-phenylalaninol;

| | 251.3 g/Mol | 10.0 g | 39.8 mmol |
| DMSO | 78 g/Mol | 3.80 mL | 49.0 mmol |
| oxalyl chloride | 126.9 g/Mol | 3.82 mL | 43.8 mmol |
| triethylamine | 101 g/Mol | 23.0 mL | 160 mmol |
| | | 200 mL | |

The oxalyl chloride was added dropwise to a solution of DMSO in methylene chloride at −78° C. After stirring for 10 minutes, the alcohol was added as a solution in methylene chloride. The reaction was then stirred at −78° C. for 45 minutes. At this time the triethylamine was added and a white precipitate formed. The reaction was then stirred 45 minutes at −78° C. and 45 minutes at 0° C. The reaction was then quenched by the addition of a solution of 90 g of citric acid in 300 mL of water. The organic portion of the reaction was then washed by (2×80 mL) of both saturated sodium bicarbonate and brine. The combined organic layers were then dried over sodium sulfate, filtered and concentrated in vacuo to leave a white solid. The aldehyde was then used without further purification in the reductive amination.

B.

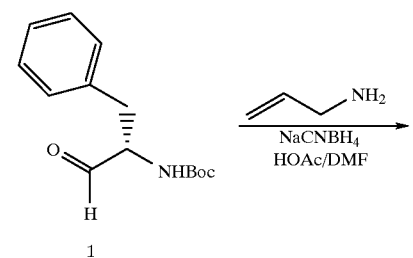

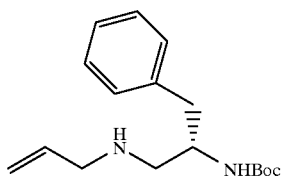

2

| allyl amine | 57 g/Mol | 6.0 mL | 160 mmol |
| --- | --- | --- | --- |
| aldehyde | | est. | 39.8 mmol |
| sodium cyanoborohydride | 62.8 g/Mol | 4.0 g | 6.4 mmol |
| DMF | | | 180 mL |
| acetic acid (glacial) | | | 1.8 mL |

The aldehyde of Example 1A was dissolved in 180 mL of DMF at 25° C. This was followed by addition of the aldehyde and 1.8 mL of acetic acid respectively. After 2 hours sodium cyanoborohydride was added, as a solid. The reaction was then stirred at 25° C. for 12 hours. The reaction was then quenched by the addition of 50 mL of saturated sodium bicarbonate, and after 10 min. diluted by 100 mL of diethyl ether. The organic portion was then washed by (2×50 mL) of both saturated sodium bicarbonate and brine. The combined organic layers were then dried over magnesium sulfate, filtered and concentrated in vacuo. The crude oil was purified by silica gel chromatography eluting with 30% ethyl acetate: hexane to provide 8.8 g of product (29.8 mmol, 75%).

C.

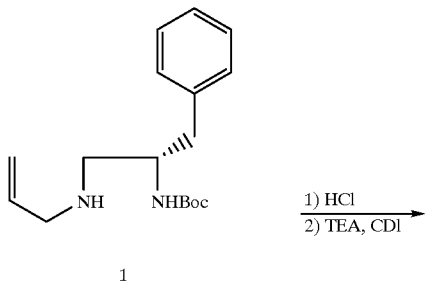

| Boc amine | 291 g/Mol | 6.8 g | 23.4 mmol |
| --- | --- | --- | --- |
| HCl/dioxane | 4 N HCl | 15 mL | |
| deprotected diamine-2HCl | | 3.83 g | 14.7 mmol |
| carbonyl diimidazole | 162.15 g/Mol | 2.77 g | 17.1 mmol |
| triethylamine | | 12.7 mL | 179 mmol |
| methylene chloride | | 550 mL | 0.03M |

The Boc amine of Example 1B was stirred in 15 mL of 4N HCl at 25° C. for 1.5 hours. The reaction mixture was then concentrated in vacuo to provide a white foaming solid. 3.83 mg of the deprotected diamine was dissolved in 500 mL of methylene chloride. To this, triethyl amine was added. After stirring for 20 minutes, CDI was added (solid). The reaction was then stirred for 24 hours. This was followed by concentration in vacuo. The crude material was purified by silica gel chromatography, eluting with ethyl acetate, to provide 2.15 g (67%) of the desired allyl urea.

Example 2

A.

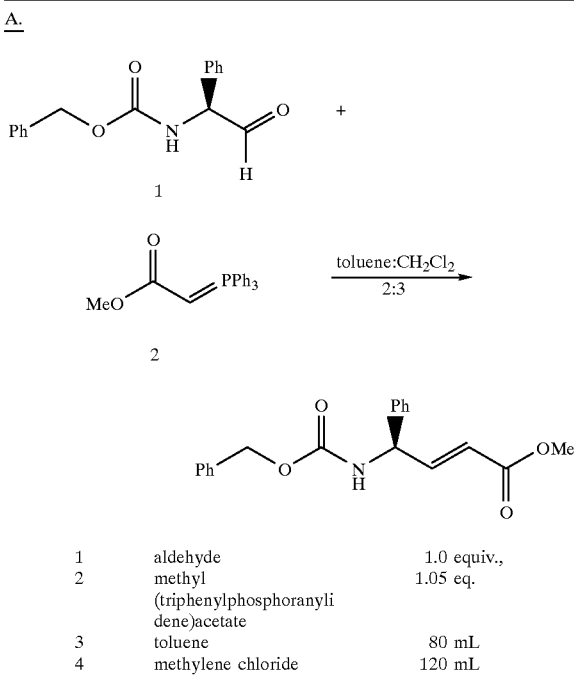

| 1 | aldehyde | 1.0 equiv., |
| --- | --- | --- |
| 2 | methyl (triphenylphosphoranylidene)acetate | 1.05 eq. |
| 3 | toluene | 80 mL |
| 4 | methylene chloride | 120 mL |

Combine 7.9 g of (S)-N-Boc-amino-3-phenyl-1-propanal, 40 mL of anhydrous toluene and 60 mL of anhydrous methylene chloride. Add 9.8 g of the ylide followed by 20 mL of toluene and 60 mL of methylene chloride. Stir overnight at room temperature. After approximatly 18 hours the solvent was removed in vacuo and the residue was purified by flash chromatography. (EtOAc/Hexane) to give 7.1 g(77%) of the desired ester.

B.

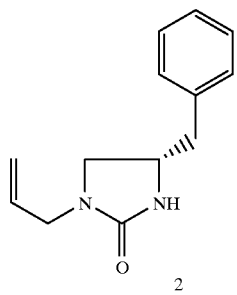

| 1 ester | 4.5 g, 1.0 equiv. |
| --- | --- |

| | |
|---|---|
| 2 magnesium turnings (Aldrich) | 3.2 g 10.0 eq. |
| 3 2N HCl | @ 10 eq. |

To a solution of ester 1 in anhydrous methanol at 0° C. was added Mg turnings with stirring under $N_2$. Bubbling became evident within 1 hour. The reaction was then stirred at 0° C. for ~2.5 hours then allowed to warm to RT overnight (TLC (95:5, $CH_2Cl_2$:MeOH) showed reaction complete. st. mat. Rf=0.84, prod. Rf=0.25). The reaction was cooled to 0° C., neutralized with 2N HCl, diluted with water, and the volume reduced in vacuo. The remaining aqueous layer was extracted with 3 portions of methylene chloride and the combined organic layers were washed with brine, dried ($MgSO_4$), filtered, and concentrated in vacuo. The residue was then purified by silica get flash chromatography ($CH_2Cl_2 \rightarrow >3\%$ MeOH/$CH_2Cl_2$) to yield desired lactam product (1.74 g, 75% yield). Literature reference: *Tetrahedron. Lett.*, 1993, 34 (28), pp. 4439–4442.

C.

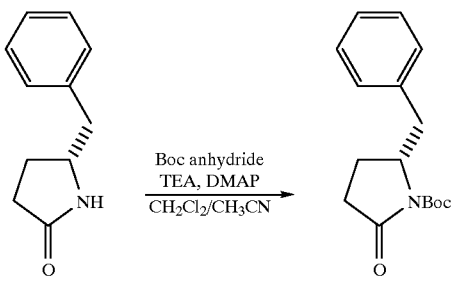

| | |
|---|---|
| 1 lactam from 2B | 1.0 equiv., 1.7 g |
| 2 BOC anhydride | 2.5 equiv., 5.2 g |
| 3 triethylamine | 2.0 equiv., 2.7 mL |
| 4 DMAP | 1.2 equiv, 1.4 g |

Lactam 1 was dissolved in methylene chloride (20 mL) and to this solution was added a solution of Boc anhydride 2 in $CH_2Cl_2$ (10 ml) followed by triethylamine (2 eq) and DMAP (1.2 eq). After stirring for 4 hours at room temperature the reaction was refluxed for 4 hours and after this time, an additional 1.0 g of Boc anhydride in acetonitrile (20 mL) and 700 uL of triethylamine were added. The reaction was stirred for 15 hours at room temperature. (TLC (95:5, $CH_2Cl_2$: MeOH) Rf (st mat.)=0.31 Rf(prod)=0.66.) The solvent was then removed in vacuo and the residue was partitioned between methylene chloride and water. The organic layer was washed with water and brine, dried ($MgSO_4$) and filtered. The dried organic layer was then concentrated in vacuo and the residue was purified by silica gel chromatography ($CH_2Cl_2$) to yield desired boc lactam 2 (2.3 g, 86%).

D.

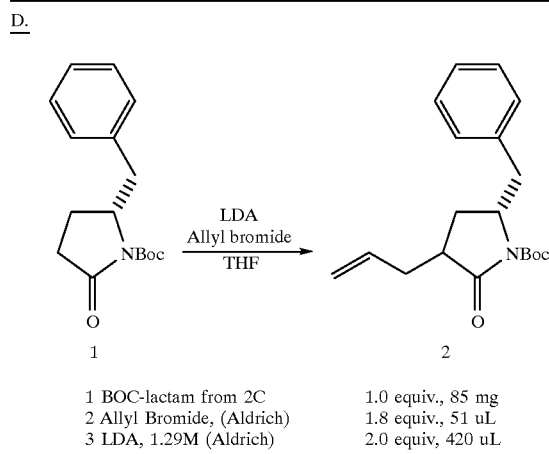

| | |
|---|---|
| 1 BOC-lactam from 2C | 1.0 equiv., 85 mg |
| 2 Allyl Bromide, (Aldrich) | 1.8 equiv., 51 uL |
| 3 LDA, 1.29M (Aldrich) | 2.0 equiv, 420 uL |

Boc-lactam 1 was dissolved in dry THF and cooled to −78° C. and to this solution was added LDA via syringe. After stirring for 40 min. at −78° C., allyl bromide was added via syringe and the reaction was stirred for 3 hours after which time an additional amount of allyl bromide (17 ul) was added. The reaction was then stirred at −78° C. for 4 hours (TLC (5:95, MeOH:$CH_2Cl_2$) Rf (st mat.)=0.34. Rf(2 diast.)=0.55 and 0.61). The reaction was then quenched with 1 mL saturated NaCl solution, and partitioned between saturated sodium bicarbonate and ethyl acetate. The organic layer was then washed with water and brine, dried (MgSO4), filtered and concentrated in vacuo. The residue was purified by silica get chromatography to yield allylated product 2 (47 mg, 48% yield)

E.

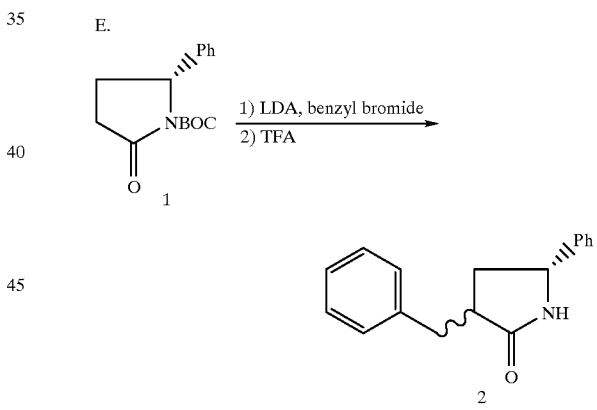

A mixture of diisopropylamine (4.6 mL, 3 eq) and THF (10 mL) was cooled to −78° C., and to this solution was added n-butyl lithium (1.4 eq) via syringe. This mixture was warmed to −10° C. and stirred for 40 min, after which time the mixture was cooled back to −78° C. A solution of Boc lactam 1 (3.0 g, 1 eq) in THF (15 mL total) was added. The reaction mixture was then stirred at −78° C. for 40 min followed by the addition of benzyl bromide (1.45 mL, 1.1 eq) via syringe. After stirring for 2.5 hours at −78° C., the reaction was warmed to −45° C. and stirred an additional 1 hour. The reaction was then quenched at −78° C., with 0.5 mL saturated NaCl solution. The reaction was warmed to room temperature, diluted with ethyl acetate and the organic layer was washed with water and satuated NaCl, dried ($MgSO_4$) and concentrated in vacuo. The residue was then dissolved in methylene chloride (50 mL) and to this solution was added triflouroacetic acid (8 mL, excess). After 4 hours the reaction was concentrated in vacuo, and partitioned between a saturated solution of sodium bicarbonate and ethyl acetate. The organic layer was washed with water and brine and then dried (MgSO$_4$) and concentrated in vacuo. The resulting residue was purified by flash silica get chromatography to give 726 mg (30%) of the desired benzyl lactam product 2 as a mixture of diastereomers.

Example 3

A.    Example 3

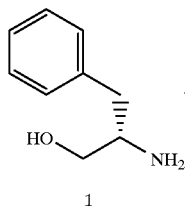

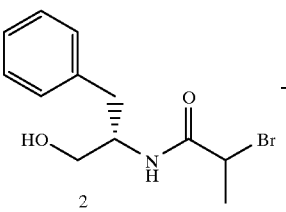

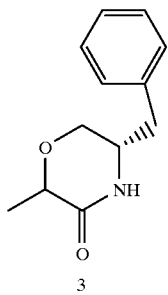

Synthesis of 2-oxo-3-methyl-6-phenylmethylmorpholine

Dissolve S-(−)-2-Amino-3-phenyl-1-propanol (1.51 g, 10 mmol) in THF (10 ml). To 0° C. solution add (rac)-2-bromopropionyl bromide (1.04 ml, 10 mmol), followed by a dropwise addition of diisopropylethylamine (1.73 ml, 10 mmol). Warm up to rt and continue stirring for 90 min. Remove solvents in vacuo and remove salts by ethyl acetate/water extraction (3×). Following magnesium sulfate drying, the ethyl acetate layer is evaporated and residue redissolved in anhydrous THF. To 0° C. solution of intermediate 2 add 13 mM of NaH (from 60% mineral oil dispersion, removed by washing, with hexane). Solution was warmed up to rt and reaction terminated (MeOH) after 1 hr. Residue left after solvents removal was again partitioned between ethyl acetate/water (2×), organic phases combined, dried with magnesium sulfate, filtered and evaporated, resulting in 1.20 g crude product. Silica gel chromatography (ethyl acetate) yielded 0.70 g of pure product, 34% yield. $^1$H NMR (CDC13): 7.25 (m, 5H), 6.75 (broad s, 1H), 4.19 (q, 1H, J=7.0 Hz), 3.76 (2H, d, J=7.5 Hz), 3.57 (1H, m), 2.90 (2H, m), 1.49+1.46 (both s, total integration 3H). CHN: 70.0 (calc: 70.2), 7.3 (7.4), 6.8 (6.8). Mass Spec. (API-)=204 (M−1). Silica gel plates: Rf=0.19 (1/1 ethyl acetate/hexane). HPLC at 220 nm (YMC 0.46 cm×25 cm C$_{18}$ reverse phase) t=11.47 min (single peak), gradient: 0–100% B/30 min, 1.5 ml/min, A=0.1% TFA in water, B=0.1% TFA in acetonitrile.

B.

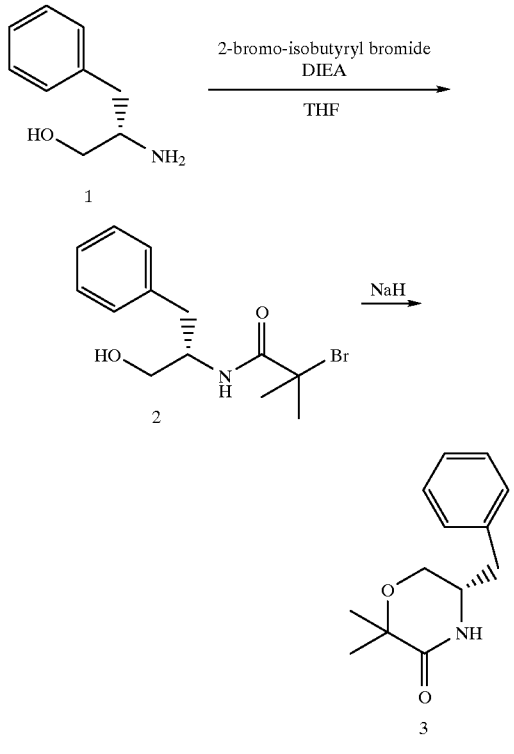

Synthesis of 2-oxo-3,3-dimethyl6-phenylmethylmorpholine

Dissolve 3.02 g (20 mM) of S-(−)-2-Amino-3-phenyl-1-propanol in 10 ml THF. To 0° C. solution add 2-Bromoisobutyryl bromide (2.47 ml, 20 mmol), followed by dropwise addition of diisopropylethylamine (3.47 ml, 20 mmol). Warm up to rt and continue stirring for 90 min. Remove solvents in vacuo and remove salts by ethyl acetate/water extraction (3×). Following magnesium sulfate drying, the ethyl acetate layer is evaporated and residue redissolved in anhydrous THF. Following silica gel chromatography (1/1 ethyl acetate/hexane), 1.20 g of intermediate 2 is isolated from mixture containing overacylation product.

To 0° C. solution of 2 in 4 ml of anhydrous DMF add 4 mM of NaH (from 60% mineral oil dispersion, removed by washing with hexane).

After 14 hrs at rt, the solvent was removed and solid residue partitioned between ethyl acetate/water (2×), organic phases combined, filtered, evaporated and (silica gel) chromatographed with ethyl acetate, resulting in 0.20 g of product homogenous by TLC, but heterogeneous by HPLC.

83

C.

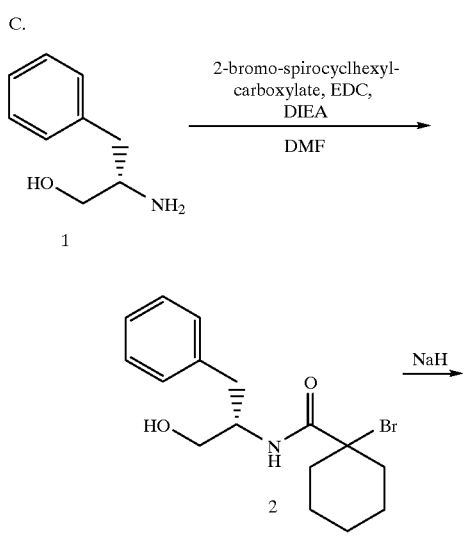

Synthesis of 2-oxo-3,3-spirocyclohexyl6-phenylmethylmorpholine

A solution containing, 1-bromocyclohexylcarboxylate (0.5 g, 2.4 mmol) and anhydrous DMF (3 ml) was diluted with S-(+)-2-amino-3-cyclohexyl-1-propanol hydrochloride (0.465 g, 2.4 mmol), N,N'-ethyl-dimethylaminopropylcarbodiimide hydrochloride (0.69 g, 3.6 mmol) and diisopropylethylamine (1.25 ml, 7.2 mmol). After stirring at room temperature for 2 hrs, the reaction was concentrated in vacuo. The crude product was purified by ethyl acetate/water extraction (3×), followed by drying with magnesium sulfate drying, resulting in 0.45 g (1.3 mM) of clear oil. The product was then redissolved in 3 ml anhydrous DMF, cooled to 0° C., added 67.7 mg (17 nmM) of NaH (from 60% mineral oil dispersion, removed by washing with hexane) and stirred for 30 hrs at 50° C. Reaction was then terminated and solvent removed, following by ethyl acetate/aqueous citric acid workup, resulting in 0.19 g (0.72 mM), yield 30%, of the desired product. 1H NMR consistent w/structure.

84

Example 4

A.  Example 4

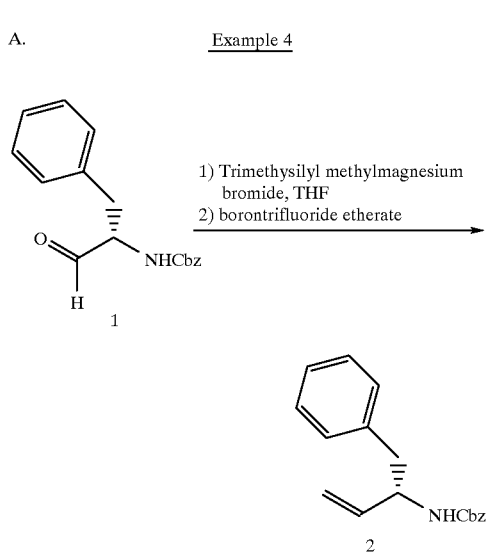

70 g of the aldehyde 1 was dissolved in 40 mL of THF and added dropwise to a cooled (−78°) solution of 128 mL (128 mMol) of 1M trimethylsilyl methylmagnesium bromide in ether. The resulting mixture was allowed to warm to rt and poured into water. After diluting with ethyl acetate and 1N HCl, the layers were separated and the organic layer was washed with 10% aqueous sodium bicarbonate. Drying over magnesium sulfate and removal of the solvent in vacuo gave a viscous oil, which was re-dissolved in 150 mL of dichloromethane and treated dropwise with 15.6 mL of borontrifluoride etherate. The resulting mixture was stirred for 5 days at rt and then quenched with 10% NaOH. The organic layer was dried and evaporated and the residue was chromatographed on silica gel (20% ethyl acetate/hexanes) to give 5.2 g of a yellow solid. Recrystallization from hexane yielded 4.6 g of the desired alkene as a white solid in three crops.

B.

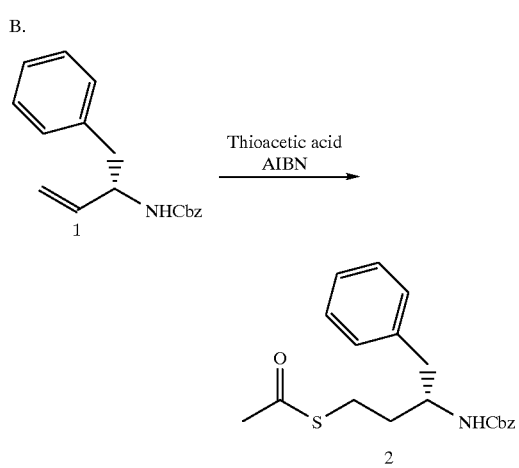

2.0 g (7.1 mMol) of the alkene from the previous step were mixed with 10 mL of carbon tetrachloride and 1.4 mL (20 mMol) of thioacetic acid. A spatula tip of AIBN was added and the mixture was irradiated in a quartz vessel at 254 nm for 2 h. The resulting mixture was diluted with dichloromethane and extracted with satd. aqueous sodium bicarbonate. Drying and removal of the solvent, followed by chromatography on silica gel (15% ethyl acetate/hexane) gave the desired thioacetate (2.0 g) as a pale yellow liquid which solidified on standing.

C.
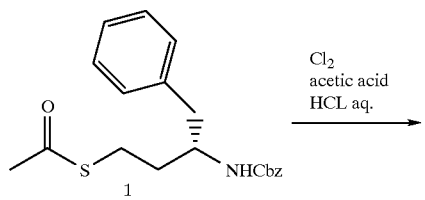

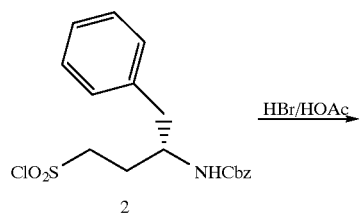

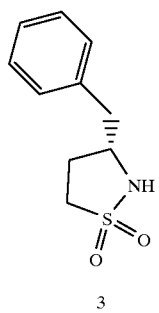

A solution of 0.85 g of the thioacetate from the previous step in 30 mL of acetic acid and 15 mL of 1N HCl was cooled on ice and exposed to a stream of chlorine gas for 2 h. Ethyl acetate was added and the organic layer was separated, dried and co-evaporated with toluene to give the desired sulfonyl chloride as a white solid (1.05 g).

0.7 g of the sulfonyl chloride 2 obtained in the previous step were dissolved in 30 mL of 30% HBr in acetic acid. After 2 h, the volatiles were removed in vacuo, the gummy residue was redissolved in 100 mL of chloroform and the solution was treated with 1 mL of triethylamine. The mixture was stirred for 1 h and then extracted with 1N HCl and 10% aqueous sodium bicarbonate. Drying over magnesium sulfate and removal of the solvent gave a brown oil which was chromatographed on silica gel (2% MeOH/dichloromethane) to give the desired sulfonamide as an off-white solid (0.305 g). 1H-NMR (CDC13): 2.20 (1H,m), 2.48 (1H,m), 2.89 (2H,m), 3.10 (1H,m), 3.23 1H,m), 3.84 (1H, m), 4.18 (1H, bs), 7.30 (5H,m). 13C-NMR (CDC13): 28.8, 42.0, 47.8, 56.2, 127.8, 129.1, 129.3, 136.6.

Example 5

Synthesis of Sulfamate

A.
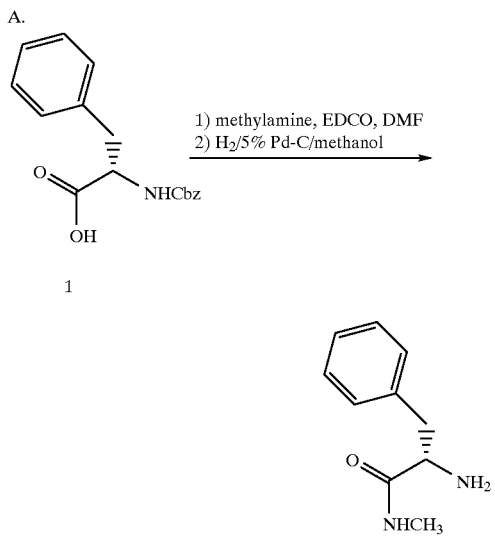

A solution of 30 g of Cbz-(L)-phenylalanine, 6.8 g of methylamine hydrochloride, 14.8 g of hydroxybenzotriazole and 22 mL of N-methylmorpholine in 300 mL of dimethylformamide was cooled on an ice-bath and treated with 19.2 g of EDCI. The mixture was allowed to reach rt overnight and then poured into 2000 mL of water. The product was collected by filtration, dried and redissolved in 500 mL of methanol and 300 mL of THF. 1 g of 5% palladium on carbon was added and the mixture was stirred under hydrogen for 36 h. Filtration and removal of the solvent, followed by short plug filtration through silica gel (5% MeOH(2M NH3)/dichloromethane) gave the desire amine as a pale yellow solid (17 g).

B.
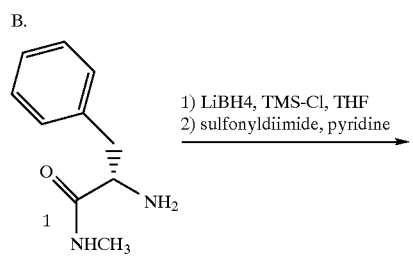

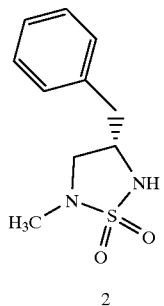

A solution of 1.22 g (56 mmol) of lithiumborohydride in 28 mL of THF was treated with 14.2 mL (112 mMol) of chlorotrimethyl silane. The resulting mixture was treated scoopwise with 5 g (28 mMol) of the amide from the previous step. After stirring at rt for 24 h, 40 mL of methanol were added carefully, followed by 10 mL of acetic acid. Repeated evaporation from methanol gave a colorless glass, which was dissolved in 100 mL of 20% NaOH. Extraction with 4×50 mL of chloroform, followed by drying and removal of the solvent gave a yellow oil which was chromatographed on silica gel (20% methanol(2M ammonia)/dichloromethane) to give 1.5 g of the desired diamine as a colorless oil, and 2.0 g of recovered starting material.

0.15 g of the diamine from the previous step were dissolved in 0.5 mL of pyridine and added dropwise to a refluxing solution of 0.1 g of sulfonyldiimide in 1.5 mL of pyridine. Reflux was continued for 24 h and the volatiles were removed in vacuo. The resulting brown oil was chromatographed on silica gel (20% methanol(2M ammonia)/dichloromethane) to give the desired sulfonylurea as a yellow oil (0.04 g). $^1$H-NMR (CD$_3$OD): 2.60 (3H,s), 2.86 (1H,dd), 2.96 (1H,dd), 3.15 (1H,dd), 3.47 (1H,dd), 4.18 (1H, m), 7.22 (5H,m), 7.38 (1H,d). $^{13}$C-NMR (CD$_3$OD): 31.8, 39.9, 50.0, 57.8, 126.5, 128.2, 129.0, 136.6

Example 6

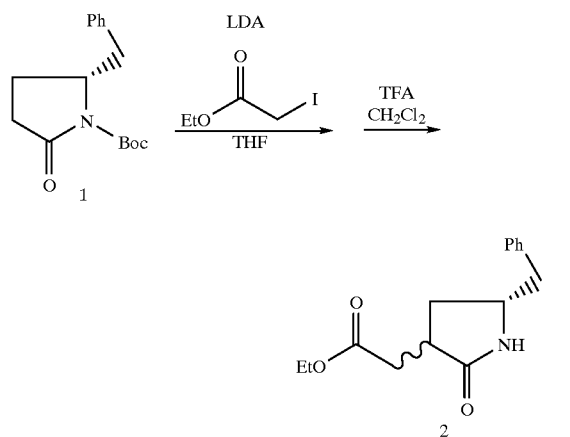

Boc lactam 1 (1.27 g, leq) was dissolved in THF (27 mL) and cooled to −78° C. To this solution was added LDA (Aldrich, 1.5M in hexane, 3.7 mL, 1.2 eq) via syringe over 3 minutes. After stirring for 85 minutes at −78° C., a solution of ethyl iodoacetate (600 uL, 1.1 eq) in THF (13 mL) was added via syringe over 6 minutes. The reaction was then stirred at −78° C. for 4.5 hours, then at 1.5 hours at −40° C. The reaction was then cooled back to −78° C. and quenched with 2.5 mL saturated NaCl solution, and partitioned between saturated sodium bicarbonate and ethyl acetate. The organic layer was then washed with brine, dried (MgSO$_4$), filtered and concentrated in vacuo. The residue was purified by flash silica get chromatography eluting with 5% EtOAc/CH$_2$Cl$_2$to give 1.67 g of substituted lactam product 2 contaminated with a minor amount of lactam starting material 1. HPLC showed 52% product and 28% starting material. This mixture was then dissolved in methylene chloride (45 mL) and cooled to 0° C. To this solution was added trifluoroacetic acid (2 mL) and the reaction was stirred at room temperature for 1.5 hr. TLC showed no BOC material and the reaction was concentrate in vacuo and partitioned between saturated bicarbonate solution and ethyl acetate. The organic was washed with water, brine and dried (MgSO$_4$). The organic layer was evaporated in vacuo, and the residue was purified by flash chromatography eluting with 3:1 EtOAc/hexane to give 770 mg of pure lactam product 2.

Example 7

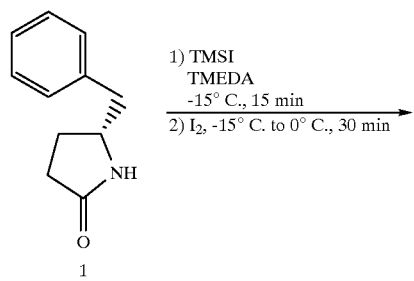

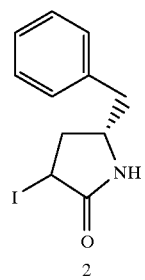

A solution of 5-benzyl-pyrrolidinone 1 (1.5 gr, 8.86 mmol) was dissolved at ambient temperature under nitrogen in anhydrous dichloromethane (40 mL). TMEDA (6.5 mL, 42.8 mmol) was added via pipette and the solution was cooled and maintained at −20° C. TMSI (2.33 mL, 17.12 mmol) was added via pipette and the mixture was stirred for 15 min. Solid iodine (4.345 g, 17.12 mmol) was added and the mixture was stirred vigorously for 15 minutes and then quenched by rapid addition of the reaction mixture into aqueous 10% sodium sulfite solution (100 mL). The mixture was transferred to a separatory funnel and the layers were separated. The organic layer was washed with 1N NaHSO$_4$, water, and then dried over MgSO$_4$. The solution was then diluted in half with methanol and stirred overnight under a nitrogen atmosphere. The solvent was removed in vacuo and the residue was purified by flash chromatography, eluting with ethyl acetate:hexane (7:3). Pure iodo lactam product 2 was recovered as a solid (2.11 g).

Example 8

A.

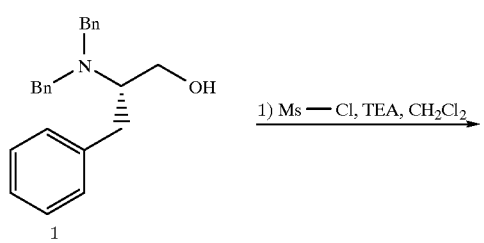

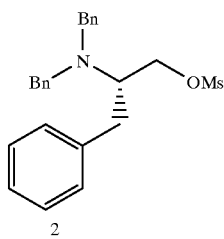

To a solution of dibenzylphenylalinol 1 (100 mmol) in methylene chloride (100 mL), was added triethylamine (150 mmol). The mixture was cooled to 0° C. and methanesulfonyl chloride (110 mmol) was slowly added. The mixture was stirred at 0° C. for one hour and then poured into a beaker containing diethyl ether (400 mL). The mixture was filtered and washed with more diethyl ether and the filtrate was washed with water, saturated $NaHCO_3$ and saturated brine. The organic layer was then dried ($MgSO_4$), filtered and concentrated to yield 41 g of crude mesylate product 2 as a light yellow-brown thick oil, which was used as is in subsequent steps.

B.

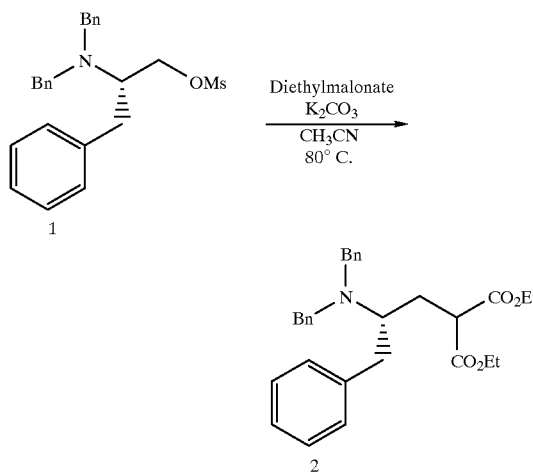

Diethyl malonate (300 mmol) was dissolved in acetonitrile (250 mL) and to this solution was added potassium carbonate (300 mmol); the suspension was stirred overnight at room temperature. Mesylate 1 (100 mmol) in acetonitrile (60 mL) was then added to the reaction mixture which was then heated to 80° C. and stirred overnight. The reaction mixture was then filtered and concentrated in vacuo. Addition of hexane to the residue formed a precipitate, which was filtered as pure malonate product 2 (19.5 g). Material was used as is.

C.

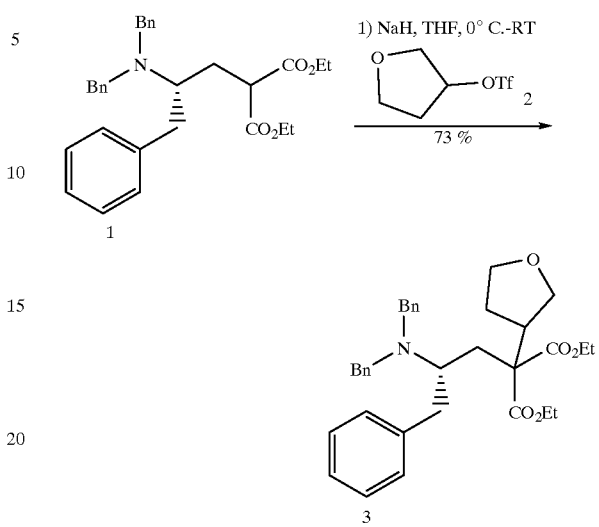

Malonate 1 (10.6 mmol) was dissolved in dry THF (40 mL) and cooled to 0° C. To this solution, sodium hydride (17 mmol) was added in portions and the suspension was stirred for 1.5 hr at 0° C. The triflate 2 (12 mmol) in dry THF (10 mL) was then slowly added to the reaction mixture and after complete addition the reaction was allowed to warm to room temperature and was stirred overnight. The reaction was then diluted with water (100 mL) and extracted with diethyl ether (3×50 mL). The combined organic layers were then washed with saturated brine, dried over $MgSO_4$, filtered and concentrated in vacuo. The crude product was purified by mplc (eluted with a gradient of 9:1 hexane:ethyl acetate up to 4:1 hexane:ethyl acetate to yield product 3 (4.2 g, 73%)

D.

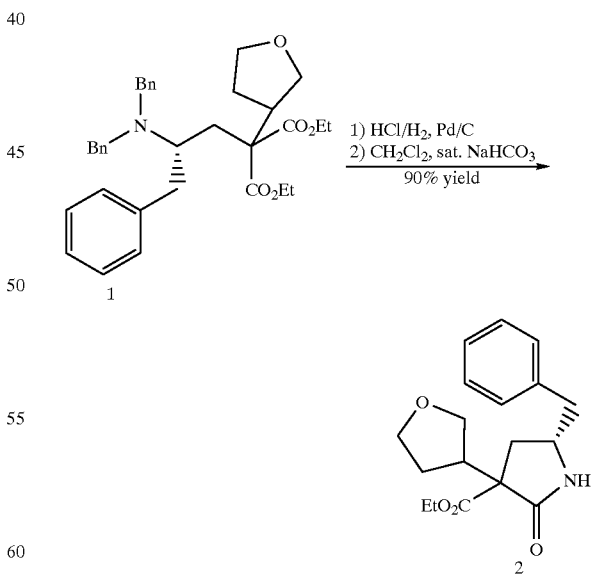

The subsituted malonate 1 (1.62 mmol) was suspended in ethanol and to this was added conc. HCl (0.24 mL, 2.4 mmol) and 10% palladium on Carbon (0.162 mmol). This mixture was then stirred under a balloon of hydrogen gas at room temperature overnight. The reaction was then filtered through Celite and to the filtrate was added triethylamine (10 mL, excess) followed by solid sodium bicarbonate (excess). The mixture was stirred for 0.5 hr, filtered and concentrated to yield a yellow solid. This residue was then dissolved in ethyl acetate and washed with water, 0.5N HCl, saturated sodium bicarbonate, and brine. The organic layer was dried (MgSO$_4$), filtered, and dried to yield crude lactam product 2, which was used as is.

E.

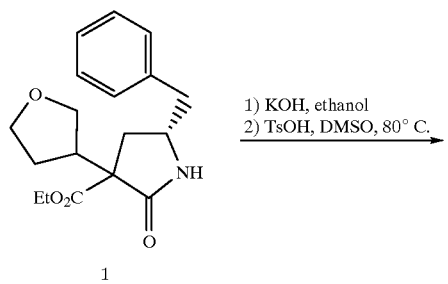

Lactam 1 (1.18 mmol) was dissolved in ethanol (5 mL) and to this solution was added KOH (10 mmol). The mixture was stirred for 3 hr at room temperature and then concentrated to dryness. The residue was dissolved in water and washed with diethyl ether. The aqueous layer was then acidified with HCl and extracted with ethyl acetate. The organic layer was dried (MgSO4), filtered and concentrated in vacuo to yield 341 mg of a light yellow solid. The residue was dissolved in DMSO (3 mL) and to this solution was added p-toluenesulfonic acid mono- hydrate, and the mixture was heated to 80° C. overnight. The mixture was diluted with water (15 mL) and extracted with ethyl acetate. The organic layer was washed with saturated sodium carbonate and brine followed by drying with MgSO$_4$. The organic layer was then filtered and concentrated in vacuo to yield the THF substituted lactam product (245 mg, 77% from ester) which was used as is in the next step without further purification.

Example 9

A.

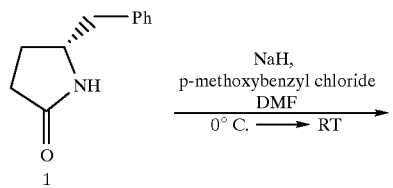

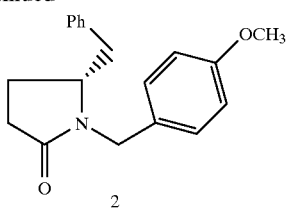

Sodium hydride (60% dispersion in mineral oil, 4.0 g, 1.17 eq) was washed with 4×25 mL portions of hexanes to remove the mineral oil, then suspended in 25 mL of DMF and cooled to 0° C. A solution of lactam 1 (15 g, 1 eq) in dry DMF (25 mL) was then added dropwise via canula into the cold NaH suspension over 40 min. An additional 65 mL of DMF was then added to aid stirring. After stirring the anion for 1 hour, p-methoxybenzyl chloride (14.5 mL, 1.26 eq) was added over 5 min at 0° C. The reaction was then allowed to warm to room temp. An additional amount of p-methoxybenzyl chloride was added to drive the reaction to completion. TLC (EtOAC) Rf lactam 1=0.21. Rf product 2=0.43. After 3.5 hours, the reaction was poured into cold water and extracted twice with ethyl acetate. The combined organic layers were washed with water (5×), brine, dried (MgSO$_4$) and filtered. Concentration in vacuo, afforded a crude solid which was purified by crystallization(7:1 hexane:EtOAc) to yield the protected lactam product 2 (19 g, 75%).

B.

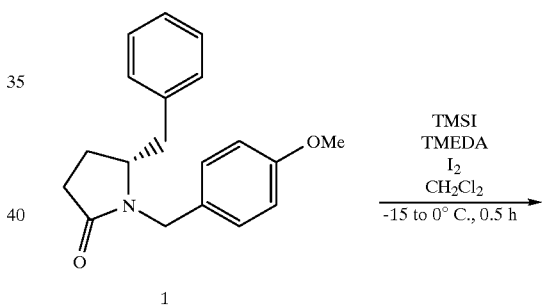

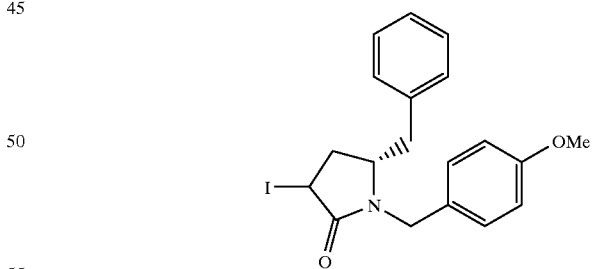

To protected lactam 1 (328 mg, 1.11 mmol) and N,N,N$^1$, N$^1$-tetramethylethylenediamine (Aldrich, 5.0 equiv., 5.55 mmol, 645 mg, 838 ml) in 15 ml dichloromethane at −15° C., was added iodotrimethylsilane (Aldrich, 1.0 equiv., 1.11 mmol, 222 mg, 158 ml). After 15 min, iodine (Aldrich, 1.2 equiv., 1.33 mmol, 338 mg) was added in one portion and the reaction warmed to 0° C. After 30 min the reaction was quenched with 5 ml each of 10% aqueous sodium sulfite and saturated aqueous sodium chloride. The orgnic layer was separated, dried over magnesium sulfate, filtered and concentrated in vacuo. Purification by flash column chromatography (silica gel, 2.5×10 cm, 2.5% diethylether in dichloromethane) yielded 322 mg of diastereomeric iodolactam 2 as a white solid.

C.

To iodolactam 1 (1.18 g, 2.91 mmol) and methyl vinyl sulfone (Aldrich, 6.0 equiv., 17 mmol, 1.82 g, 1.5 ml) in 25 ml refluxing toluene was added tributyltin hydride (Aldrich, 1.3 equiv., 3.79 mmol, 1.10 g, 1.0 ml) and AIBN (Pfaltz & Bauer, 0.12 equiv., 0.35 mmol, 57 mg) as a solution in 5 ml toluene over 1.2 h. After 16 h the solvent was removed in vacuo, and the residue taken up in 200 ml diethyl ether and stirred with 20 ml 10% aqueous potassium fluoride (wt/v) at ambient temperature. After 3 h the orgnic layer was separated, dried over magnesium sulfate, filtered and concentrated in vacuo . Purification by flash column chromatography (silica gel, 5×20 cm, 2:1 ethyl acetate/hexanes) yielded 0.31 g of diastereomeric sulfone 2 as a white solid.

Example 10

A.

To a solution of solution of Cbz-L-phenylalinal (13 g, 45.9 mmol) in 1% AcOH/DMF (200 mL) mL was added aminoisobutyic acid methyl ester hydrochloride 1 (8.5 g, 55.1 mmol) with stirring at room temperature. Once homogeneous, solid sodium cyanoborohydride (8.6 g, 137.6 mmol) was added in one portion. Some bubbling was evident and the reaction was stirred overnight at room temperature. The reaction was quenched with water (20 mL) and concentrated in vacuo to about 100 mL. The concentrate was diluted with ethyl acetate and washed with water and brine followed by drying ($MgSO_4$). The organic layer was evaporated in vacuo to yield a yellow residue which was purified by MPLC (elutant 1:2 ethyl acetate:hexane) to afford amine product 2 (11.6 g, 66%).

B.

To a solution of amine 1 (1.41 gr, 3.7 mmol) in methylene chloride (25 mL) was added 30% HBr in acetic acid (6 mL) via pipet. Vigorous gas evolution occurred and the reaction was allowed to stir overnight at room temperature. The mixture was then evaporated in vacuo and dried under high vacuum. The residue was then dissolved in methanol (25 mL) and to this solution was added diisopropylethylamine (5 eq) and the reaction was stirred at room temperature overnight. The solvent was removed in vacuo and the residue was taken up in ethyl acetate and washed with water, saturated $NaHCO_3$ and brine. The organic layer was dried ($MgSO_4$) filtered and concentrated in vacuo to yield crude product. Flash silica gel chromatography (8% methanol/ methylene chloride) afforded pure piperazinone product 2 (556 mg, 70%)

C.

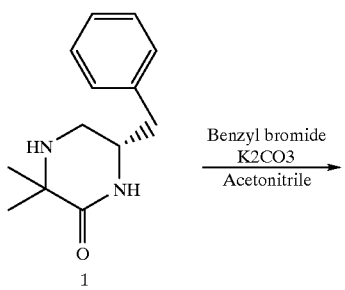

To a solution of piperazinone 1 (556 mg, 2.55 mmol) and potassium carbonate (1.06 g, 7.6 mmol) in acetonitrile was added benzyl bromide (364 uL, 3 mmol) and the reaction was stirred at room temperature overnight. The reaction was then filtered and concentrated in vacuo. The residue was dissolved in ethyl acetate, washed with water and brine and dried (MgSO$_4$). The organic layer was then removed in vacuo and the residue was flash chromatographed (3% methanol in methylene chloride) to yield pure benzyl protected piperazinone product 2 (589 mg, 75%).

Example 11

A.

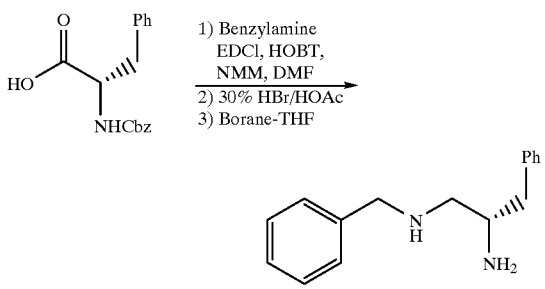

A solution of Cbz-(1)-Phenylalanine (15 gr, 50 mmol), HOBT (7.4 g, 50 mmol), N-methyl morpholine (5.5 mL, 50 mmol) and benzylamine (6 mL, 55 mmol) in 250 mL of DMF was cooled to 0° C. and treated with EDCI (9.6 g, 50 mmol). The resulting mixture was stirred at 25° C. for 12 h and the volatiles were removed in vacuo. Partitioning between ethyl acetate and 1N hydrochloric acid, followed by extraction with 10% sodium bicarbonate, drying over magnesium sulfate and evaporation of the solvent afforded the desired amide as a white solid (19.5 g).

19 g of the above material were dissolved in 280 mL of 30% hydrogen bromide in acetic acid and stirred at 25° C. for 3 h. The volatiles were removed and the residue was partitioned between water and ether. The aqueous layer was treated with excess 6N sodium hydroxide and extracted twice with ethyl acetate. Drying over magnesium sulfate and evaporation of the solvent afforded the desired amine as a pale yellow oil (14.0 g), which was redissloved in 200 mL of tetrahydrofuran and treated with 200 mL of 1M borane-THF in tetrahydrofuran. The mixture was stirred at 25° C. for 72 h and then heated to reflux for 4 h. The solution was cooled and treated with 100 mL of methanol under vigorous gas evolution. The volatiles were removed and the resulting residue was dissolved in 150 mL of concentrated hydrochloric acid. After refluxing for 1 h, the volatiles were removed and the residue was dissolved in 300 mL of 3N sodium hydroxide. Extraction with 3 times 250 mL of dichloromethane, drying over magnesium sulfate and chromatography on 2 inches of silica gel (2% methanol-dichloromethane) gave the desired diamine as a pale yellow honey (9.2 g).

B.

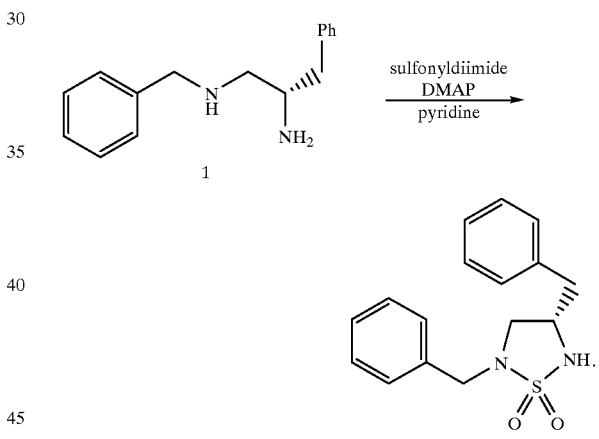

A solution of sulfonyldiimide (3.6 g, 36 mmol) in 100 mL of pyridine was heated to reflux and treated dropwise with a solution of the diamine 1 (7.2 g, 30 mmol) from the previous step in 20 mL of pyridine. After 2 h of reflux, 15 mL of triethylamine and 0.4 g of 4-dimethylaminopyridine were added and heating was continued for 12 h. The volatiles were evaporated and the residue was partitioned between 1N hydrochloric acid and ethyl acetate. Extraction of the organic layer with saturated sodium bicarbonate, drying over magnesium sulfate and chromatography on silica gel (1:1 ethylacetate-hexanes) afforded the desired cyclic sulfamate 2 as a white solid (6.0 g).

1H-HMR (CDCl3): 2.80(1H,dd), 2.96(1H,dd), 2.98(1H, dd), 3.32(1H,dd), 3.95(1H,m), 4.04(1H,d), 4.24(1H,d), 4.40 (1H,d), 7.18(2H,d), 7.2–7.4(8H) 13C-NMR(CDCl3): 41.5, 50.0, 52.7, 53.8, 127.5, 128.0, 128.2, 128.3, 28.4, 128.5, 135.5, 136.0.

Example 12

A.

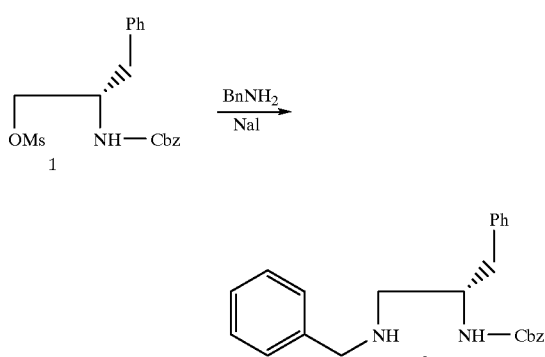

C.

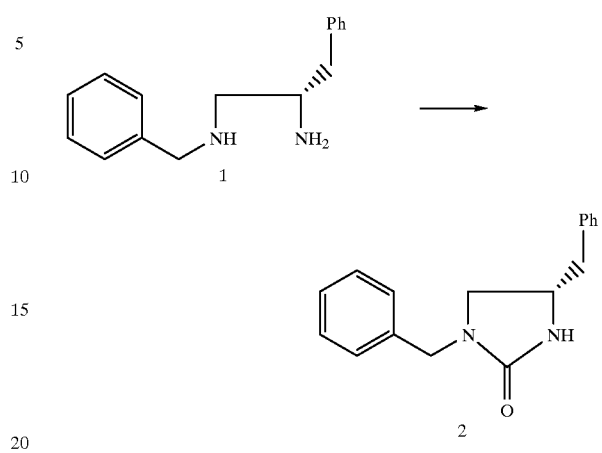

The Cbz-phenylalaninol mesylate 1 (280 mg, 0.77 mmol) was stirred in acetonitrile (5 mL) containing benzyl amine (413 mg, 3.85 mmol) and sodium iodide (115 mg, 0.77 mmol). The reaction was then refluxed for 24 hours. The reaction was then cooled to 25° C. and concentrated in vacuo. The crude oil was then purified by silica gel chromatography, eluting with $CH_2Cl_2$ with a gradient up to 1:1 $CH_2Cl_2$:EtOAc to provide 120 mg of the desired diamine 2.

The diamine 1 (56 mg, 0.23 mmol) was dissolved in 3.0 mL of $CH_2Cl_2$. This was followed by the addition of TEA (66 uL, 0.25 mmol) and then CDI (32 mg, 0.25 mmol). A new spot was observed by tlc after 2–3 hours (Rf=0.29 in EtOAc on $SiO_2$). The reaction mixture was then concentrated and the residue was purified by silica gel chromatography, eluting with EtOAc, to provide 32 mg (52%) of the desired benzyl urea 2.

FINAL PRODUCTS

Example 13

Synthesis of Compound 1

B.

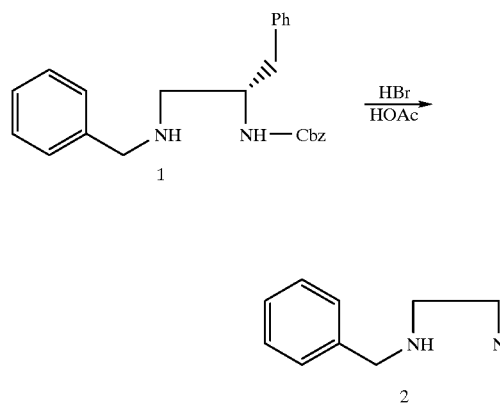

The Cbz protected diamine 1 (120 mg, 0.32 mmol) was stirred in 2.0 mL of 30% HBr in acetic acid for one hour. This was followed by concentration in vacuo. The crude oil was then dissolved into toluene and concentrated in vacuo two times followed by evacuation at approx. 1 mm Hg. The crude diamine was then purified by silica gel chromatography, eluting with 95:5:1, $CH_2Cl_2$:MeOH:$NH_4OH$ to provide 71 mg (90%) of the desired diamine 2.

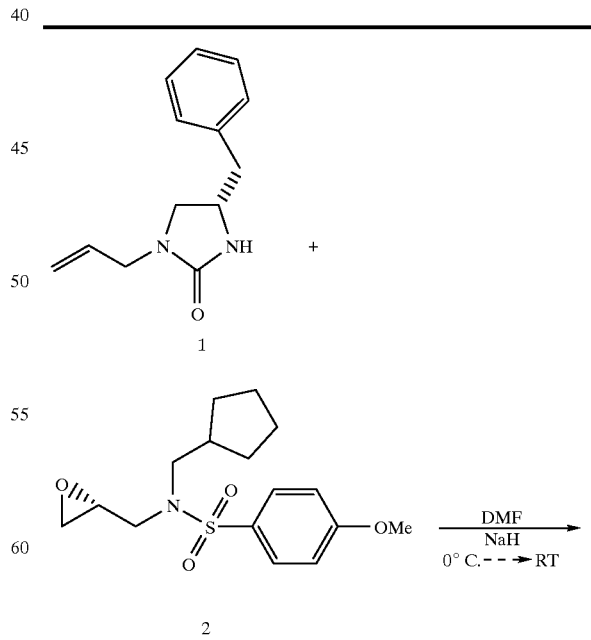

-continued

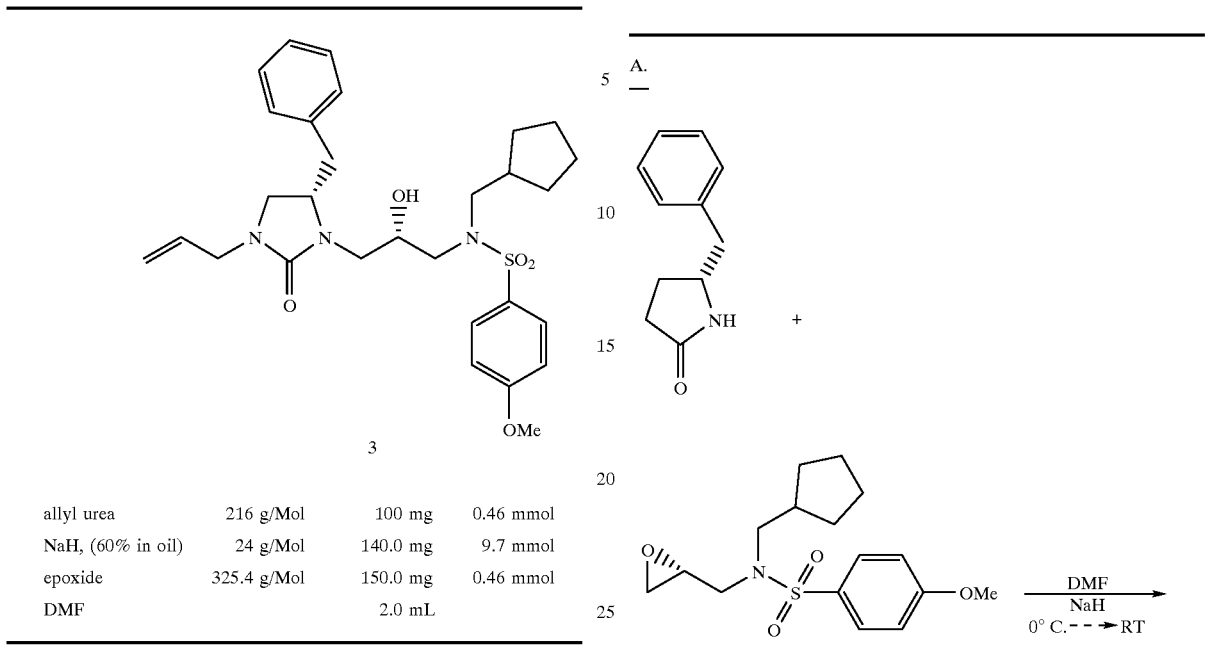

| | | | |
|---|---|---|---|
| allyl urea | 216 g/Mol | 100 mg | 0.46 mmol |
| NaH, (60% in oil) | 24 g/Mol | 140.0 mg | 9.7 mmol |
| epoxide | 325.4 g/Mol | 150.0 mg | 0.46 mmol |
| DMF | | 2.0 mL | |

The urea of Example 1C. was dissolved in 1.0 mL of anhydrous DMF and cooled to 0 ° C. This was followed by the addition of 140 mg NaH. The reaction turned darker over the next hour at 0° C. This was followed by the dropwise addition of the epoxide as a solution in DMF (0.6 mL), washing with 300 uL of DMF. The reaction was then stirred one hour at 0 ° C., followed by warming to 25 ° C. Tlc indicated nearly complete conversion to two new products (Rf=0.4 and 0.45 on $SiO_2$ with 2:1 hexane:ethyl acetate, between that of the epoxide and the urea). The reaction was then cooled to 25° C. and quenched by the addition of 3 mL of saturated sodium bicarbonate. The reaction mixture was then diluted by 15 mL of methylene chloride and washed by both saturated sodium bicarbonate and brine, (2×15 mL each). The organic portions were then dried over sodium sulfate, filtered and concentrated in vacuo. The crude product was then purified by silica gel chromatography, eluting with 80% ethyl acetate:hexane to provide 35.0 mg of the desired alcohol.

Example 14

A.

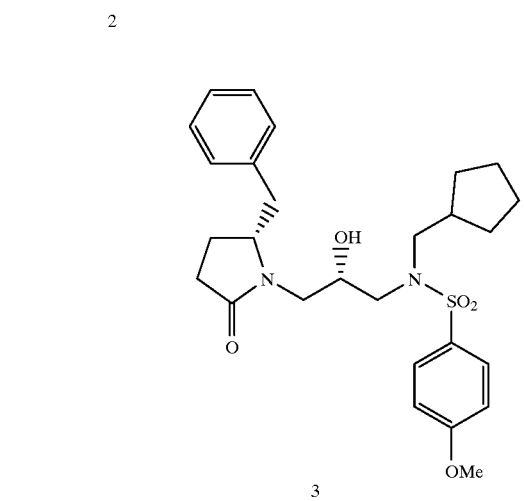

| | |
|---|---|
| 1 lactam | 1.0 equiv., 295 mgg |
| 2 sulfonamide epoxide | 1.1 equiv., 520 mg |
| 3 NaH, 60% in oil (Aldrich) | 1.5 equiv, 102 mg |
| 4 DMF | 8 mL |

A.

Lactam 1 was dissolved in 3 mL of DMF and cooled to 0° C. To this solution was then added sodium hydride as a solid and the reaction was stirred for 40 min. at 0° C. The anion solution was canulated into a solution of epoxide 2 in 3 mL of DMF. The reaction was stirred at 0° C. for 5 minutes, then warm to room temperature and stirred overnight (TLC (95:5, CH$_2$Cl$_2$:MeOH) Rf (st mat.)=0.26. Rf(prod)=0.46). After 22 hours, the reaction was cooled to 0° C., and quenched with H$_2$O/EtOAc. The organic layer was washed with water(5x) and brine, dried (MgSO$_4$), filtered, and concentrated in vacuo. The residue was then purified by silica gel chromatography (40% ether/CH$_2$Cl$_2$) to yield product 3 (310 mg, 37%)

Example 15

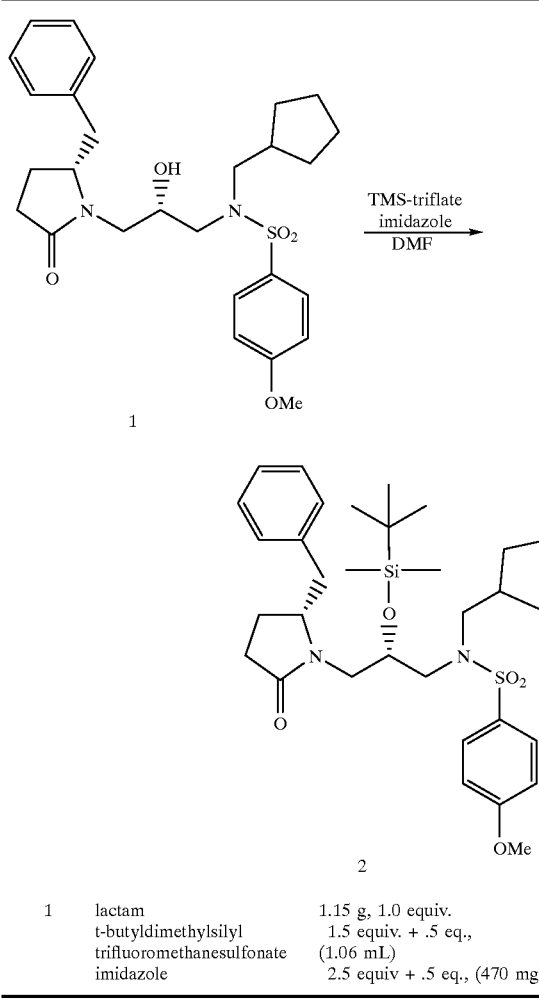

| 1 | lactam | 1.15 g, 1.0 equiv. |
| | t-butyldimethylsilyl trifluoromethanesulfonate | 1.5 equiv. + .5 eq., (1.06 mL) |
| | imidazole | 2.5 equiv + .5 eq., (470 mg) |

Lactam 1 was dissolved in 5 mL of DMF and cooled to 0° C. To this solution was then added imidazole followed by TBDMS-triflate. The reaction was then allowed to warm to room temperature. After approximatly 2 hours, an additional 0.5 eq.(80 mg) of TBDMS-triflate and 0.5 eq. (265 uL) of imidazole was added and the reaction was stirred overnight. The reaction was quenched with saturated NaHCO$_3$ solution and partitioned between H$_2$O/EtOAc. The organic layer was washed with water(5x) and brine, dried (MgSO$_4$), filtered, and concentrated in vacuo to yield product 2 (1.5 gr,37%) which was used as is.

Example 16

Synthesis of Compound 7

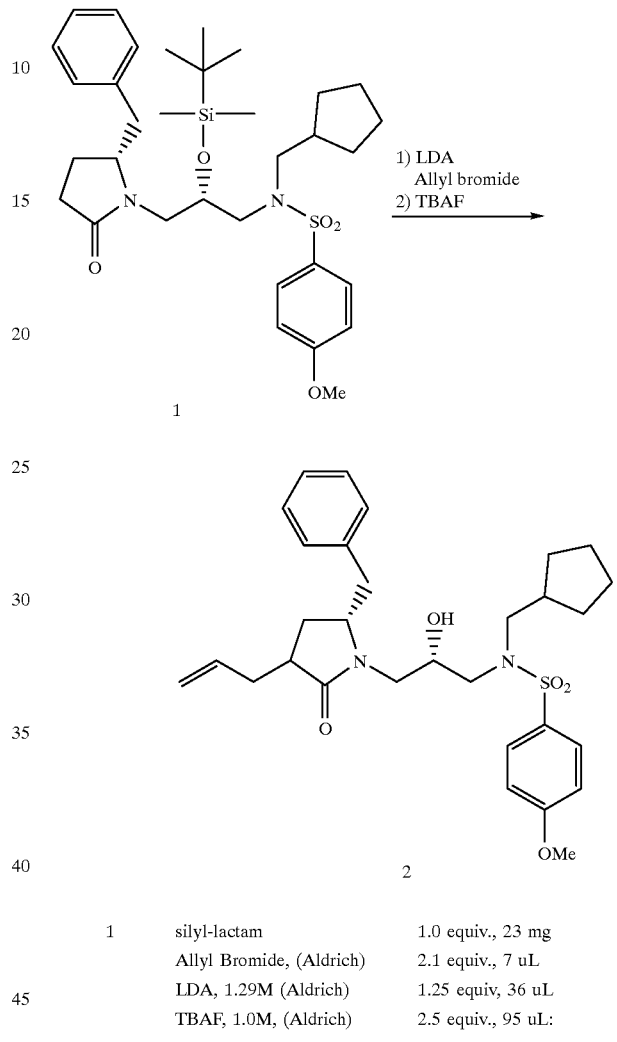

| 1 | silyl-lactam | 1.0 equiv., 23 mg |
| | Allyl Bromide, (Aldrich) | 2.1 equiv., 7 uL |
| | LDA, 1.29M (Aldrich) | 1.25 equiv, 36 uL |
| | TBAF, 1.0M, (Aldrich) | 2.5 equiv., 95 uL: |

Silyl protected lactam 1 was dissolved in THF and cooled to −78° C. To this solution, was added LDA (1.25 eq) via syringe. After stirring for 30 minutes at −78° C., allyl bromide was added via syringe. After 2 hours an additional 2 ul of allyl bromide was added and the reaction was stirred at −78° C. for 2.5 hours, then warmed to room temp for 17 hours (TLC (2:8, ether:CH$_2$Cl$_2$) Rf (st mat.)=0.56. Rf(silyl-prod)=0.72). After this time, TBAF (1M in THF) was added and the reaction was stirred at room temperature for 7 hours (TLC (1:9, ether:CH$_2$Cl$_2$) Rf (prod)=0.20). The reaction mixture was then partitioned between H$_2$O/EtOAc and the organic layer was washed with water and brine, dried (MgSO4) and filtered concentrated in vacuo. The residue was then purified by silica gel chromatography (10% ether/methylene chloride) to yield product 2 (6 mg, 30% yield)

Example 17

Synthesis of Compound 20

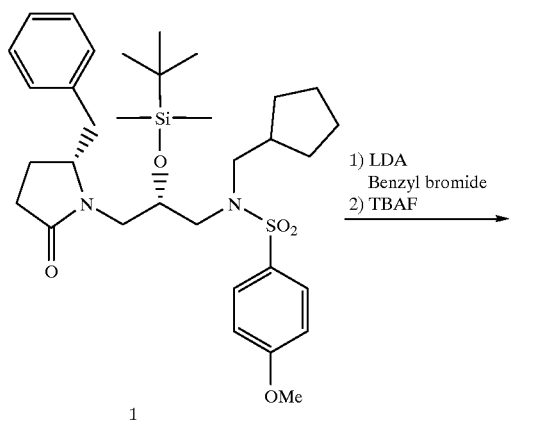

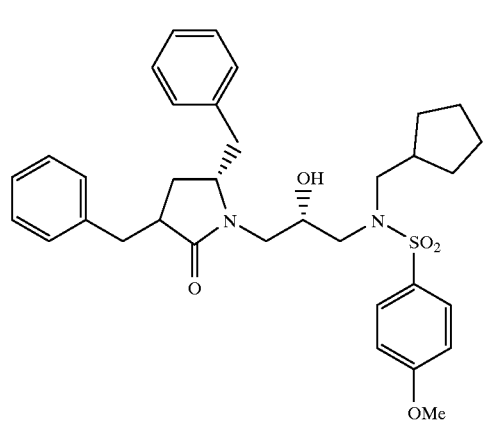

| 1 | silyl-lactam | 1.0 equiv., 122 mg |
|---|---|---|
|   | benzyl bromide, (Aldrich) | 1.5 equiv., 42 uL |
|   | LDA, 1.29M (Aldrich) | 1.4 equiv, 275 uL |
|   | TBAF, 1.0M, (Aldrich) | 2.5 equiv., 625 uL |

Silyl lactam 1 was dissolved in dry THF (6 mL) and cooled to −78° C. To this solution was then added LDA and the reaction was stirred for 30 minutes at −78° C. after which time benzyl bromide was added via syringe. The reaction was stirred at −78° C. until reaction was complete (1.5 hours, TLC (1:9, ether:CH$_2$Cl$_2$) Rf (st mat.)=0.29. Rf(silyl-prod)=0.62. Rf(BzBr)=0.79). The reaction was then quenched at −78° C. with 6 uL water and then TBAF (1M in THF was added and the reaction was warmed to room temperature and stirred for 3 hours (TLC (1:9, ether:CH$_2$Cl$_2$) Rf(prod)=0.28). The reaction was partition betweem H$_2$O/EtOAc and the organic layer was washed with with water and brine, dried (MgSO$_4$) and filtered and concentrated in vacuo. The residue was purified by silica gel chromatography (10% ether/CH$_2$Cl$_2$) to yield benzyl product 2 (71 mg, 48%).

Example 18

Synthesis of Compound 16

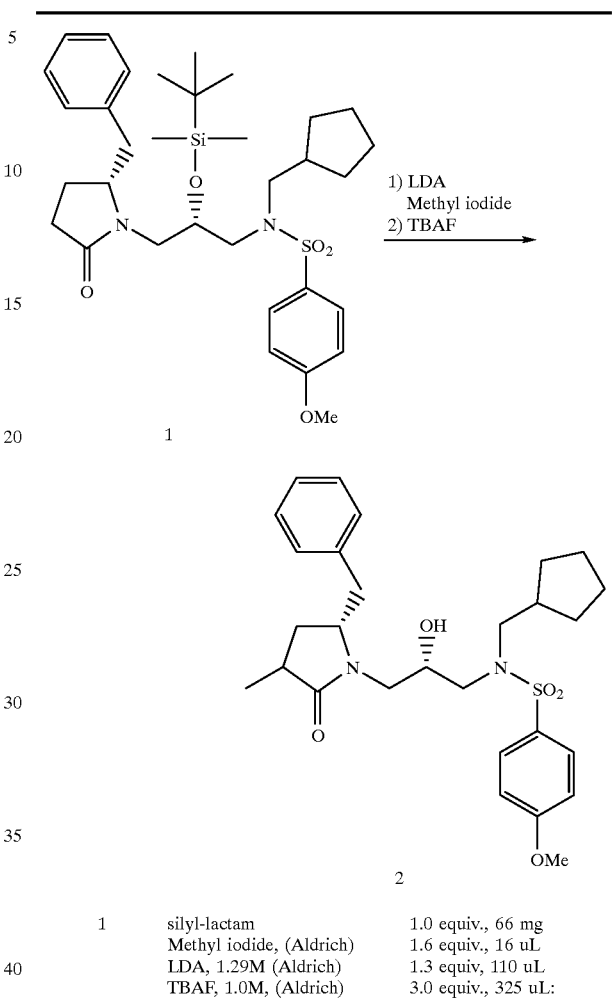

| 1 | silyl-lactam | 1.0 equiv., 66 mg |
|---|---|---|
|   | Methyl iodide, (Aldrich) | 1.6 equiv., 16 uL |
|   | LDA, 1.29M (Aldrich) | 1.3 equiv, 110 uL |
|   | TBAF, 1.0M, (Aldrich) | 3.0 equiv., 325 uL: |

The reaction for the above methylated compound was carried out as per the procedure described for compound 20 (Example 17) substituting methyl iodide for benzyl bromide on the scale described in the above table. The final compound was purified by silica gel chromatography using 10% ether/CH$_2$Cl$_2$ to yield methylated product 2 (33 mg, 60% yield)

Example 19

A.

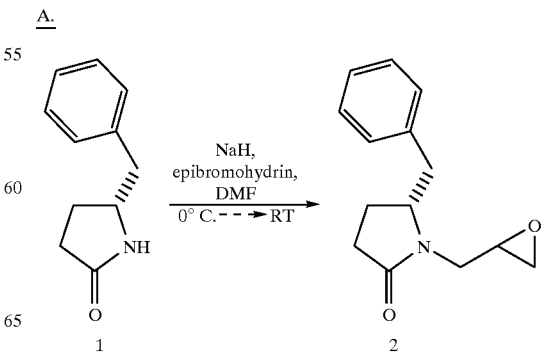

| 1 | lactam | 1.0 equiv., 400 mg |
|---|---|---|
|   | epibromohydrin | 1.5 equiv., 280 uL |
|   | sodium hydride, 80% oil disp. | 2.0 equiv, 126 mg |
|   | DMF | 15 mL |

Lactam 1 was dissolved in dry DMF (15 mL) and cooled to 0° C. under a nitrogen atmosphere. To this solution was added sodium hydride (2 eq) in one portion and the reaction was stirred at 0° C. for 1 hour after which, epibromohydrin was added via syringe. After stirring for 5 min. at 0° C. the reaction was warmed to room temperature (TLC (EtOAc) Rf (st mat.)=0.16. Rf(prod)=0.23). After 1.5 hours at room temperature the reaction was quenched with saturated $NH_4Cl$ and extracted with $CH_2Cl_2$. The organic layer was then washed with water(4×) and brine, dried (MgSO4) and filtered, and concentrate in vacuo. The residue was then purified by silica gel chromatography (3:1 EtOAC:hexane) to yield 315 mg (60%) of epoxide product 2 which was used as is in the next step.

B.

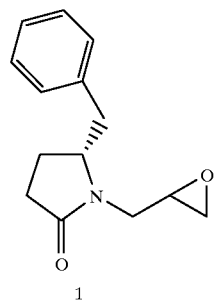

cyclopentylmethylamine,
EtOH
—————→
80° C.

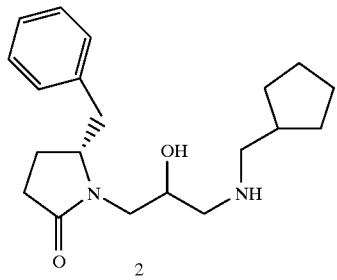

| 1 | lactam | 1.0 equiv., 315 mg |
|---|---|---|
|   | cyclopentylmethylamine | 5.75 equiv., 775 mg |
|   | anhy. EtOH | 3 mL |

Epoxide 1 was dissolved in 3 mL of EtOH and to this solution was added cylcopentylmethylamine. The reaction was heated to 80° C. for 2.5 hours (TLC (9:1, $CH_2Cl_2$:MeOH) Rf (st mat.)=0.56. Rf(prod)=0.13). The solvent was removed in vacuo and the residue was purified by silica gel chromatography (3% MeOH/$CH_2Cl_2$ to 10% MeOH/$CH_2Cl_2$) to yield 224 mg(50%) of amine product 2.

C. Synthesis of Compound 15

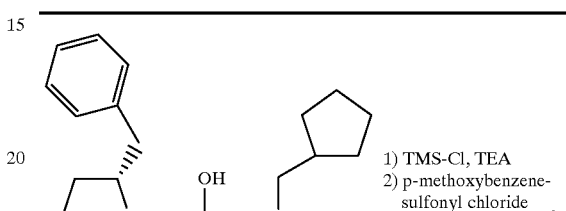

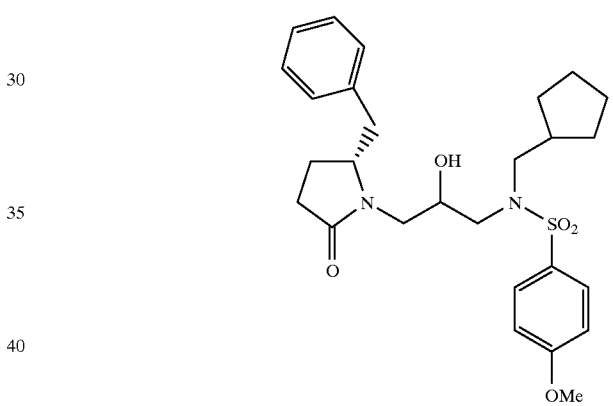

| 1 | lactam | 1.0 equiv., 315 mg |
|---|---|---|
|   | chlorotrimethylsilane | 2.2 equiv., 112 uL |
|   | triethylamine | 5.0 equiv., 280 uL |
|   | 4-methoxybenzenesulfonylchloride | 1.5 equiv., 124 mg |
|   | TBAF, 1.0M | 4.4 equiv., 1.78 mL |

Amine 1 from Example 19B was dissolved in methylene chloride and cooled to 0° C. To this solution was added triethylamine (2.5 eq) followed by chlorotrimethylsilane. The reaction was then warmed to room temperature and stirred under nitrogen for 2.0 hours. An additional amount of triethylamine was added (2.5 eq) and 4-methoxybenzenesulfonyl chloride was added. The reaction was stirred at room temperature for 3 hours. After this time, TBAF (1M in THF) was added and the reaction stirred at room temperature for 1 hour. The solvent was removed in vacuo. and the residue partitioned between ethyl acetate and aqueous saturated bicarbonate solution. The organic layer was washed with water, brine, dried $MgSO_4$, filtered and the solvent removed in vacuo. (TLC (8:2, $CH_2Cl_2$:ether), Rf(upper diast.)=0.21 Rf(lower diast.)=0.12). The residue was purified by silica gel chromatography (25% ether/$CH_2Cl_2$) to yield 52 mg (26%) of (upper diastereomer). The lower diastereomer was further purified by preperative TLC (1:1, ether:$CH_2Cl_2$) to give 23 mg (12%) of the lower diastereomer.

Example 20

Synthesis of compound 47

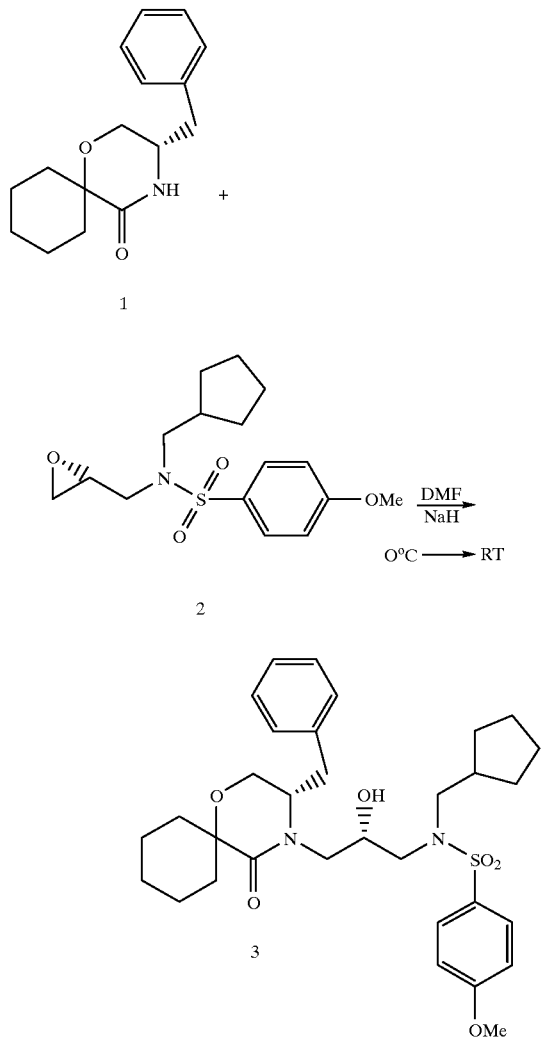

Morpholinone 1 was dissolved in 1 ml of anhydrous DMF, cooled to 0 C. and to this solution was added 4.4 mg of NaH. The solution was brought to room temperature for 30 min and then cooled down to 0 C before adding 0.20 g of epoxide 2. After heating for 5 hrs at 45° C., the solvent was removed in vacuo and purified on silica gel yielding 111 mg of final product 2 (compound 47). M (ES+)=585 (M+1), 607.1 (M+Na). 1H NMR (CDCl3)=7.52 (d, 2H), 7.30 (m, 5H), 6.95 (d, 2H), 4.05 (m, 1H), 3.87 (3H, s), 3.60 (m, 2H), 3.16 (m, 4H), 3.0 (m, 4H), 2.18 (1H, m), 1.97 (m, 2H), 1.60 (m, 14H), 1.23 (m, 4H).

Example 21

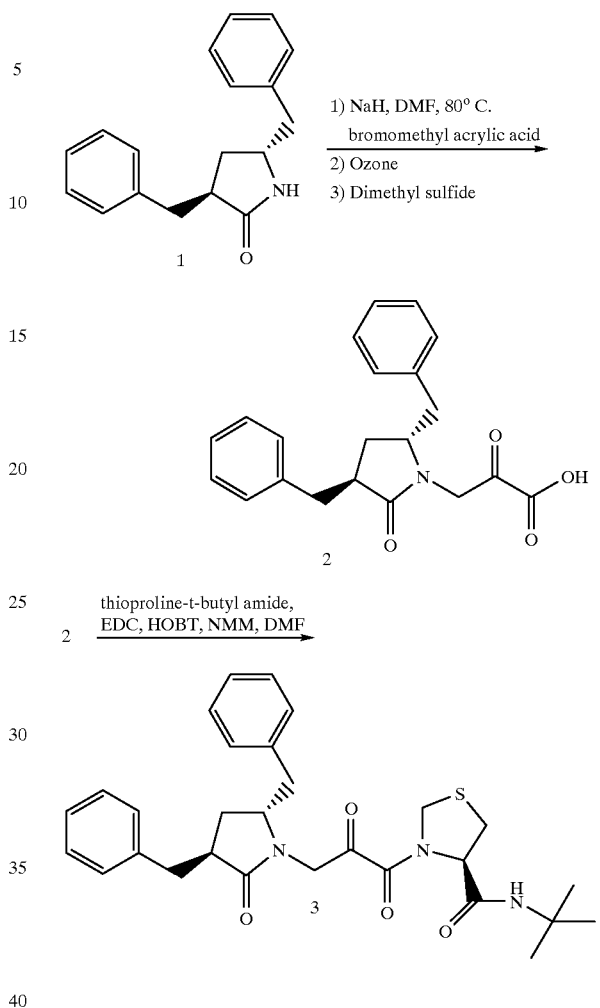

To a cooled solution (−78° C.) of benzyl lactam 1 (0.150 g, 0.57 mmol) and bromomethyl acrylic acid (0.094 g, 0.57 mmol) in anhydrous THF (4.0 mL) was added NaH (60%, 0.046 g, 1.14 mmol) with stirring. The solution was allowed to gradually warm to room temperature and stir for 1.5 h. The reaction mixture was then diluted with ethyl acetate (60 mL) and washed with 1.0N HCl (2×10 mL) and brine (2×10 mL). The organic layer was dried (magnesium sulfate), filtered, and evaporated to give an off white solid. This solid was dissolved in methylene chloride/methanol (80/20, 10 mL) and through the cooled solution (−78° C.) was bubbled ozone for 10 min. The solution was flushed with oxygen, warmed to 0° C., and methyl sulfide (2.0 mL) was added at 0° C. The mixture was allowed to warm to room temperature and stand for 1.0 h. Evaporation of the solvent afforded crude product 2 as a yellow oil. To a solution of the acid 2 in anhydrous DMF (3.0 mL) was added thioproline-t-butylamide (0.11 g, 0.57 mmol), hydroxybenzotriazole (0.77 g, 0.57 mmol), N-methyl-morpholine (0.62 mL, 0.57 mmol) and EDCI (0.11 g, 0.57 mmol) respectively with stirring at room temperature. After 24 h. at room temperature, the reaction mixture was evaporated and the residue was dissolved in ethyl acetate (100 mL). The solution was washed with 1.0N HCl (2×20 mL), 10% sodium carbonate (2×20 mL), water (1×10 mL), brine( 1×10 mL), filtered and evaporated to give 0.210 g of a yellow oil. The oil was purified by column chromatography; hexane/ethyl acetate (60/40) to give compound 3 (0.050 g, 18%) MS:M+1=522; H NMR (chloroform-d) 1.35(d, 9H); 1.85(m,2H); 2.6(m, 3H); 2.85(m,1H); 3.15(m,2H); 3.40(m,1H); 3.8(m,1H); 4.1 (m, 2H); 4.4(m,1H); 4.70(m,1H); 4.95(m, 1H); 6.1(d, 1H); 7.1 (m, 4H) ; 7.25 (m, 6H)

Example 22

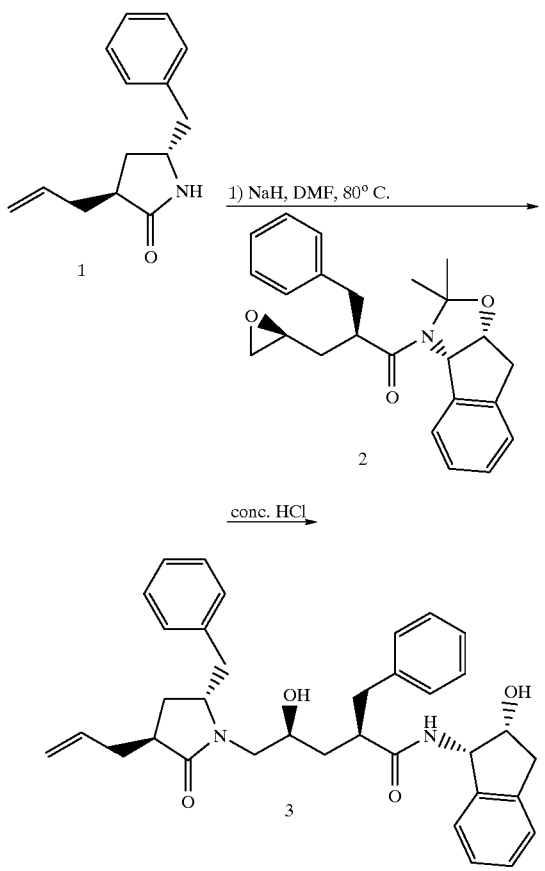

0.80 g of allyl lactam 1 was dissolved in 1 ml of DMF, cooled to 0° C. and 89.5 mg of sodium hydride was then added. The solution was then brought up to ambient temperature for 30 min, again cooled down to 0° C. and 1.4 g of epoxide 2 was added. The reaction was warmed to 50° C. under $N_2$ blanket for 3 hrs. The resulting crude mixture was then chromatographed on silica gel yielding 1.4 g of 3 (63.7%). This amount was treated with 12 ml of 4N HCl in dioxane and 2 ml water for 30 min. The product was then chromatographed on C18rphplc, yielding 0.36 g of two diastereomers, subjected to chiral separation, which resulted in 138 mg of pure diastereomer 3. MS (ES–551.3 (M–1)), ES+, 553.3 (M+1) and 575.3 (M+Na). 1H NMR (CDCl3)= 7.20 (m, 14H), 6.26 (m, 1H), 5.62 (m, 1H), 5.24 (m, 1H), 4.97 (m, 2H), 4.23 (m, 1H), 3.83 (m. 2H), 3.61 (m, 1H), 2.95 (m, 10H), 2.40 (m, 1H), 2.24 (m, 1H), 2.04 (m, 1H), 1.95 (m, 2H), 1.70 (m, 2H).

Example 23

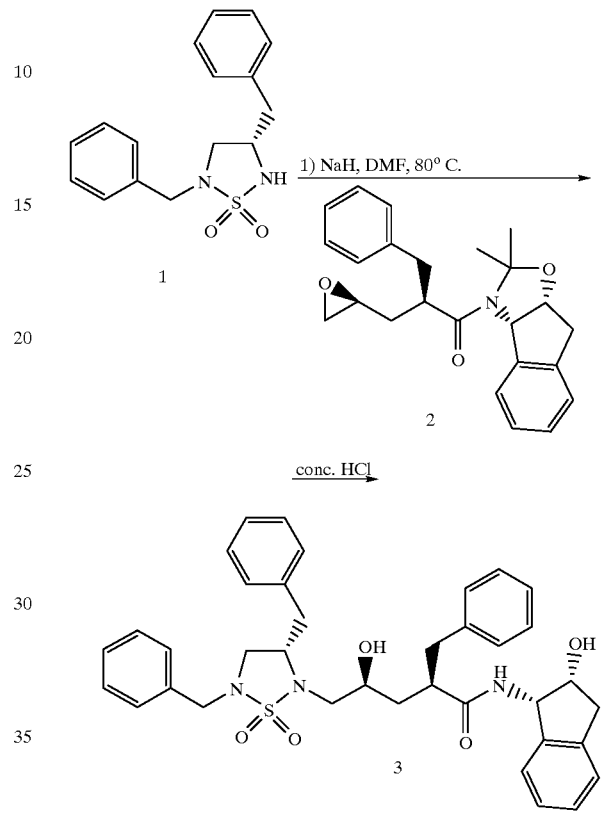

A solution of cyclic sulfamate 1 (0.1 g, 0.33 mmol) in 2 mL of dimethyl formamide was cooled to 0° C. and treated with of 60% sodium hydride (0.005 g, 0.13 mmol) in oil. The mixture was stirred at 25° C. for 1.5 h and treated with of epoxide 2 (0.125 g, 0.33 mmol). The resulting mixture was stirred at 60° C. for 3 h, more sodium hydride (0.005 g) was added and heating was continued over night. The volatiles were removed in vacuo and the residue was dissolved in 2 mL of 4M hydrogen chloride in 1,4-dioxane. Water (0.5 mL) was added and the mixture was stirred for 6 h at 25° C. The reaction mixture was diluted with ethyl acetate and extracted with 10% soduim bicarbonate. Drying over magnesium sulfate and removal of the solvents gave a yellow gum, which was subjected to C-18 preparative HPLC (acetonitrile-water gradient). The desired material 3 was isolated as a minor fraction (9 mg) as a white solid 1H-NMR (CDCl3): 2.10(2H), 2.70(2H), 2.8–3.2(8H), 3.4(1H), 3.58 (1H), 4.02(1H), 4.15(1H), 4.22(2H), 5.30(1H), 5.86(1H), 7.06(2H), 7.1–7.4(16H).

Example 24

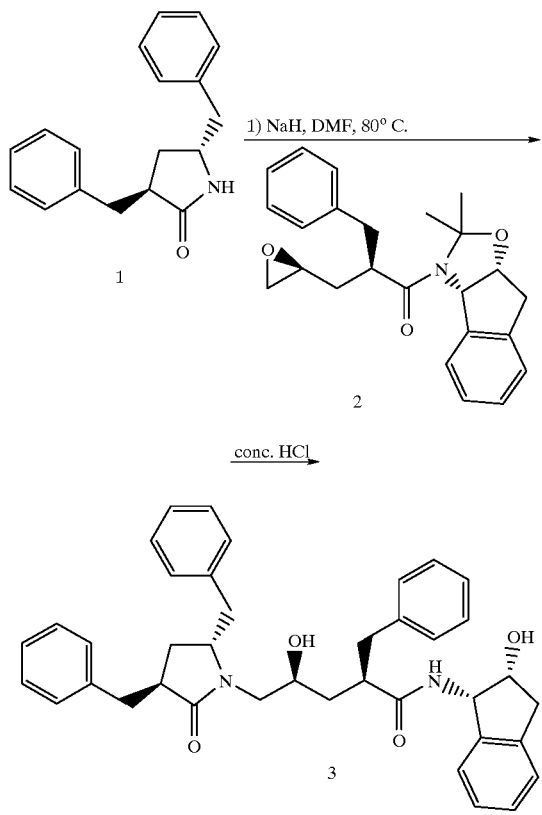

To a cooled solution (0° C.) of compound 1 (0.190 g, 0.72 mmol) in anhydrous DMF (10 mL) was added NaH(60%, 0.028 g, 0.72 mmol) with stirring. The solution was allowed to warm to room temperature and stir for 1.0 h. Compound 2 (0.275 g, 0.73 mmol) was added at room temperature and the mixture was heated at 60° C. for 5.0 h. The solution was evaporated and the reside was partioned between ethyl acetate (150 mL) and water (30 mL). The organic layer was washed with water (2× 10 mL), brine (25 mL), dried (MgSO$_4$), filtered, and evaporated to give a grey oil. The oil was purified by column chromatography:hexane/ethyl acetate (60/40) to give 0.23 g (50%) of the acetonide protected product. The acetonide (0.185 g, 0.29 mmol) was dissolved in isopropanol (10 mL) and treated with conc. HCl (3.0 mL) at room temperature. After 1.5 h., the solution was adjusted to pH 11 with 3.0N NaOH and then concentrated. The aqueous solution was extracted with ethyl acetate (3×75 mL). The ethyl acetate was dried (MgSO$_4$) and evaporatated to give a clear film. The crude product was purified by column chromatography:hexane/ethyl acetate (45/55) to give the product as a white solid (0.090 g, 50%). Preparative HPLC on chiral phase (isopropanol-hexane gradient) yielded the desired diastereomer 3 (10 mg) along with a 1:1 mixture of the desired diastereomer and an additional epimer (50 mg). MS:M+1=603 H NMR (chloroform-d) 1.80(m, 6H); 2.50(m,1H); 2.60(m, 2H); 3.0(m,8H); 3.60(m,1H); 3.70(m,1H); 3.95(m,1H); 4.25(m,1H); 5.30(m,1H); 6.00(m, 1H); 7.05(m,4H); 7.25(m,15H).

Example 25

A.

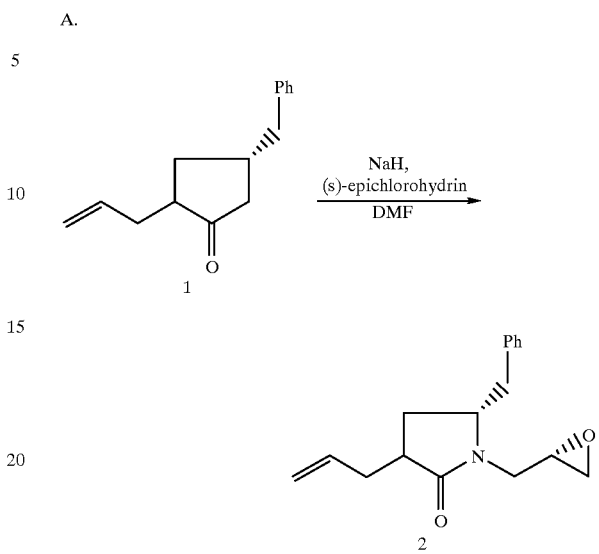

Allyl lactam 1 (443 mg, 2.06 mmol) was dissolved in DMF (2 mL) and to this solution was added sodium hydride (2.2 mmol). The reaction mixture was stirred at room temperature for 1 hr after which (s)-epichlorohydrin (172 ul, 2.2 mmol) was added neat. The reaction was stirred at room temperature for 4 hr, diluted with water (20 mL) and extracted with ethyl acetate. The organic layer was then washed with water, brine and dried (MgSO$_4$) and filtered. Concentration in vacuo afforded crude epoxide product 2 which was used without further purification.

B.

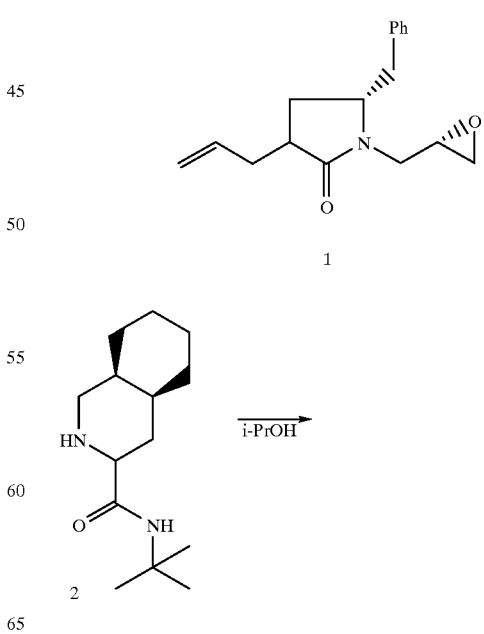

Example 26

A.

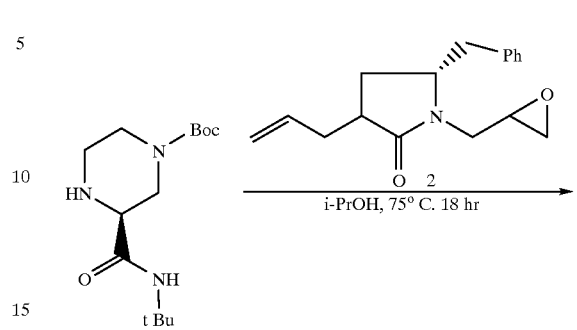

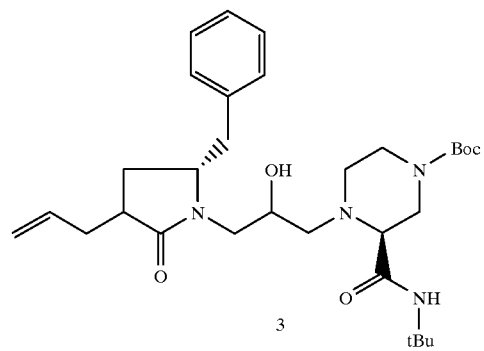

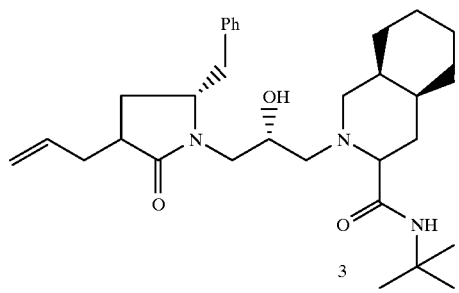

Lactam epoxide 1 (180 mg, 0.66 mmol) and decahydroisoquinoline 2 (160 mg, 0.66 mmol) were heated to 80° C. in isopropanol. After three hours the reaction was cooled to 25° C. and stirred for 48 hours at room temperature. The reaction was then concentrated in vacuo. Purified by silica gel chromatography, eluting with 25% EtOAc:Hexanes, providing 90 mg (90% pure by HPLC) of desired product 3.

The Boc protected piperazine 1 (21.4 mg, 0.081 mmol), was dissloved in 1.5 mL of i-PrOH. This was followed by the addition of the lactam epoxide 2 (18.3 mg, 0.068 mmol). The reaction vessel was then fitted with a reflux condenser and heated to 75° C. for 16 hours. TlC indicated complete consumption of both starting materials and formation of a new material. The reaction was then cooled to 25° C. and concentrated in vacuo. The complete consumption of epoxide was confirmed by both tlc and ¹H NMR. The crude addition product was then used without further purification.

B.

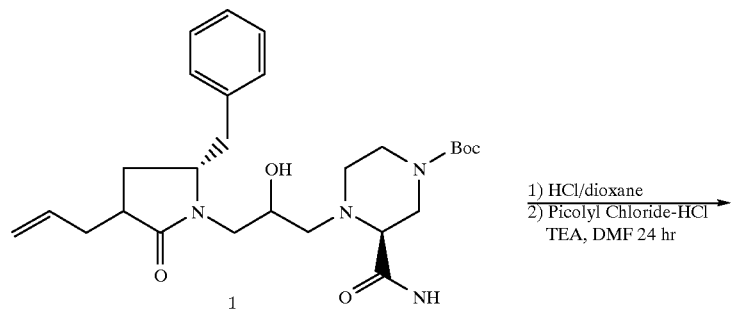

-continued

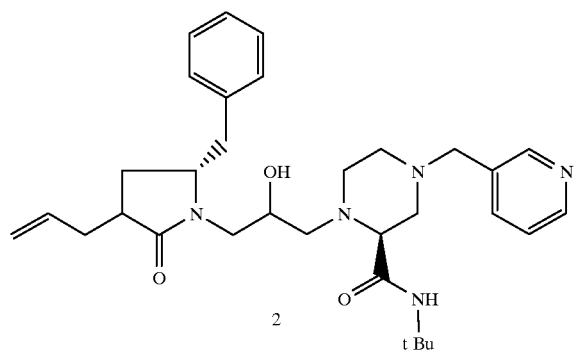

The Boc protected piperazine addition product 1 from the previous step was stirred for 2 hours in 1.0 mL of 4N HCl/dioxane. This was followed by concentration in vacuo. The crude solid was then dissolved in 10 mL of $CH_2Cl_2$ and washed by 2x10 mL of each saturated aqueous sodium bicarbonate and saturated aqueous brine. The combined organic portions were then dried over $MgSO_4$, filtered and concentrated in vacuo to provide the freebase of the desired intermediate. The crude amine was then dissolved in 1.0 mL of DMF at 25° C. This was followed by the addition of the hydrochloride salt of 3-picolyl chloride (0.081 mmol). After stirring 5 minutes triethylamine (300 uL, mmol) was added. The reaction was then stirred for 36 hours the reaction was quenched by the addition of 1.0 mL of saturated aqueous sodium bicarbonate. The reaction mixture was then diluted by the addition of 10 mL of diethyl ether and washed by 2x10 mL of each saturated aqueous sodium bicarbonate and saturated aqueous brine. The combined organic portions were then dried over $MgSO_4$, filtered and concentrated in vacuo to provide the crude product. Purification of the crude solid was carried out by silica gel chromatography (1000 uM $SiO_2$ prep. plate) eluting with 20% $MeOH/CH_2Cl_2$. This provided 3.1 mg of the desired product 2, with 96% purity by HPLC. The overall yield for addition, deprotection of N-Boc and coupling with 3-picolyl chloride was 9%.

Example 27

A.

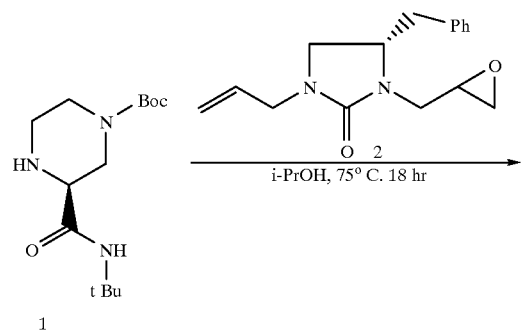

Allyl urea 1 (195.2 mg, 0.09 mmol) was dissolved in 6.0 mL of DMF and cooled to 0° C. This was followed by the addition of NaH (54 mg, 1.0 mmol). The glycidyl tosylate (410 mg, mmol) was then added as a solid. The reaction was stirred for 4 hours at 25° C. and then quenched by the addition of 4 mL of saturated aqueous sodium bicarbonate. The reaction was then extracted by 10 mL of $Et_2O$. The organic layer was then washed by 10 mL of saturated aqueous sodium bicarbonate and 2x10 mL of saturated brine. The combined organic portions were then dried over MgSO4, filtered and concentrated in vacuo to provide the desired epoxide 2 (180 mg, 73% yield). The epoxide was then used without further purification.

B.

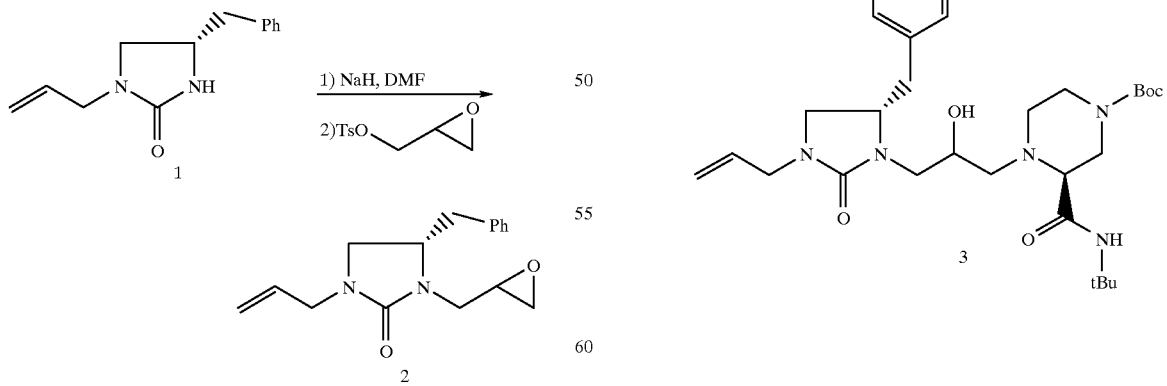

Piperazine 1 (25.7 mg mmol) and epoxide 2 (22.6 mg, mmol) were heated to 75° C. in 1.5 mL of i-PrOH for 18 hours. After cooling to 25° C. the crude reaction mixture was concentrated in vacuo. Complete consumption of the epoxide was apparent by both tlc and $^1H$ NMR.

C.

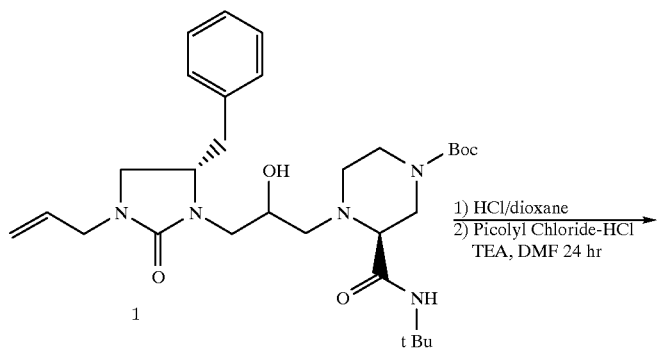

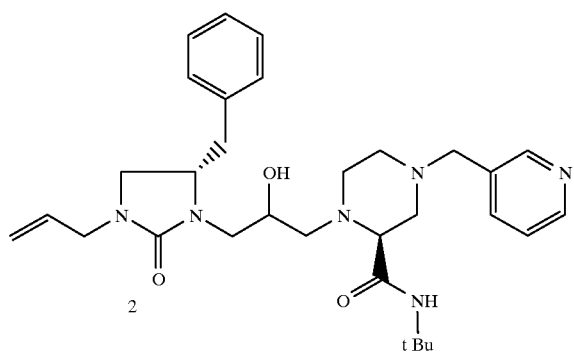

The Boc protected piperazine 1 from the previous step was stirred for 1.5 hours in 1.0 mL of 4N HCl in dioxane. This was followed by concentration in vacuo. The crude hydrochloride salt was then dissolved in 10 mL of CH$_2$Cl$_2$ and washed by 10 mL of both saturated sodium bicarbonate and saturated brine. The organic portion was then dried over MgSO$_4$, filtered and concentrated in vacuo. The free amine was then taken up in 1 mL of DMF. This was followed by the addition of 3-picolyl chloride HCl salt (50 mg, mmol) and triethyl amine (300 uL), respectively. The reaction was then stirred at 25° for 30 hours. The reaction was then quenched by the addition of 2 mL of saturated sodium bicarbonate and diluted by 10 mL of Et$_2$O. The organic portion was then washed by 10 mL of saturated sodium bicarbonate and 2×10 mL of saturated brine. The combined organic portions were then dried over MgSO$_4$, filtered and and concentrated in vacuo. The crude material was purified by silica gel chromatography (1000 uM prep. plate) eluting with 3:1, CH$_2$Cl$_2$:MeOH to provide 8.8 mg of the desired product 2. The overall yield for addition, deprotection of the N-Boc and reaction with 3-picolyl chloride was 19.3%.

Example 28

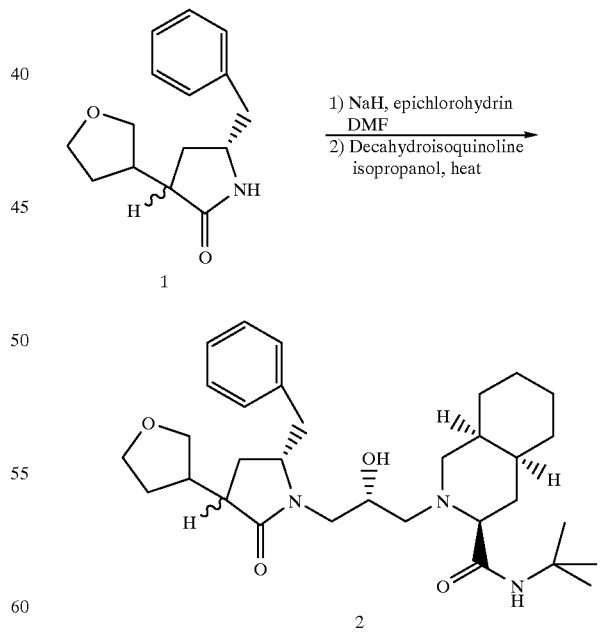

The THF lactam 1 (0.4 mmol) was dissolved in dry DMF at 0° C. and to this solution was added sodium hydride (0.47 mmol). After 30 min of stirring, (s)-epichlorohydrin (0.47 mmol) was added and the reaction was allowed to warm to room temperature and stir overnight. The reaction was then diluted with water and extracted with ethyl acetate. The organic layer was washed sequentially with 0.5N HCl, saturated NaHCO$_3$ and brine, followed by drying (MgSO$_4$), filtration and concentration in vacuo to yield product (118 mg, crude) which was used as is. The lactam-epoxide (0.4 mmol, crude) was dissolved in isopropanol (2 mL), and to this solution was added decahydroisoquinoline t-butylamide (0.7 mmol). The mixture was then heated to 80° C. and stirred overnight. The reaction mixture was cooled and concentrated to dryness in vacuo, the residue of which was applied to a preperative TLC plate and eluted with 100% ethyl acetate to yield pure product (88 mg, 42%) as a mixture of diastereomers.

Example 25

Using the method described by Pennington et al. (supra), we obtained inhibition constants for the following compounds of this invention:

| Compound | K$_i$ (nM) |
|---|---|
| 1 | 160 |
| 2* | 180 |
| 3* | 1,800 |
| 5* | >10,000 |
| 6* | >10,000 |
| 7 | 9 |
| 8* | 5 |
| 9* | 90 |
| 10 | >10,000 |
| 11 | >10,000 |
| 12 | >10,000 |
| 13 | 225 |
| 14 | 16 |
| 15 | 550 |
| 16 | 56 |
| 17 | 115 |
| 18 | 15 |
| 19 | 3,000 |
| 20 | 1.5 |
| 21 | >20,000 |
| 22 | 600 |
| 23 | 70 |
| 24 | 350 |
| 25 | 83 |
| 26 | 58 |
| 27 | 3,000 |
| 28 | 1,400 |
| 30 | >15,000 |
| 31 | 390 |
| 32 | 160 |
| 33 | 1,100 |
| 34 | 950 |
| 35 | 130 |
| 36 | >20,000 |
| 37 | >20,000 |
| 38 | 17 |
| 39 | 600 |
| 40 | >20,000 |
| 41 | >20,000 |
| 42 | 330 |
| 43 | >10,000 |
| 44 | 120 |
| 45 | 30 |
| 46 | >10,000 |
| 47 | 20 |
| 50* | 100 |
| 51* | 90 |
| 52* | 1,100 |
| 54* | 12 |
| 55* | 30 |
| 56* | 280 |
| 57* | 460 |
| 58* | 5,300 |
| 59* | >8,000 |
| 60* | 170 |
| 61* | >1,000 |
| 62* | 120 |
| 63* | 200 |
| 64* | >5,000 |
| 65* | 2,906 |
| 66* | 1,300 |
| 67* | 3,900 |
| 68* | >10,000 |
| 69* | >10,000 |
| 70* | 790 |
| 71* | 2,500 |
| 72* | 85 |
| 73* | 190 |
| 74* | 1,200 |
| 76* | 250 |
| 77* | 560 |
| 78* | 10 |
| 79* | >3,000 |
| 80* | 3 |
| 82* | 15 |
| 83* | 0.50 |
| 85* | 2,600 |
| 87* | 15 |
| 88* | 270 |
| 90* | 220 |
| 91* | 12 |
| 92* | 0.3 |
| 93* | 420 |
| 94* | 1 |
| 95* | 10 |
| 98* | >10,000 |
| 102* | 1,200 |
| 105* | >10,000 |
| 109* | 250 |
| 111* | >10,000 |
| 112* | 8,600 |
| 113* | >10,000 |
| 114* | >1,000 |
| 115* | >10,000 |

*Inhibition constant measured at pH 6.0.

The above data show that each of the tested compounds inhibits HIV aspartyl protease.

While we have described a number of embodiments of this invention, it is apparent that our basic constructions may be altered to provide other embodiments which utilize the products and processes of this invention. Therefore, it will be appreciated that the scope of this invention is to be defined by the appended claims, rather than by the specific embodiments which have been presented by way of example.

We claim:

1. A compound according to formula I:

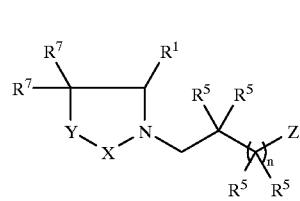

(I)

wherein:

each Z is

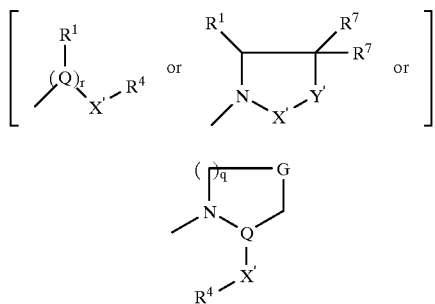

wherein any Z is unfused or fused with $R^6$;

each X and X' is independently selected from the group consisting of —C(O)—, —C(O)C(O)—, —S(O)— and —S(O)$_2$;

each Y and Y' is independently selected from the group consisting of —(C(R$^2$)$_2$)$_p$—, —NR$^2$—, —(C(R$^2$)$_2$)$_p$M—, and —N(R$^2$)—CH$_2$—;

each $R^1$ is independently selected from the group consisting of hydrogen; $R^6$; $C_1$–$C_6$ alkyl; $C_2$–$C_6$ alkenyl; $C_2$–$C_6$ alkynyl; $C_3$–$C_6$ cycloalkyl unfused or fused with $R^6$; $C_5$–$C_6$ cycloalkenyl unfused or fused with $R^6$; and where $R^1$'s are attached to adjacent atoms, the $R^1$'s together with their attached adjacent atoms form a carbocyclic or heterocyclic ring system which is unfused or fused with $R^6$; where any member of $R^1$ is unsubstituted or substituted by one or more $R^2$;

each $R^2$ is independently selected from hydrogen; $R^3$; $C_1$–$C_6$ alkyl; $C_2$–$C_6$ alkenyl; $C_2$–$C_6$ alkynyl; $C_3$–$C_6$ cycloalkyl unfused or fused with $R^6$; $C_5$–$C_6$ cycloalkenyl unfused or fused with $R^6$; and where two $R^2$'s are attached to the same geminal atom, the $R^2$'s together with their attached geminal atom form a spirocarbocyclic or spiroheterocyclic ring system, where any member of $R^2$ is unsubstituted or substituted by one or more $R^3$;

each $R^3$ is independently selected from oxo, OR$^9$, N(R$^9$)$_2$, N(R$^9$)—X—R$^9$, N(R$^9$)—X—OR$^9$, SR$^9$, X—R$^9$, O—X—N(R$^9$)$_2$, C(O)N(R$^9$)$_2$, halogen, NO$_2$, CN, COOR$^9$ and $R^6$;

each $R^4$ is independently selected from the group consisting of OR$^9$; N(R$^9$)$_2$; X—R$^9$; C(O)N(R$^9$)$_2$; $R^6$; $C_1$–$C_6$ alkyl; $C_2$–$C_4$ alkenyl; $C_3$–$C_6$ cycloalkyl unfused or fused with $R^6$; $C_5$–$C_6$ cycloalkenyl unfused or fused with $R^6$; where any member of $R^4$ is unsubstituted or substituted by one or more groups independently selected from the group consisting of $R^9$ and $R^3$;

each $R^5$ is independently selected from the group consisting of H, OH, O and $R^1$;

each $R^6$ is independently selected from the group consisting of aryl, carbocyclyl and heterocyclyl, wherein said aryl, carbocyclyl or heterocyclyl is unsubstituted or substituted with one or more groups selected from the group consisting of oxo, —OR$^9$, —R$^9$, —N(R$^9$)(R$^9$), —N(R$^9$)—X—R$^9$, SR$^9$, —X—R$^9$, —O—X—N(R$^9$)$_2$, —R$^9$—OR$^9$, —CN, —CO$_2$R$^9$, —X—N(R$^9$)(R$^9$), halogen, —NO$_2$, and —CF$_3$;

each $R^7$ is independently selected from the group consisting of hydrogen, OH and O;

each $R^8$ is independently selected from the group consisting of hydrogen, alkyl, alkenyl, alkynyl, aryl, carbocyclyl, and heterocyclyl;

each $R^9$ is independently selected from the group consisting of hydrogen, alkyl, alkenyl, alkynyl, aryl, carbocyclyl, heterocyclyl, aralkyl, carbocyclylalkyl and heterocyclylalkyl wherein any aryl, carbocyclyl or heterocyclyl is unfused or fused with $R^8$ and wherein any member of $R^8$ is unsubstituted or substituted by one or more groups independently selected from the group consisting of —OR$^8$, —N(R$^8$)$_2$, —CN, —NO$_2$, —X—R$^8$, —X—N(R$^8$)$_2$, —C(O)OR$^8$, —N(R$^8$)—XNR$^8$, and halogen;

each Q is independently selected from CH and N;

each M is independently selected from the group consisting of NH, —NR$^2$—, —O—, —S—, —S(O)— and —S(O)$_2$—;

each n is 1 or 2;

each r is 0,1 or 2;

each p is independently 1 or 2;

each q is independently 1, 2 or 3; and each G is independently selected from the group consisting of —NH—, —NR$^2$—, —O—, —S—, —S(O)—, S(O)$_2$, —C(O)— and —C(R$^2$)$_2$—.

2. The compound according to claim 1, wherein:

each Y and Y' is independently selected from the group consisting of —(C(R$^2$)$_2$)$_p$—, —NR$^2$—, —(C(R$^2$)$_2$)$_p$—M—, and —N(R$^2$)—CH$_2$—; and each $R^3$ is independently selected from oxo, OR$^9$, N(R$^9$)$_2$, N(R$^9$)—X—R$^9$, N(R$^9$)—X—OR$^9$, SR$^9$, X—R$^9$, O—X—N(R$^9$)$_2$, C(O)N(R$^9$)$_2$, halogen, NO$_2$, CN, COOR$^9$ and $R^6$.

3. The compound according to claim 1 having the structure of formula IA:

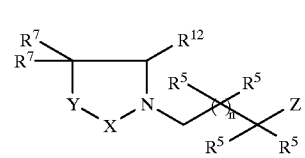

(IA)

wherein:

each $R^{12}$ is independently selected from the group consisting of $R^6$; $C_1$–$C_6$ alkyl unsubstituted or substituted with $R^6$; $C_2$–$C_6$ alkenyl; $C_2$–$C_6$ alkynyl; $C_3$–$C_6$ cycloalkyl unfused or fused with $R^6$; $C_5$–$C_6$ cycloalkenyl unfused or fused with $R^6$; wherein any member of $R^{12}$ is unsubstituted or substituted by one or more $R^2$.

4. The compound according to claim 1, wherein n is 1.

5. The compound according to claim 1 having the structure of formula II:

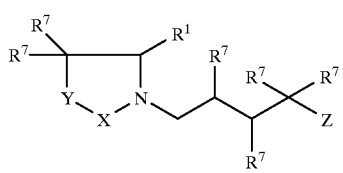

(II)

6. The compound according to claim 1 having the structure of formula III:

(III)

7. The compound according to claim 1, wherein:
X is —C(O)— or —S(O)$_2$—; and
Y is —(C(R$^2$)$_2$)$_p$—M—.
8. The compound according to claim 1, wherein:
X is —C(O)— or —S(O)$_2$—; and
Y is (—C(R$^2$)$_2$—)$_p$.
9. The compound according to claim 1, wherein:
X is —C(O)—, —C(O)C(O)— or —S(O)$_2$—; and
Y is —N(R$^2$)— or —N(R$^2$)—CH$_2$—.
10. The compound according to claim 1, having the structure of formula V:

(V)

wherein:
X is —C(O)— or —S(O)$_2$—;
Y is —(C(R$^2$)$_2$)—M—, —(C(R$^2$)$_2$)$_p$—, —N(R$^2$)— or —N(R$^2$)—CH$_2$—;
R$^{10}$ is O or H$_2$;
each R$^{11}$ is independently H, OH or O, wherein both R$^{11}$ are not simultaneously hydrogen; and
Z is a structure of formula VI:

(VI)

wherein any structure of formula VI is unfused or fused with an aryl, carbocyclic or heterocyclic ring and is unsubstituted substituted with 1–3 substituents independently selected from R$^2$.
11. The compound according to claim 10, wherein R$^{10}$ and R$^{11}$ are O.
12. The compound according to claim 11, wherein:
q is 1;
G is S; and
X' is —C(O)—.
13. The compound according to claim 12, wherein R$^4$ is t-butylamino.
14. The compound according to claim 11, wherein:
X is —C(O)—;
Y is —(C(R$^2$)$_2$)$_p$—; and
R$^7$ is H.
15. The compound according to claim 10, wherein:
X and X' is —C(O)—;
Y is —(C(R$^2$)$_2$)—;
R$^7$ is H;
R$^{10}$ is H$_2$; and
one R$^{11}$ is H and one R$^{11}$ is OH.
16. The compound according to claim 10, wherein:
X and X' is —C(O)—;
Y is —N(R$^2$)—;
R$^7$ is H;
R$^{10}$ is H$_2$; and
one R$^{11}$ is H and one R$^{11}$ is OH.
17. The compound according to claim 10, wherein:
X and X' is —C(O)—;
Y is —(C(R$^2$)$_2$)—M—;
M is O;
R$^7$ is H;
R$^{10}$ is H$_2$; and
one R$^{11}$ is H and one R$^{11}$ is OH.
18. The compound according to claim 10, wherein:
R$^{10}$ is H$_2$; and
one R$^{11}$ is H and one R$^{11}$ is OH; and
Z is selected from the group consisting of:

and R$^2$ is as defined in claim 1.
19. The compound according to claim 10, wherein Z is selected from the group consisting of R$^{10}$ is H$_2$; and
one R$^{11}$ is H and one R$^{11}$ is OH.
20. The compound according to any one of claims 15–17 wherein Z is selected from the group consisting of:

and R$^2$ is as defined in claim 1.
21. The compound according to any one of claims 15–17, wherein Z is selected from the group consisting of:

125

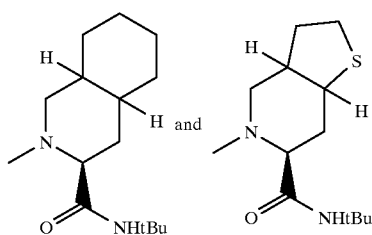

126

22. The compound according to claim 1, wherein:

Z is selected from the group consisting of —XR$^4$, —N(R$^1$)—X—R$^4$, —N(R$^1$)—N(R$^1$)—X—R$^4$, and formula VI; wherein any structure of formula VI is unfused or fused with an aryl, carbocyclic or heterocyclic ring and is unsubstituted or substituted with 1–3 members independently selected from R$^2$.

23. The compound of claim 1, selected from the group consisting of:

| Cmpd. No. | A | Z |
|---|---|---|

-continued
| Cmpd. No. | A | Z |
|---|---|---|
| 49 | 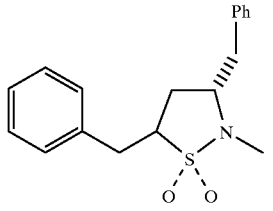 | 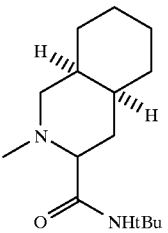 |
| 50 | 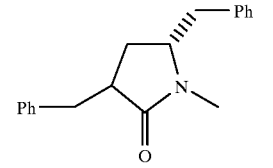 | 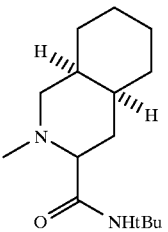 |
| 51 | 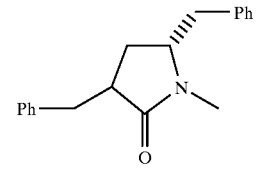 | 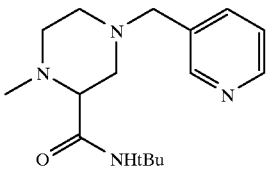 |
| 52 | 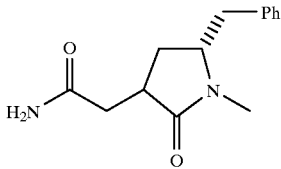 | 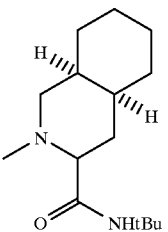 |
| 53 | 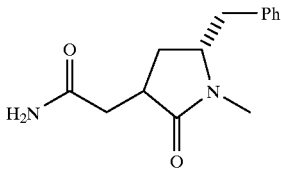 | 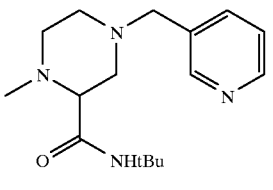 |
| 54 | 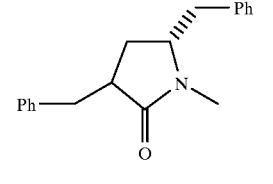 | 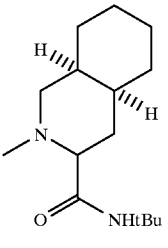 |
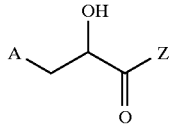

-continued

| Cmpd. No. | A | Z |
|---|---|---|
| 66 | 1-benzyl-3-methyl-4-benzyl-imidazolidin-2-one | N-tBu thiazolidine-4-carboxamide, N-methyl |
| 67 | 1-methyl-3-benzyl-5-benzyl-pyrrolidin-2-one | N-tBu thiazolidine-4-carboxamide, N-methyl |

24. The compound of claim 23, selected from the group consisting of compound numbers:

A—CH$_2$—CH(OH)—CH$_2$—Z

| Cmpd. No. | A | Z |
|---|---|---|
| 2 | 1-allyl-3-methyl-4-benzyl-imidazolidin-2-one | decahydroisoquinoline-3-carboxamide, N-methyl, NHtBu |
| 8 | 1-methyl-3-allyl-5-benzyl-pyrrolidin-2-one | decahydroisoquinoline-3-carboxamide, N-methyl, NHtBu |
| 9 | 1-methyl-3-allyl-5-benzyl-pyrrolidin-2-one | piperazine-2-carboxamide, 1-methyl-4-(3-pyridylmethyl), NHtBu |

-continued

| Cmpd. No. | A | Z |
|---|---|---|
| 49 | [structure: 2-benzyl-3-benzyl-N-methyl isothiazolidine 1,1-dioxide] | [structure: decahydroisoquinoline with N-Me and C(O)NHtBu] |
| 50 | [structure: 3-benzyl-5-benzyl-1-methylpyrrolidin-2-one] | [structure: decahydroisoquinoline with N-Me and C(O)NHtBu] |
| 51 | [structure: 3-benzyl-5-benzyl-1-methylpyrrolidin-2-one] | [structure: 4-(pyridin-3-ylmethyl)-1-methylpiperazine-2-carboxamide NHtBu] |
| 52 | [structure: 3-(carbamoylmethyl)-5-benzyl-1-methylpyrrolidin-2-one] | [structure: decahydroisoquinoline with N-Me and C(O)NHtBu] |
| 53 | [structure: 3-(carbamoylmethyl)-5-benzyl-1-methylpyrrolidin-2-one] | [structure: 4-(pyridin-3-ylmethyl)-1-methylpiperazine-2-carboxamide NHtBu] |

Structure header: A—CH₂—CH(OH)—CH₂—Z

25. The compound of claim 24, selected from the group consisting of compound numbers:

| Cmpd. No. | A | Z |
|---|---|---|
| 8 | (5-benzyl-3-allyl-1-methyl-pyrrolidin-2-one) | (decahydroisoquinoline-N-methyl-3-carboxamide NHtBu) |
| 9 | (5-benzyl-3-allyl-1-methyl-pyrrolidin-2-one) | (N-methyl-piperazine with 3-pyridylmethyl, carboxamide NHtBu) |
| 50 | (5-benzyl-3-benzyl-1-methyl-pyrrolidin-2-one) | (decahydroisoquinoline-N-methyl-3-carboxamide NHtBu) |
| 51 | (5-benzyl-3-benzyl-1-methyl-pyrrolidin-2-one) | (N-methyl-piperazine with 3-pyridylmethyl, carboxamide NHtBu) |
| 52 | (5-benzyl-3-carbamoylmethyl-1-methyl-pyrrolidin-2-one) | (decahydroisoquinoline-N-methyl-3-carboxamide NHtBu) |
| 53 | (5-benzyl-3-carbamoylmethyl-1-methyl-pyrrolidin-2-one) | (N-methyl-piperazine with 3-pyridylmethyl, carboxamide NHtBu) |

Structure header: A—CH$_2$—CH(OH)—CH$_2$—Z

26. A pharmaceutical composition comprising an amount of a compound according to claim 1 effective in inhibiting aspartyl protease and a pharmaceutically acceptable carrier, adjuvant or vehicle.

27. The pharmaceutical composition according to claim 9, wherein said pharmaceutical composition is orally administrable.

28. The pharmaceutical composition according to claim 9, wherein said pharmaceutical composition further comprises an agent capable of inhibiting the metabolic effects of one or more cytochrome $P_{450}$ enzyme subtypes.

29. A method for inhibiting aspartyl protease activity comprising the step of contacting an aspartyl protease with the compound according to claim 1.

30. A method for reversibly binding an aspartyl protease comprising the step of contacting the aspartyl protease with the compound according to claim 1, said compound being covalently bound to a solid matrix.

31. A method for treating HIV infection in a mammal comprising the step of administering to said mammal a pharmaceutically effective amount of a pharmaceutical composition according to either claim 26 or 27.

32. A method for treating HIV infection in a mammal comprising the step of administering to said mammal a pharmaceutical composition according to claim 28.

33. The method according to claim 29, further comprising the step of administering, to the mammal one or more additional agents selected from the group consisting of other anti-viral agents and immunostimulators via a single or multiple dose.

34. The method according to claim 31, wherein said other anti-viral agent is a protease inhibitor or reverse transcriptase inhibitor.

35. The method according to claim 32, wherein said protease inhibitor is an HIV protease inhibitor.

36. The method according to claim 33, wherein said HIV protease inhibitor is selected from the group consisting of VX-478, saquinavir, indinavir ritonavir, nelfinavir, palinavir, U-103017, XM 412, XM 450, BMS 186318, CPG 53,437, CPG 61,755, CPG 70,726, ABT 378, GS 3333, GS 3403, GS 4023, GS 4035, GS 4145, GS 4234, and GS 4263.

37. The method according to claim 32, wherein said reverse transcriptase inhibitor is a nucleoside analog.

38. The method according to claim 35, wherein said nucleoside analog is selected from the group consisting of zidovudine (AZT), dideoxycytidine (ddC), didanosine (ddI), stavudine (d4T), 3TC, 935U83, 1592U89 and 524W91.

39. The method according to claim 32, wherein said reverse transcriptase inhibitor is a non-nucleoside analog.

40. The method according to claim 37, wherein said non-nucleoside reverse transcriptase inhibitor is delavirdine (U90) or nevirapine.

41. A method for treating viral infection comprising the step of administering to said mammal a pharmaceutical composition according to either claim 23 or 24.

42. A method for treating or preventing HIV related disease effects, including tumors, CMV retinitis, candida infections, maternal fetal transmission, or AIDS related dementia, comprising the step of administering to said mammal a pharmaceutical composition according to either claim 23 or 24.

43. The composition according to claim 25, wherein the additional anti-viral agents are 3TC and zidovudine (AZT).

44. The composition according to claim 25, wherein the additional anti-viral agent is 1592U89.

* * * * *